(12) United States Patent
Saito

(10) Patent No.: US 10,741,286 B2
(45) Date of Patent: Aug. 11, 2020

(54) STRESS EVALUATION PROGRAM FOR MOBILE TERMINAL AND MOBILE TERMINAL PROVIDED WITH PROGRAM

(71) Applicants: Ryozo Saito, Tokyo (JP); Hirotsugu Takahashi, Tokyo (JP); Tetsu Kayama, Kanagawa (JP)

(72) Inventor: Ryozo Saito, Tokyo (JP)

(73) Assignees: Ryozo Saito, Tokyo (JP); Hirotsugu Takahashi, Tokyo (JP); Tetsu Kayama, Kanagawa (JP); Su-Li Hsieh, Taipei (TW)

(*) Notice: Subject to any disclaimer, the term of this patent is extended or adjusted under 35 U.S.C. 154(b) by 196 days.

(21) Appl. No.: 15/576,965

(22) PCT Filed: May 27, 2015

(86) PCT No.: PCT/JP2015/065307
§ 371 (c)(1),
(2) Date: May 7, 2018

(87) PCT Pub. No.: WO2016/189711
PCT Pub. Date: Dec. 1, 2016

(65) Prior Publication Data
US 2018/0255167 A1 Sep. 6, 2018

(51) Int. Cl.
*G16H 40/63* (2018.01)
*A61B 5/16* (2006.01)
(Continued)

(52) U.S. Cl.
CPC .............. *G16H 40/63* (2018.01); *A61B 5/163* (2017.08); *G06F 9/445* (2013.01);
(Continued)

(58) Field of Classification Search
CPC .... A61B 3/11; A61B 5/4884; G06K 9/00604; G06T 7/0016; G06T 7/20
See application file for complete search history.

(56) References Cited

U.S. PATENT DOCUMENTS 9,931,069 B2 * 4/2018 Publicover ........... A61B 3/0008
2004/0024287 A1 * 2/2004 Patton .................. A61M 21/00
600/27
(Continued)

FOREIGN PATENT DOCUMENTS

CN 1994227 A 7/2007
JP 2005 143684 A 6/2005
(Continued)

OTHER PUBLICATIONS

Uetake, Atsushi, et al. "Evaluation of visual fatigue during VDT tasks." Smc 2000 conference proceedings. 2000 ieee international conference on systems, man and cybernetics.'cybernetics evolving to systems, humans, organizations, and their complex interactions' (cat. No. 0. vol. 2. IEEE, 2000. (Year: 2000).*

*Primary Examiner* — Li Liu
(74) *Attorney, Agent, or Firm* — Muncy, Geissler, Olds & Lowe, P.C.

(57) ABSTRACT

To provide a technique for measuring a state of stress by objective symptoms having a correlation with stress in a mobile terminal device. In order to the above object, a program is provided, and a mobile terminal device reads and executes the program to perform: a video-on step for enabling a moving image capturing function of the mobile terminal; a light-on step for enabling a light disposed at an image capturing side of the mobile terminal; a pupil recognition step for recognizing pupils of animal eyes from an image that is being captured, wherein the animal eyes include human eyes; and a pupil change calculation step for
(Continued)

calculating a pupil change, wherein the pupil change is a change in a dilation level of the recognized pupil over time.

14 Claims, 42 Drawing Sheets

(51) Int. Cl.
  *G06K 9/00* (2006.01)
  *G06F 9/445* (2018.01)
  *G06T 7/00* (2017.01)
  *G16H 30/40* (2018.01)
  *A61B 3/11* (2006.01)
  *G06F 9/451* (2018.01)
  *G16H 50/20* (2018.01)

(52) U.S. Cl.
  CPC ..... G06K 9/00536 (2013.01); G06K 9/00604 (2013.01); G06T 7/0016 (2013.01); G16H 30/40 (2018.01); *A61B 3/11* (2013.01); *G06F 9/451* (2018.02); *G06T 2207/10016* (2013.01); *G06T 2207/10024* (2013.01); *G06T 2207/10152* (2013.01); *G06T 2207/30041* (2013.01); *G16H 50/20* (2018.01)

(56) References Cited

U.S. PATENT DOCUMENTS

| | | | | |
|---|---|---|---|---|
| 2004/0176991 | A1* | 9/2004 | McKennan | G06F 3/011 702/182 |
| 2004/0196433 | A1* | 10/2004 | Durnell | G06K 9/00604 351/209 |
| 2014/0282646 | A1* | 9/2014 | McCoy | H04N 21/44213 725/12 |
| 2015/0015460 | A1* | 1/2015 | Kobayashi | G09G 5/10 345/8 |
| 2015/0223688 | A1* | 8/2015 | Wang | A61B 3/152 351/208 |
| 2015/0297140 | A1* | 10/2015 | Hernandez | A61B 5/6897 600/547 |
| 2017/0146801 | A1* | 5/2017 | Stempora | G06Q 10/063 |

FOREIGN PATENT DOCUMENTS

| | | |
|---|---|---|
| JP | 2005-143684 A | 6/2005 |
| JP | 2005-163684 A | 6/2005 |
| JP | 2008-212179 A | 9/2008 |
| JP | 2009-142469 A | 7/2009 |
| JP | 2011-239891 A | 12/2011 |
| JP | 5438591 B2 | 12/2011 |
| JP | 2012-065016 A | 3/2012 |
| WO | WO2014184868 A1 | 11/2014 |

* cited by examiner

| Sunday | Monday | Tuesday | Wednesday | Thursday |
|---|---|---|---|---|
|  | 1<br><br>35/100 | 2<br><br>37/100 | 3<br><br>40/100 | 4<br><br>46/100 |
| 7<br><br>20/100 | 8<br><br>30/100 | 9<br><br>34/100 | 10<br><br>39/100 | 11<br><br>49/100 |
| 14<br><br>27/100 | 15<br><br>34/100 | 16<br><br>36/100 | 17<br><br>42/100 | 18<br><br>45/100 |
| 21<br><br>24/100 | 22<br><br>31/100 | 23<br><br>33/100 | 24<br><br>35/100 | 25<br><br>41/100 |

STRESS EVALUATION PROGRAM FOR MOBILE TERMINAL AND MOBILE TERMINAL PROVIDED WITH PROGRAM

BACKGROUND

Technology Field

This disclosure relates to a stress evaluation program applied to a mobile terminal.

Description of Related Art

The stress is the reason for causing various diseases. However, in general, the stress cannot be visually recognized and is not easily measured by a device or the likes.

Therefore, the preferred technique is to measure the state of stress based on the objective symptoms associated with stress.

The above technique can be referred to those disclosed in the following references.

REFERENCE OF CONVENTIONAL ART

Patent Reference

Patent reference 1: JP Patent Application No. 2005-143684

SUMMARY

The Problem to be Solved by this Invention

The above patent reference is to find the correlation between the stress or relaxation level and the pupil response to light. The concept of this reference is to capture the image of eyes and analyze the pupil response to light irradiation so as to measure the stress level. According to this concept, the purpose of measuring the stress state according to the objective symptoms having a correlation with stress can be achieved.

However, in the patent reference, the user must wear a stereo mask to cover the eyes and face of the user before capturing the image. The need of the stereo mask will make the user uncomfortable.

Currently, the popularity of mobile terminal devices such as smart phones is high, so that objective stress measurement using the mobile terminal device can be easily used by the user. In such a mobile terminal device, for example, when photographing is performed using a smart phone or the likes, it is a problem that it is not creative to recognize the pupil and fail to grasp the pupil size change.

Accordingly, a subjective of this disclosure is to provide a technique applied to a mobile terminal device for measuring the state of stress based on the objective symptoms associated with stress.

The Solution for Solving the Problem of this Invention

In order to solve the above subjective, this disclosure provides a program recorded and readable by a mobile terminal device, and the mobile terminal device reads and executes the program to perform: a video-on step for enabling a moving image capturing function of the mobile terminal; a light-on step for enabling a light disposed at an image capturing side of the mobile terminal; a pupil recognition step for recognizing pupils of animal eyes from an image that is being captured, wherein the animal eyes include human eyes; and a pupil change calculation step for calculating a pupil change, wherein the pupil change is a change in a dilation level of the recognized pupil over time.

In addition, expect the above characteristics, the disclosure further provides a program, which further includes an illuminance change step for changing an illuminance of the light that enabled in the light-on step over time.

In addition, expect the above characteristics, the disclosure further provides a program, which further includes a body composition data obtaining step for obtaining body composition data from a body composition meter.

In addition, expect the above characteristics, the disclosure further provides a program, which further includes a stress evaluation step for evaluating a stress level according to the pupil change obtained by the pupil change calculation step to obtain a stress evaluation result.

In addition, expect the above characteristics, the disclosure further provides a program, which further includes a pupil change transmission step for transmitting the pupil change obtained by the pupil change calculation step to a preset address. Moreover, the disclosure further provides a program recorded and readable by a computer, and the computer reads and executes the program to perform: a pupil change receiving step for receiving the pupil change; a pupil change accumulation step for accumulating the received pupil change; and a pupil change statistical processing step for performing a statistical processing of the accumulated pupil changes.

In addition, expect the above characteristics, the disclosure further provides a program, which further includes a stress evaluation result transmission step for transmitting the stress evaluation result obtained by the stress evaluation step to a preset address. Moreover, the disclosure further provides a program recorded and readable by a computer, and the computer reads and executes the program to perform: a pupil change receiving step for receiving the pupil change transmitted out by the pupil change transmission step; a pupil change accumulation step for accumulating the received pupil change; a stress evaluation result receiving step for further receiving the stress evaluation result transmitted out by the stress evaluation result transmission step; a stress evaluation result accumulation step for accumulating the received stress evaluation result; and a pupil change statistical processing step for performing a statistical processing of the accumulated pupil changes and the accumulated stress evaluation results.

In addition, expect the above characteristics, the disclosure further provides a program, in which the video-on step for enabling the moving image capturing function of the mobile terminal is replaced by a continuous ON step for enabling a continuous still image capturing function of the mobile terminal.

In addition, this disclosure provides a program recorded and readable by a mobile terminal device, and the mobile terminal device reads and executes the program to perform: a video-on step for enabling a moving image capturing function of the mobile terminal; a light-on step for enabling a light disposed at an image capturing side of the mobile terminal; a moving image saving step for saving a moving image captured by the video-on step; and a moving image transmission step for transmitting the saved moving image to a preset address. In addition, expect the above characteristics, the disclosure further provides a program recorded and readable by a mobile terminal device, and the mobile terminal device reads and executes the program to perform:

a continuous ON step for enabling a continuous still image capturing function of the mobile terminal, which is used to replace the video-on step for enabling the moving image capturing function of the mobile terminal; a continuous still image saving step for saving a continuous still image captured by the mobile terminal, which is used to replace the moving image saving step for saving the moving image captured by the video-on step; and a continuous still image transmission step for transmitting the continuous still image saved by the continuous still image saving step, which is used to replace the moving image transmission step for transmitting the saved moving image to the preset address.

In addition, this disclosure provides a program recorded and readable by a computer, and the computer reads and executes the program to perform: a moving image receiving step for receiving a moving image including animal eyes from a mobile terminal, wherein the animal eyes include human eyes; a pupil recognition step for recognizing pupils of the animal eyes from the received moving image; and a pupil change calculation step for calculating a pupil change, wherein the pupil change is a change in a dilation level of the recognized pupil over time. In addition, the disclosure further provides a program recorded and readable by a computer, and the computer reads and executes the program to perform: a continuous still image receiving step for receiving a continuous still image including animal eyes from a mobile terminal, wherein the animal eyes include human eyes; a pupil recognition step for recognizing pupils of the animal eyes from the received continuous still image; and a pupil change calculation step for calculating a pupil change, wherein the pupil change is a change in a dilation level of the recognized pupil over time.

In addition, the disclosure provides a mobile terminal device or a statistical processing device, which records, reads and executes the above programs.

Effect of this Invention

This disclosure provides a technique applied to a mobile terminal device for measuring the state of stress based on the objective symptoms associated with stress.

DETAILED DESCRIPTION OF THE DISCLOSURE

The embodiments and aspects of this disclosure will be described hereinafter with reference to the accompanying drawings. In the following descriptions, the first embodiment corresponds to claims 1, 13 and 25, the second embodiment corresponds to claims 2 and 14, the third embodiment corresponds to claims 3 and 15, the fourth embodiment corresponds to claims 4 and 16, the fifth embodiment corresponds to claims 5 and 17, the sixth embodiment corresponds to claims 8 and 18, the seventh embodiment corresponds to claims 6 and 19, the eighth embodiment corresponds to claims 9 and 21, the ninth embodiment corresponds to claims 10 and 22, the eleventh embodiment corresponds to claims 11 and 23, and the twelfth embodiment corresponds to claims 12 and 24. To be noted, the disclosure is not limited to the following embodiments, and any modification without departing the scope of this disclosure can be performed.

First Embodiment

<Summary>

A program according to an embodiment of this disclosure is recorded and readable by a mobile terminal device, and the mobile terminal device reads and executes the program to capture the moving image of the pupil change when irradiated by light, and to calculate the pupil change of the obtained image over time. In addition, a mobile terminal device that reads and executes the recorded program is also provided. The mobile terminal device can be a mobile terminal or other terminals, such as a desktop computer. In the following embodiments, the mobile terminal device is a mobile terminal for an example.

The function and hardware of the mobile terminal device and the processing procedure of this embodiment will be described hereinafter.

<Functional Compositions>

Figure 1:
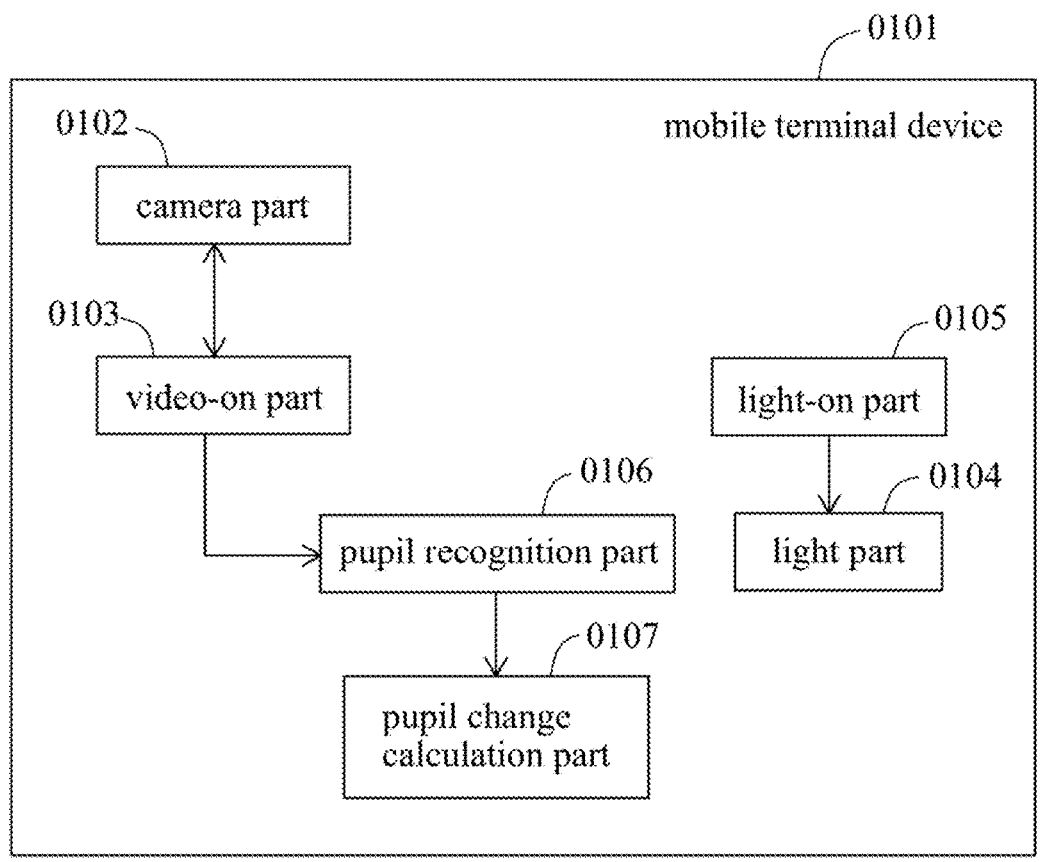
FIG. 1 is a functional block diagram of a mobile terminal device according to a first embodiment.

FIG. 1 is a functional block diagram of a mobile terminal device according to an embodiment. As shown in FIG. 1, the mobile terminal device (0101) of this embodiment includes a camera part (0102), a video-on part (0103), a light part (0104), a light-on part (0105), a pupil recognition part (0106), and a pupil change calculation part (0107).

In addition, the functional blocks constituting the mobile terminal device described below can be implemented by hardware, software, or both of hardware and software. More specifically, if a computer is used, it is possible to use a CPU; a main memory, a bus or a secondary storage device (a storage medium such as a hard disk, a nonvolatile memory, a CD-ROM or a DVD-ROM and a reading drive of these medium), the hardware components such as a printing device, a display device, and other external peripheral device, the I/O ports for the external peripheral devices, driver programs or other application programs for controlling these hardware, a user interface for information input, and the likes.

In addition, these hardware and software are capable of performing arithmetic processing of programs developed on the main memory by the CPU, processing and storing the data retained in the memory or the hard disk or inputted via the interface, output processing, or controlling each of the hardware components. Furthermore, the disclosure can be implemented not only as an apparatus but also as a method. Moreover, a part of this disclosure can be configured as software. Furthermore, a software product used for causing a computer to execute such software, and a recording medium recording the software product are naturally included in the technical scope of the disclosure (the same applies throughout this specification).

<<Functions of Camera Part and Light Part>>

The camera part includes a function for capturing a moving image and/or a still image. In addition, the light part includes a light disposed at an image capturing side of the mobile terminal. The camera part and the light part can be disposed on the front side or the rear side, but the object of the disclosure can be attained in either case.

Figure 31:
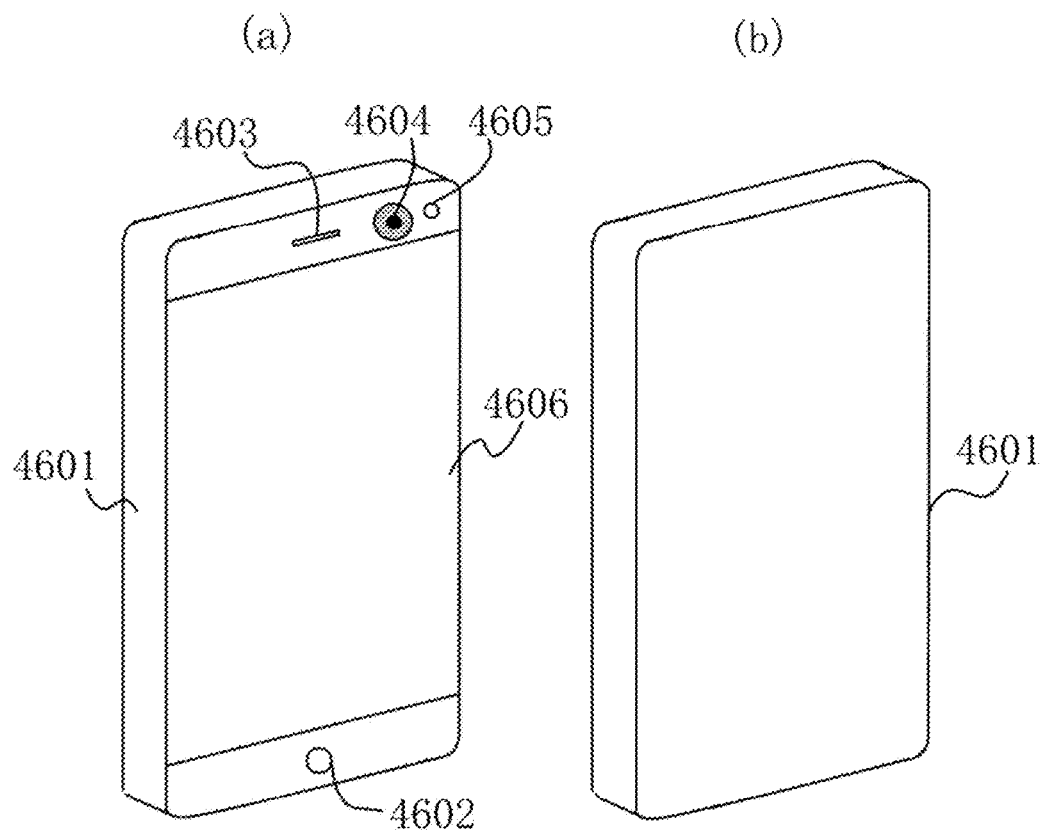
FIG. 31 is an experimental diagram 1 of the mobile terminal device.
Figure 32:
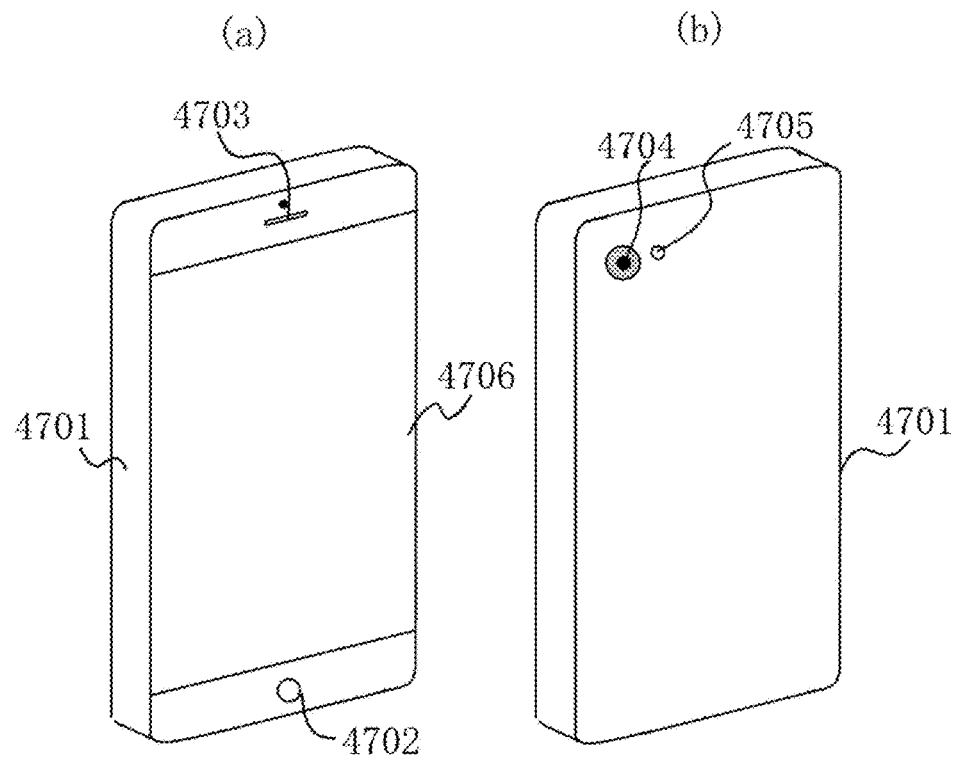
FIG. 32 is an experimental diagram 2 of the mobile terminal device.
Figure 33:
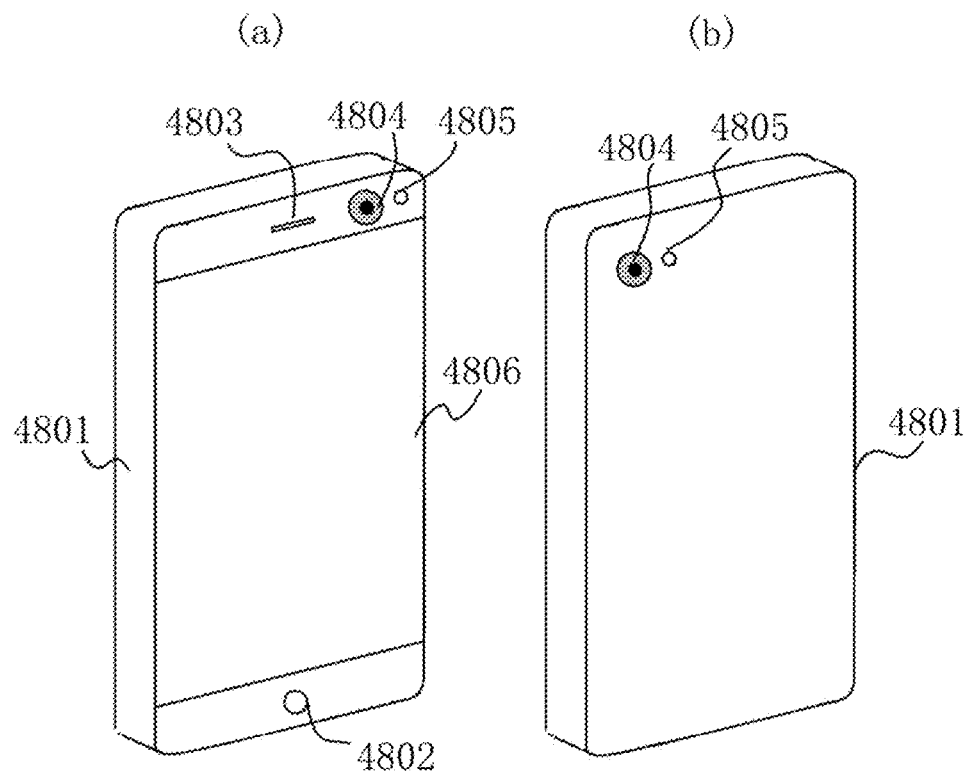
FIG. 33 is an experimental diagram 3 of the mobile terminal device.

FIGS. 31 to 33 are schematic diagrams of a smart phone (one of the mobile terminal devices), wherein (a) shows the front side and (b) shows the rear side. In fact, a microphone (not shown) is also configured.

In the front side of the mobile terminal device (4601) of FIG. 31, except the operation keys (4602) and the receiving part (4603), it further includes a camera (4604), a light (4605) and a screen (4606). The rear side thereof is not configured with any camera and light.

In the front side of the mobile terminal device (4701) of FIG. 32, it includes operation keys (4702), a receiving part (4703) and a screen (4706). The rear side thereof is configured with a camera (4704) and a light (4705).

In the front side of the mobile terminal device (4801) of FIG. 33, except the operation keys (4802) and the receiving part (4803), it further includes a camera (4804), a light (4805) and a screen (4806). The rear side thereof is also configured with a camera (4804) and a light (4805).

For example, when operating the mobile terminal as shown in FIG. 31 or 33, the user can perform a moving image capturing upon viewing the screen. Accordingly, as shown in FIG. 31, the mobile terminal is preferably configured with the camera and light at the front side, which is configured with the screen.

In addition, when operating the mobile terminal as shown in FIG. 32, in order to output the light to the pupil, the user must face the rear side opposite to the screen. Accordingly, the user cannot control the position of his/her eye or pupil on which place of the screen, and it will cause some problems on the operation. A pupil position control device can output a sound so that the user can realize and control the position of the pupil. Accordingly, when the pupil is not located around the center of the screen, the pupil position control device can output a sound to indicate that the pupil is located at the right or left of the center. In addition, when the pupil is located around the center of the screen, the pupil position control device can output a beep sound. Expect outputting sounds, the pupil position control device can change the illuminance of the light to indicate that the pupil is approaching the center of the screen.

Since the infrared light can easily recognize the size of pupil, the camera is preferably configured with an IR camera function.

In addition, when the screen faces the user and the screen side of the mobile terminal device is only configured with the camera, a part of the screen can display a high-illuminance white light image to replace the light. The high-illuminance white light image can be displayed on the top-half or bottom-half of the screen, or on the top-quarter or bottom-quarter of the screen. The ratio of the displayed part of the captured image and the part of the high-illuminance white light image is not necessary to be 1:1, and as long as the ratio that is enough to measure the pupil response to light is acceptable.

Figure 46:
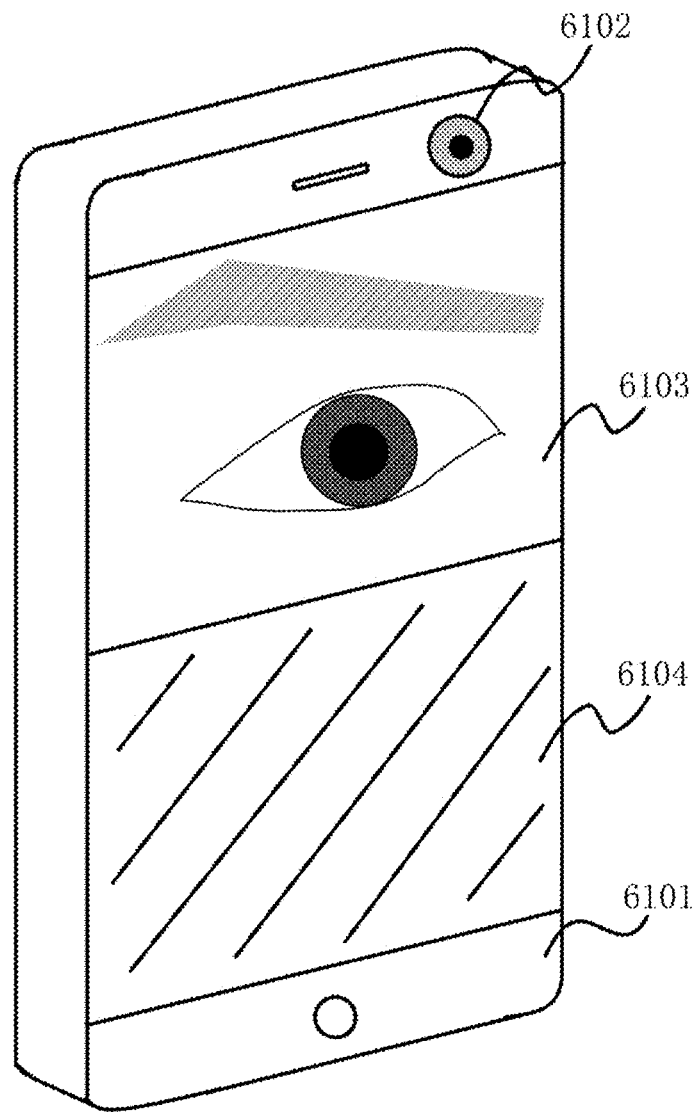
FIG. 46 is a schematic diagram showing the mobile terminal device, wherein a part of the screen is a high-illuminance white light image.

FIG. 46 is a schematic diagram showing the mobile terminal device, wherein a part of the screen is a high-illuminance white light image. In this case, the mobile terminal device (6101) includes a camera (6102), but it is not configured with a light. Thus, the bottom-half of the screen (6103) displays a high-illuminance white light image (6104) for replacing the light.

<<Functions of the Video-on Part and the Light-on Part>>

The video-on part is configured to enable a moving image capturing function of the mobile terminal. The light-on part is configured to enable the light, which is disposed at an image capturing side of the mobile terminal. As the basic structure of this disclosure, it is needed to capture the moving image of the pupil change when irradiating light to the pupil. The function of the video-on part is enabled to capture the moving image of the pupil of the user. In addition, the function of the light-on part is enabled to output light to irradiate the pupil of the user.

"Image capturing" of the video-on part includes a case of simultaneously recording, but recording is not indispensable. For example, in the embodiment, the video-on part only captures a moving image, and the following "pupil recognition part" and "pupil change calculation part" calculate in real time with the moving image being captured.

Also, it is desirable that the moving image being captured includes not only the moving image during the lighting but also the moving image before and after the lighting. By including the moving images before and after being irradiated with light in this manner, it is possible to accurately measure the pupil response to light.

Here, it is premised that the pupil is included in the moving image during image capturing, but it is preferable not only the pupil but also the body part around the pupil other than the pupil is included. In the human eyeball, the health condition of the person appears in various forms. For example, in allergic conjunctivitis, infectious conjunctivitis, uveitis or dry eye, eye irritation is caused. Therefore, there is an effect that it is possible to know the above-mentioned symptoms due to the fact of eye congestion occurring in the conjunctiva.

Next, the "mobile terminal" broadly includes, for example, a smart phone, a mobile phone, a notebook computer, a tablet computer, a watch-type computer, a wearable computer, a digital camera, a PDA, a Pocket PC, a Palm, a dedicated terminal with a light and a camera. Normally, it assumes a device with a camera function and a light function, but in the present disclosure, as a unit being sold, even a device does not have a camera function or a light function but a camera or a light can be mounted externally, the device and the external camera or the external light shall be considered as a "mobile terminal" as a whole.

The intensity of the light to be irradiated by the light-on part may be any intensity as long as it can cause a light response of the pupil. In addition, in view of the fact that the fundus examination is performed by applying light to the pupil, it is conceivable to set the intensity of light appropriate for performing fundus examination, for example. By doing so, simultaneous measurement of stress intensity and examination of fundus can be performed.

Further, the mobile terminal device may be provided with a control part for controlling a moving image capturing function and turning on/off the light. This control part automatically turns on and off the moving image shooting function and light at appropriate timing once the user turns on the switch.

In addition, the control part can also be configured to automatically enable the video-on function and the light at a preset time. By doing so, it is possible to measure the response of pupil to light at a specific time point. For example, it is possible to perform the automatic measurement during working time.

Accordingly, when the moving image is captured and the light irradiates the pupil, the pupil change can be captured.

<<Pupil Recognition Part>>

The pupil recognition part is configured to recognize pupils of animal eyes from an image that is being captured. In an issue of the disclosure, when the mobile terminal device, such as a smart phone, it is hard to catch the change of the pupil size. In specifically, although the video function of the mobile terminal generally has a face recognition function, the function for recognizing the pupil part of the eyeball is not equipped. In order to solve this issue, it is needed to calculate the pupil size according to the moving image information. If the pupil size cannot be recognized, the desired calculation is also impossible. The pupil recognition part can recognize the pupil size, and it is an important function to solve the issue of this disclosure.

As a function for recognizing the pupil, after the pupil is photographed, the color or brightness of the pupil is recorded based on the moving image or still image information of the pupil, and the same color or brightness as the recorded color or brightness is used to recognize the pupil.

In addition, the mobile terminal device may include a device for automatically recognizing the pupil portion even if the color or brightness of the pupil is not recorded. Specifically, referring to FIG. 38, it may include the following method: firstly, utilizing a color brightness recognizing device for recognizing the dark color portion (A), light color portion (B), white portion (C) and the skin portion (D) of the eyeball according to color or brightness; next, utilizing an iris recognition device to find a boundary E between the light color portion (B) and the white portion (C) of the eyeball; finally, utilizing a pupil finding device to find a boundary F between the dark color portion (A) and the light color portion (B).

Figure 50:
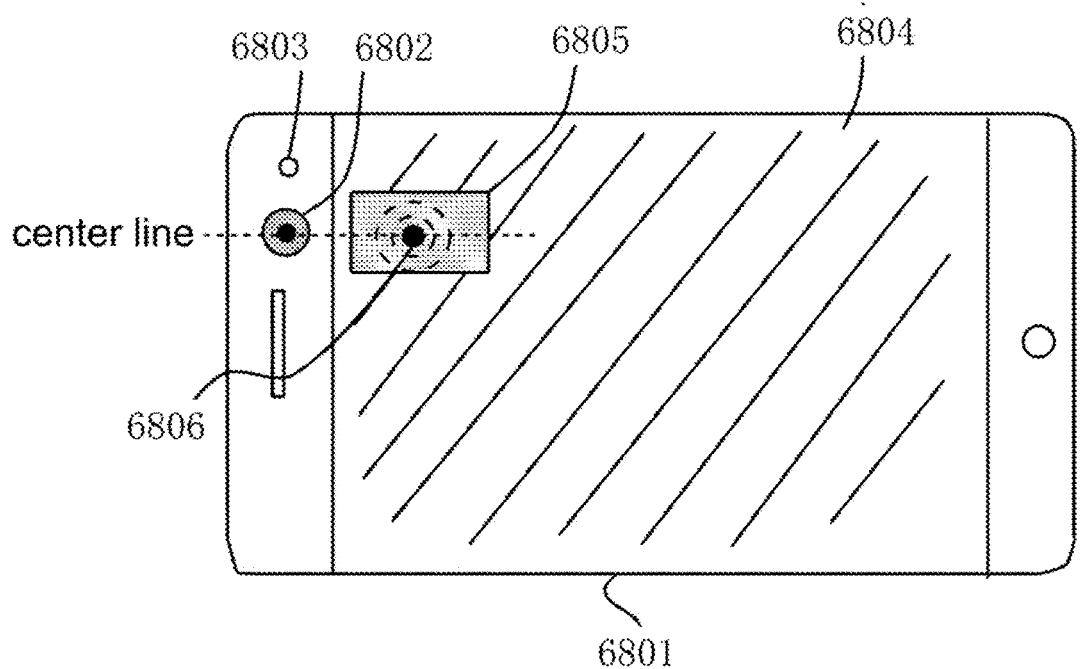
FIG. 50 is a schematic diagram showing that the stress recognition can be continued even the pupil part has a very slight move.

Even if a fine movement occurs in the pupil portion, it is preferred to continue the recognition procedure and tracing. Further, in order to prevent the fine movement of the pupil portion, for example, as shown in FIG. 50, the mobile terminal device (6801) is placed sideways, the image (6805), such as the moving image, is displayed on the screen (6804) near the camera (6802) or the light (6803), and a device for fixing the pupil portion at one point is provided. In this case, if the screen (6804) displays white light, it can be used to replace the light. When displaying the image such as a moving image, it is desirable to place the center line of the moving image on the center line of the camera (6802). Also, the attention point (6806) to be noticed in the image may be clearly indicated.

For the pupil portion, its circumference may be darker in some cases. In such a case, the inside of the portion having a darker color may be set as the boundary F, the outside thereof may be set as the boundary F, or the middle point thereof may be set as the boundary F. However, in order to improve the accuracy of information, it is undesirable to vary for each measurement, and it is desirable that it be a unified setting.

Figure 45:
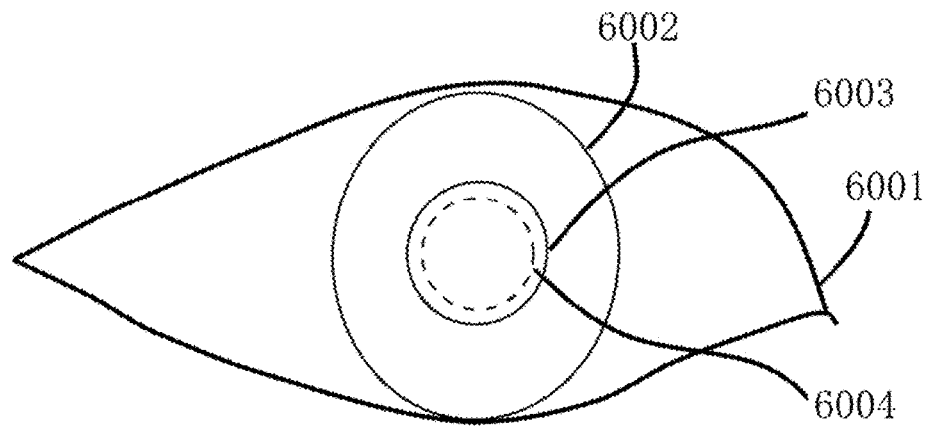
FIG. 45 is a schematic diagram showing the contour of human eye.

This point will be described with reference to FIG. 45. FIG. 45 is a diagram showing the contour of human eye. The human eye (6001) includes an iris boundary portion (6002) and a pupil boundary portion (6003). In some cases, a portion (6004) which has a darker color than the portion indicated by the dotted line is located inside the pupil. In such a case, the portion (6004) which has a darker color may be set as the boundary F, the pupil boundary portion (6003) may be set as the boundary F, or the intermediate point may be set as the boundary F.

Figure 34:
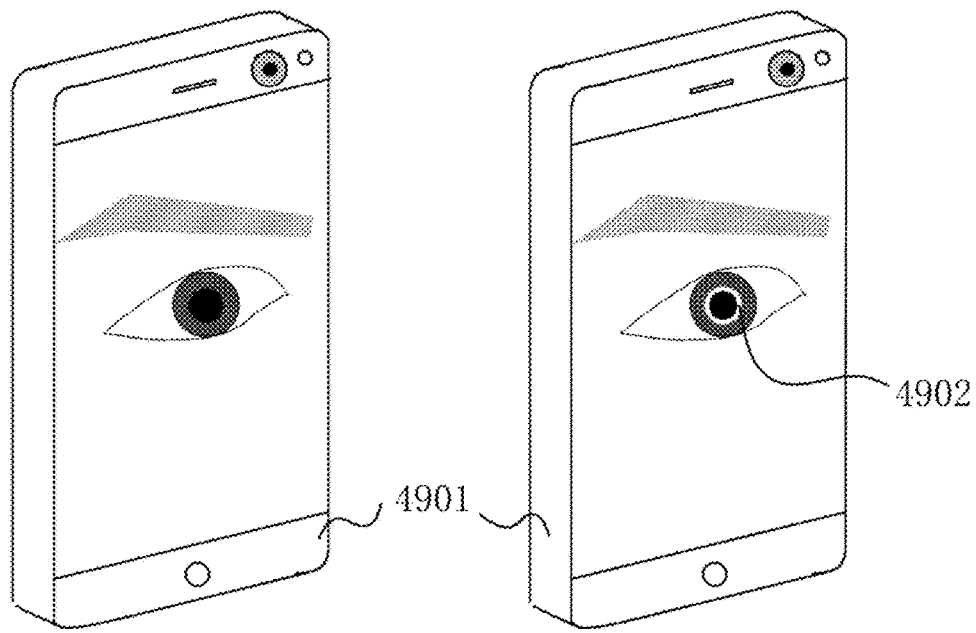
FIG. 34 is an experimental diagram showing the screen of the mobile terminal device that implements the disclosure.

FIG. 34 is a view showing a screen when a pupil is recognized. Using the mobile terminal device (4901), as shown in the left of the figure, to photograph the eye portion including the pupil, when the pupil portion is successfully recognized, it shows that the pupil has been recognized as shown in the right of the figure, so that the pupil portion (4902) emerges so as to notify the user that the pupil recognition is successful. Besides, as a device for communicating the success of the pupil recognition, for example, a method of notifying via notification sound of "beep" or change in illuminance, or the like, can be used, but it is not limited thereto.

In order to automatically recognize the pupil, it is desirable that the camera has an autofocus function for automatically adjusting the focus. In addition, since there is a possibility that camera shake may occur when the user operates it, it is desirable to have a camera shake prevention function. Thus, the accurate pupil recognition can be performed.

Also, while shooting a moving image, basically the user does not blink, so the user is attacked by symptoms such as dry eyes. Therefore, it is convenient for the user to be able to realize the elapsed seconds or remaining seconds. Thus, even during the moving image shooting, it is desirable that there is a device to inform the remaining time of shooting by sound or the like.

In addition, although the precision of calculation decreases in the case of blinking, the user may not notice that the blinking has occurred. Therefore, when blinking is recognized, in order to redo the moving image shooting, it may have a function to notify by notification sound, light ON/OFF, color, illuminance, or the like. In addition, when recognizing blinking, the moving image capturing may be provided with an extension function for extending the photographing time (measuring time) instead of restarting from the beginning.

《Pupil Change Calculation Part》

The pupil change calculation part is configured to calculate a pupil change, which is a change in a dilation level of the recognized pupil over time. As mentioned above, the stress or relaxation level is related to the pupil response to light. Therefore, the pupil change calculation part can calculate the pupil response to light. The pupil response to light is specifically the change of pupil size over time as the light irradiates the pupil.

The pupil data to be calculated may include the diameter of the pupil or the area of the pupil. For example, in terms of the diameter of the pupil, it is desirable to measure more accurately even when the entire image of the pupil is obstructed by eyelashes or the eyelids are not completely opened. On the other hand, if it is the area of the pupil, it is desirable that the size of the pupil can be captured accurately unless there is no such a circumstance as described above.

In addition to the diameter value or the area value, it is conceivable to calculate the time required to minimize the pupil, the pupil constriction rate, the pupil constriction speed, the pupil constriction acceleration, etc. The user can obtain the personal information of pupil response to light by the value or the like obtained by this calculation. Then, the user performs an analysis based on the correlation between the obtain information and the stress or relaxation level, thereby objectively realizing the stress or relaxation level of the user.

Furthermore, as the contents of the calculation, it is conceivable to calculate the time taken until the constricted pupil becomes normal (the original state), the pupil dilation rate, the pupil dilation speed, the pupil dilation acceleration. For that purpose, it may further have a "light-off part" for turning off the light provided on the capturing side of the mobile terminal. According to this, more accurate stress level can be obtained.

Figure 39:
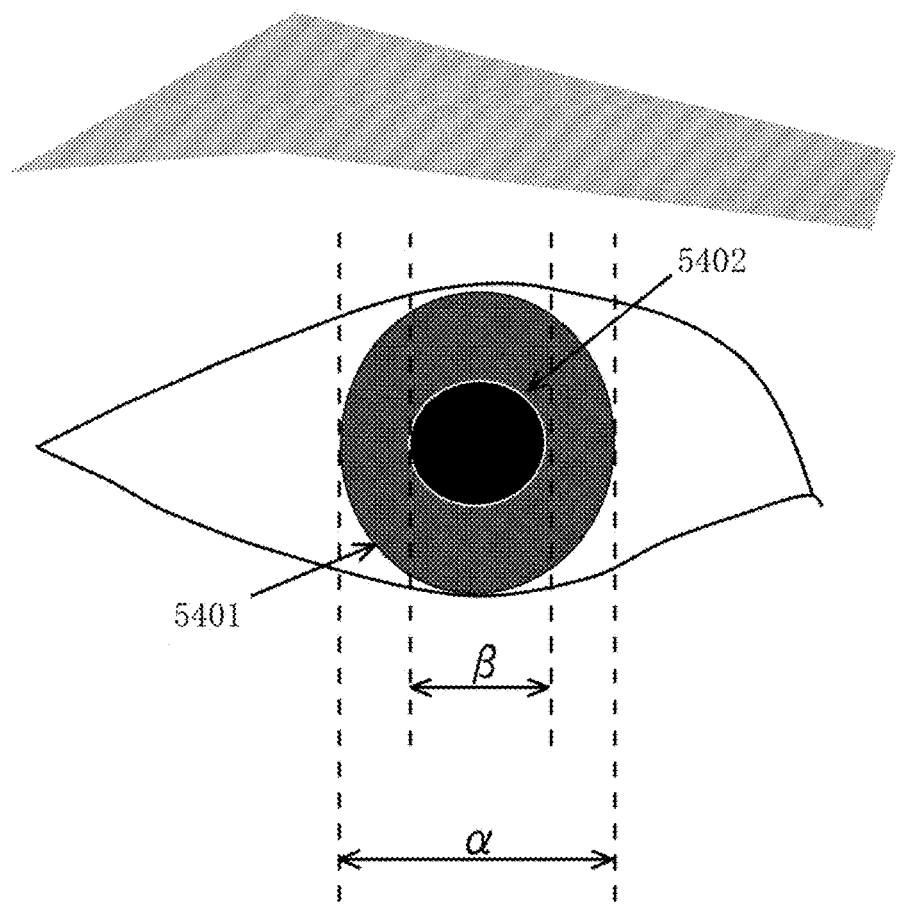
FIG. 39 is a diagram showing the content for pupil change calculation.

Regarding the specific content of the pupil calculation, considering that the distance from the photographed portion is not constant, even if the size of the pupil portion in the moving image is measured in a random manner, accurate pupil change cannot be measured. In order to realize accurate measurement, it is desirable that there is a structure that is less influenced by the distance from the photographed portion, the angle, or the likes. Specifically, for example, referring to FIG. 39, if the value is obtained by comparing the diameter α of the iris portion (5401) and the diameter β of the pupil portion (5402), the calculation will not be influenced by the distance from the photographed portion, the angle, and the likes. For example, in the example of FIG. 39, the calculation result is "α/β" or "β/α". Therefore, it is preferable to compare the diameter α of the iris portion with the diameter β of the pupil portion.

Figure 38:
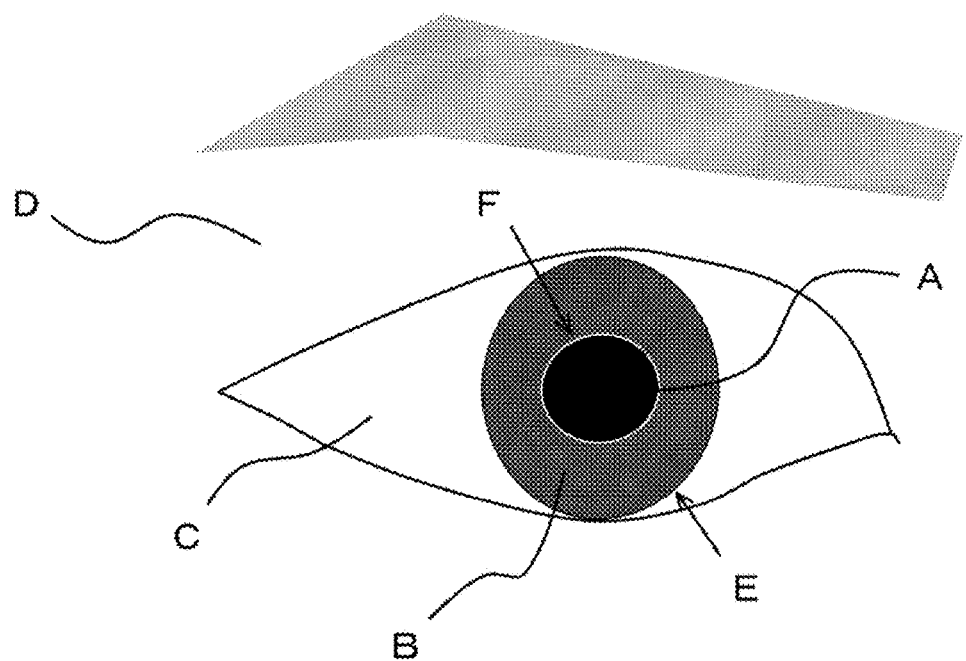
FIG. 38 is a diagram showing the content for pupil recognition.

In order to realize such a comparison, except the iris finding device and the pupil finding device described in FIG. 38, the comparison can obtained by utilizing a diameter measuring device for measuring the diameter of the iris portion and the pupil portion on a moving image and a division device for performing division on the measured diameters.

《Other》

Besides that, as the identification information for identifying the user, it may have a registration information receiving part for receiving registration information such as name, age, date of birth, meal tendency and the likes. It is preferable to receive the iris information of the user in association with this registration information. As a result, by performing the iris recognition using the camera of the mobile terminal device, a reliable user management can be performed regardless of the user ID or the like.

By attaching an external fan to the mobile terminal device, it is also possible to activate the fan and check the intraocular pressure at the same time. In the intraocular pressure examination, there is a tendency that the eye pressure tends to be measured with a high eye pressure when blinking, so the notifying function about the above-described blinking is useful for the fundus examination. By fundus examination, diseases such as glaucoma, retinal detachment, choroidal detachment, iridocyclitis and the likes can be detected out.

Also, in order to raise the value of information of pupil change, it is also possible to add information together such as name, gender, date of birth, hometown, measurement time, measurement place (e.g. residence, university, workplace, pub, train, park, or the likes), and food ingredients in the case of before or after meals, occupation, presence or absence and intensity of work at the measurement date, body composition data, treatment history and the likes. In particular, regarding birth date, it is necessary to realize the stress evaluation taking into account the biorhythm that can be a noise in evaluating stress. In the case where a GPS is installed in the mobile terminal device, the GPS function may be used to recognize the longitude/latitude of the measurement location and to determine the altitude from the information. Since stress can also be influenced by oxygen concentration, it has meaning as additional information.

It is further desirable to have a pupil change list output part for outputting pupil changes as a list. The list can be shown as a graph, a table, a calendar, etc.

Figure 35:
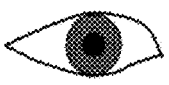
FIG. 35 is a diagram 1 showing the content of statistical processing.

FIG. 35 is a diagram showing the contents of statistical information processed in the pupil change list output part. For user A, the pupil changes are listed in each date. In addition to this, for example, information such as measurement conditions may be written in the date column. For example, if it is indicated together with information such as the brightness of the measured place, the measurement time, the time before and after meals, the sleeping time of the previous day, the presence or absence and intensity of work on the measurement day, the user can know the reason causing the stress, and this is helpful to reduce stress of life.

Figures 36, 37:
FIG. 36 is a diagram 2 showing the content of statistical processing.
FIG. 37 is a diagram 3 showing the content of statistical processing.

Further, when the boundary of the pupil is difficult to understand, as shown in FIG. 36, it is possible to make the pupil part recognized by the pupil recognition part conspicuous. In FIG. 36, a contrivance is made so that the contour of the pupil becomes clear.

Figure 51:
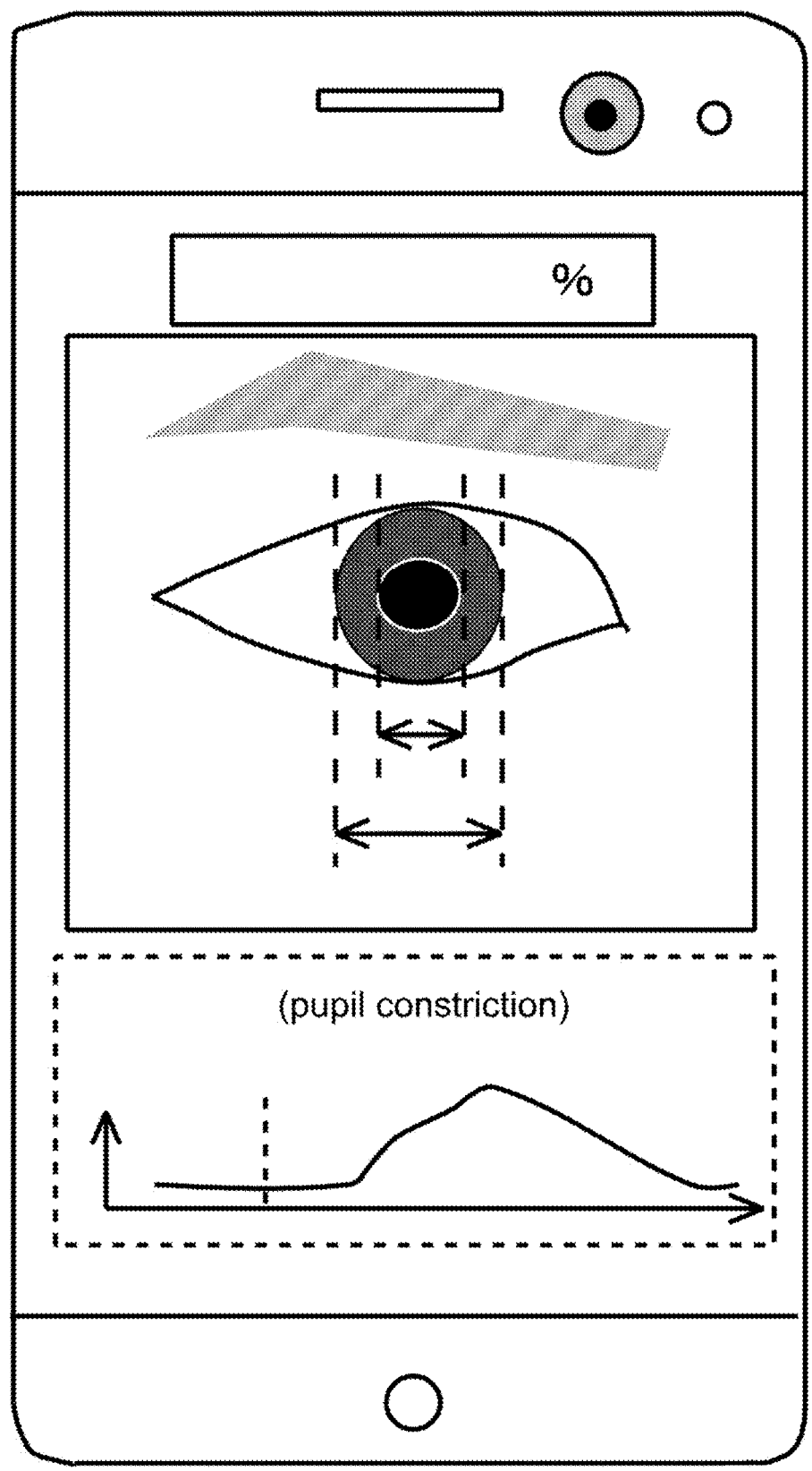
FIG. 51 is a schematic diagram showing a replayed image after the calculation is finished.

In addition, it is preferable that the mobile terminal device includes a replay part for replaying the captured moving image after completion of the calculation. In this replay, in order to confirm whether the pupil recognition in the pupil recognition part is accurate or not, it is desirable to have a configuration that: the part recognized as the pupil is blurred, or the part used for measurement as the diameter is clearly indicated as shown in FIG. 51.

Figure 52:
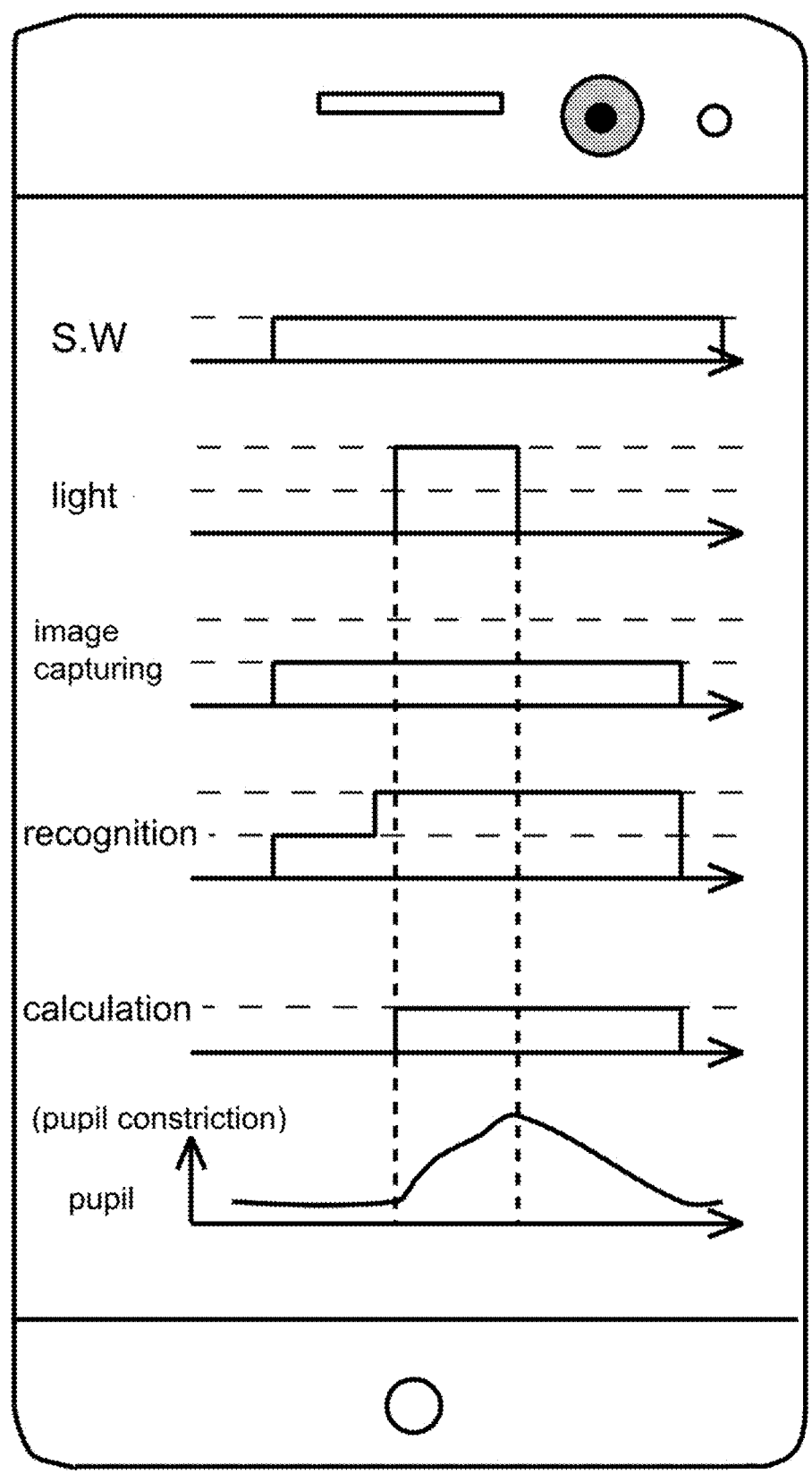
FIG. 52 is an experimental diagram showing the screen, which displays the data related to the pupil constriction.

Furthermore, data on pupil contraction may be displayed on the screen so that the pupil change can be confirmed immediately after image capturing. FIG. 52 shows an example of displaying data of pupil contraction in the screen. The timing at which the light gets brighter, the illuminance of the light, the transition of the pupil change, etc. are listed, and the user can recognize the calculation result at a glance.

《Conclusion》

By having the functions as described above, it is possible to provide a technique in the mobile terminal device for measuring the state of stress according to the objective symptoms having a correlation with stress.

<Hardware Configuration>

Figure 2:
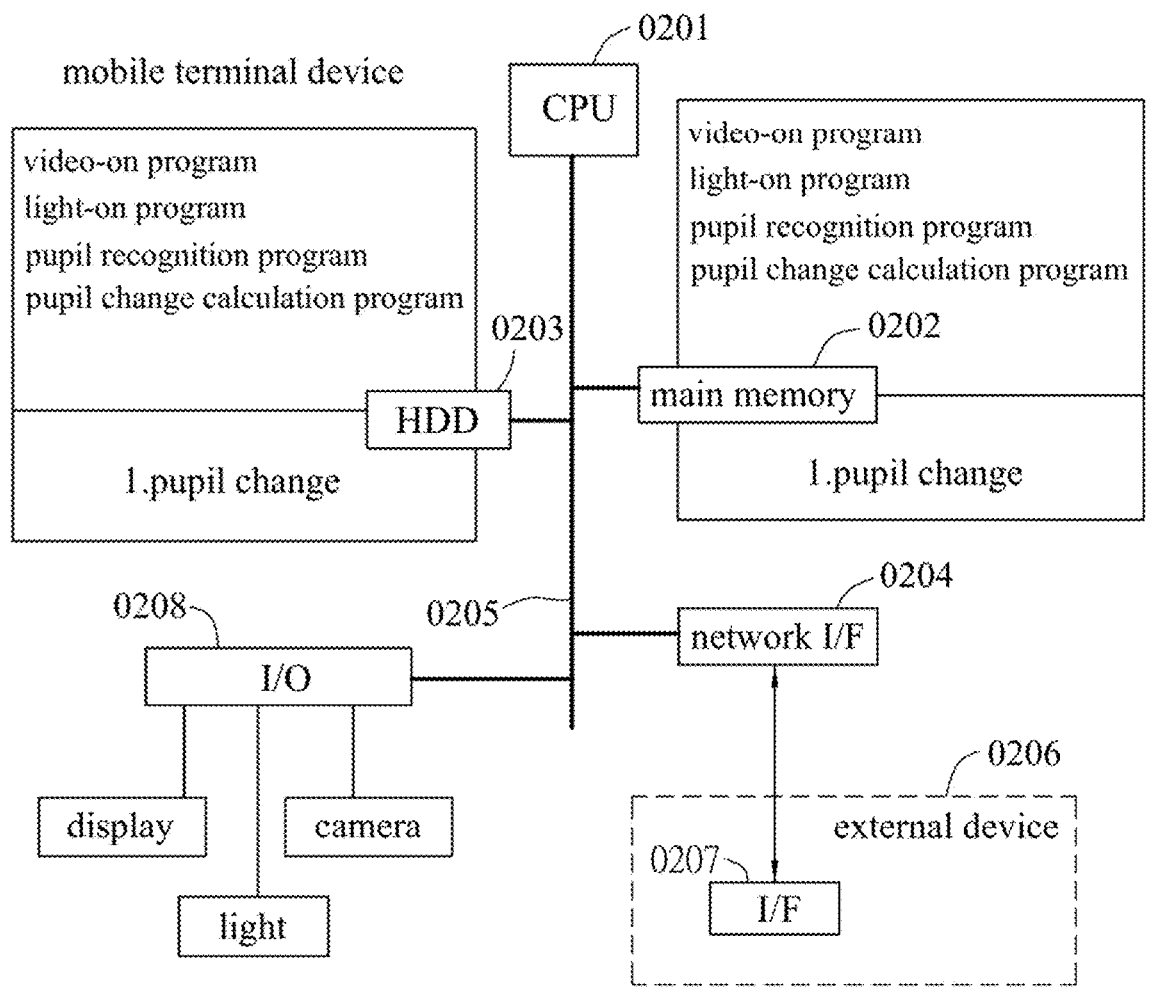
FIG. 2 is a schematic diagram showing the hardware structure of the mobile terminal device according to the first embodiment.

FIG. 2 is a diagram showing an example of a configuration of the mobile terminal device when the above functional components are implemented by hardware. The operation of each hardware component in each process in the present device will be described with reference to this figure.

As shown in the figure, the mobile terminal device of this embodiment includes a "CPU (Central Processing Unit)" (0201) and a "Main Memory" (0202) for performing various arithmetic processing. In addition, the mobile terminal device also includes a "HDD" (0203) and a "Network I/F (network interface)" (0204) for sending and receiving information to and from an "I/F (interface)" (0207) of the external device (0206). The mobile terminal device also includes an "I/O (input/output)" (0208) for sending and receiving information to and from cameras, lights or displays. Then, they are mutually connected by a data communication path such as a "system bus" (0205), and perform transmission and processing of information. The "external device" here usually refers to a manager terminal or a statistical processing device, and it includes, for example, a user terminal or a terminal of a medical institution.

In addition, when the "CPU" reads and executes a program for performing various kinds of processing, the "main memory" provides a work area which is also a work area of the program. Also, a plurality of addresses are allocated to the "main memory", "HDD" or "flash memory" (not shown), respectively, and the program to be executed by the "CPU" are accessed by specifying their addresses so as to exchange data and to perform the processing. The stored program of the present embodiment includes a video-on program for turning on the moving image capturing function of the mobile terminal; a light-on program for turning on the light provided on the image capturing side of the mobile terminal; a pupil recognition program for recognizing pupils of animal eyes from an image that is being captured, wherein the animal eyes include human eyes; and a pupil change calculation program for calculating a pupil change, wherein the pupil change is a change in a dilation level of the recognized pupil over time.

The pupil image of the user obtained by the video-on program of the mobile terminal device is stored in the addresses of the "main memory" and "HDD". Then, in the "CPU" of the mobile terminal device, the time change of the pupil recognized by the logical calculation processing is calculated using the moving image information stored in the "main memory". When recording a captured moving image, the moving image information is stored in the "HDD" in this way. On the other hand, in the case of recognizing and computing photographed pupils in real time, the moving image information will not be stored in the "HDD".

<Process Flow>

Figure 3:
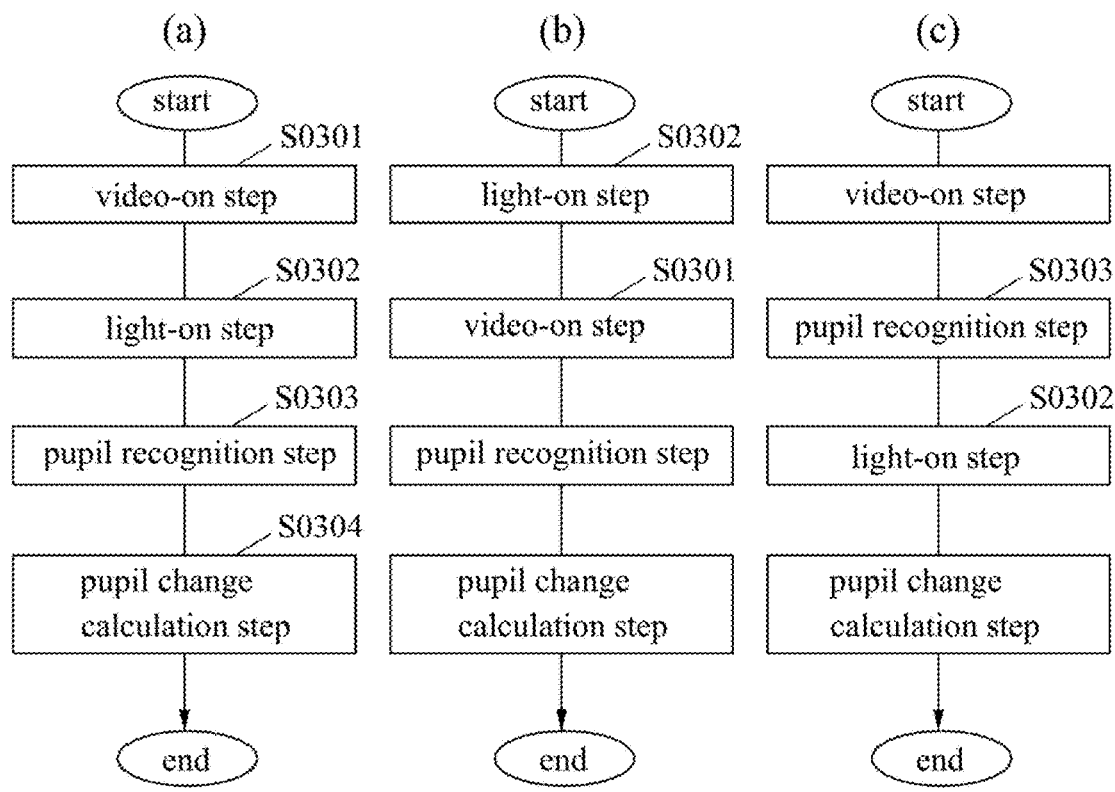
FIG. 3 is a flow chart showing a processing procedure according to the first embodiment.

FIG. 3 is a flowchart showing an example of the processing flow in the mobile terminal device of this embodiment. The following steps may be processing steps of a program recorded on a medium for controlling a computer (mobile terminal).

As shown in (a) of FIG. 3, firstly, the moving image capturing function of the mobile terminal is turned on (S0301). Next, a light disposed at an image capturing side of the mobile terminal is turned on (S0302). Then, a pupil of animal eye including a human eye is recognized from the image that is being captured (S0303). Finally, a pupil change which is a change in a dilation level of the recognized pupil over time is calculated (S0304).

As shown in (b) of FIG. 3, the order of the video-on step (S0301) for turning on the moving image capturing function of the mobile terminal and the light-on step (S0302) for turning on the light disposed at an image capturing side of the mobile terminal may be reversed. That is, firstly, a light disposed at an image capturing side of the mobile terminal is turned on. Next, the moving image capturing function of the mobile terminal is turned on. Then, a pupil of animal eye including a human eye is recognized from the image that is being captured. Finally, a pupil change which is a change in a dilation level of the recognized pupil over time is calculated.

As shown in (c) of FIG. 3, the order of the light-on step (S0302) for turning on the light disposed at an image capturing side of the mobile terminal and the pupil recognition step (S0303) for recognizing the pupil of the animal eye including human eye from an image that is being captured may be reversed. That is, firstly, the moving image capturing function of the mobile terminal is turned on. Next, a pupil of animal eye including a human eye is recognized from the image that is being captured. Then, a light disposed at an image capturing side of the mobile terminal is turned on. Finally, a pupil change which is a change in a dilation level of the recognized pupil over time is calculated.

It is to be noted that the order of the processing flow as described above is the same for the embodiments other than this embodiment.

Also, in order to obtain the time taken until the constricted pupil becomes normal (the original state), the pupil dilation rate, the pupil dilation speed, the pupil dilation acceleration, it may further include a "light-off step" for turning off the light disposed at the image capturing side of the mobile terminal. According to this, more accurate stress level can be realized.

Figure 53:
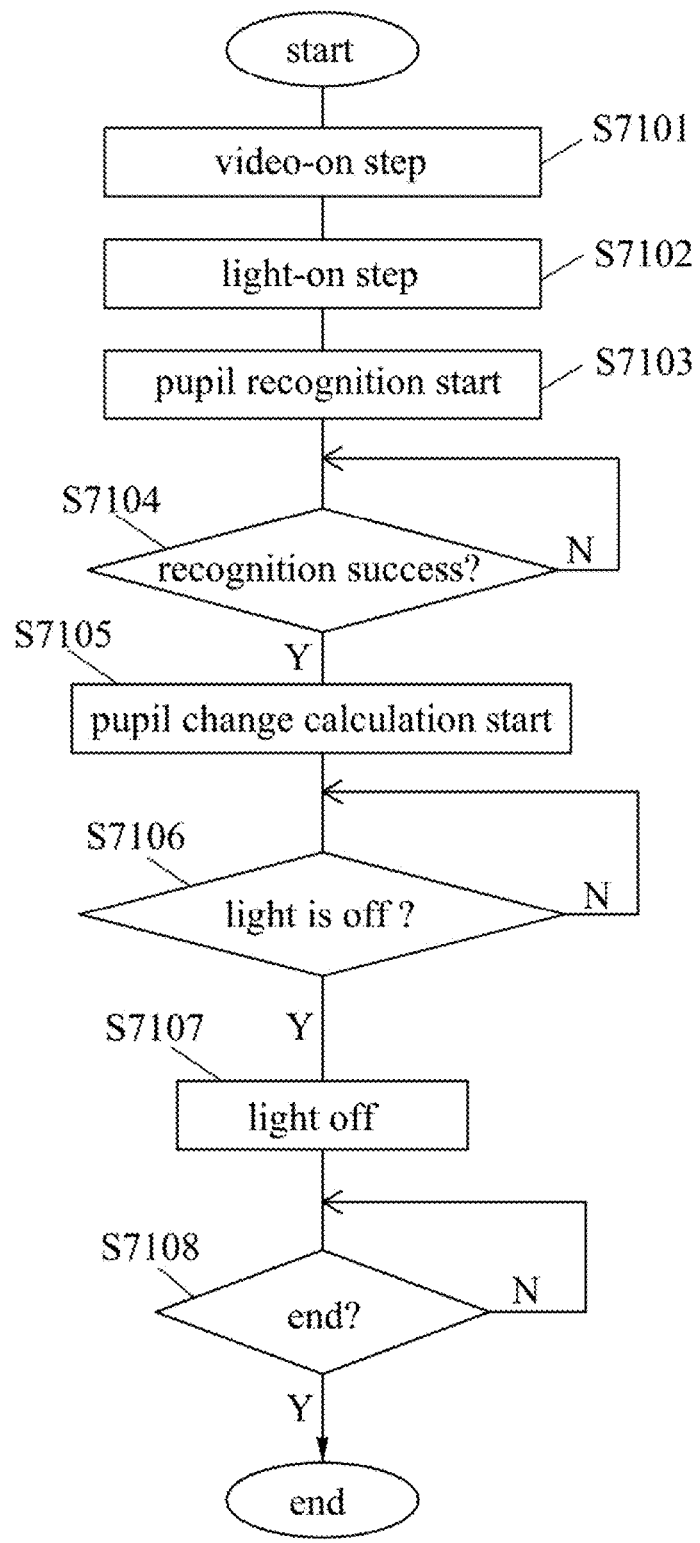
FIG. 53 is a processing flow chart including the light-off step.

FIG. 53 is a diagram showing a processing flow in the case of having a light-off step. First, there are a video-on step (S7101) and a light-on step (S7102). Next, a pupil recognition step (S7103) is performed to start a recognition, whether the pupil recognition is successful or not is confirmed (S7104), and the recognition step is repeated until the pupil recognition is successful. This pupil recognition continues until the whole process is completed. Next, there is a pupil change calculation step (S7105). This pupil change calculation is continued until the whole process is completed. Next, the light-off step is performed to determine whether to turn off the light (S7106). If yes, the light is turned off (S7108), and if no, the processing is continued until yes. It is conceivable that the step to determine whether to turn off the light here is to turn off the light at the time of a predetermined time or when the speed is reduced or stopped below the fixed speed. Considering that there are individual differences in biological reaction such as pupil constriction speed, the timing to turn off the light is not uniform, and it is preferable to set it at the time of stopping the constriction or at a speed equal to or less than a certain speed. Finally, there is a confirmation as to whether or not the whole process is finished. If it is no, the process is continued, and if it is yes, the whole process is ended. The confirmation as to whether or not the whole processing is finished is made yes when a predetermined time elapses, at the time of stopping pupil dilation or at a constant speed or lower, or when returning to the size of the pupil at the time of recognition.

Figure 40:
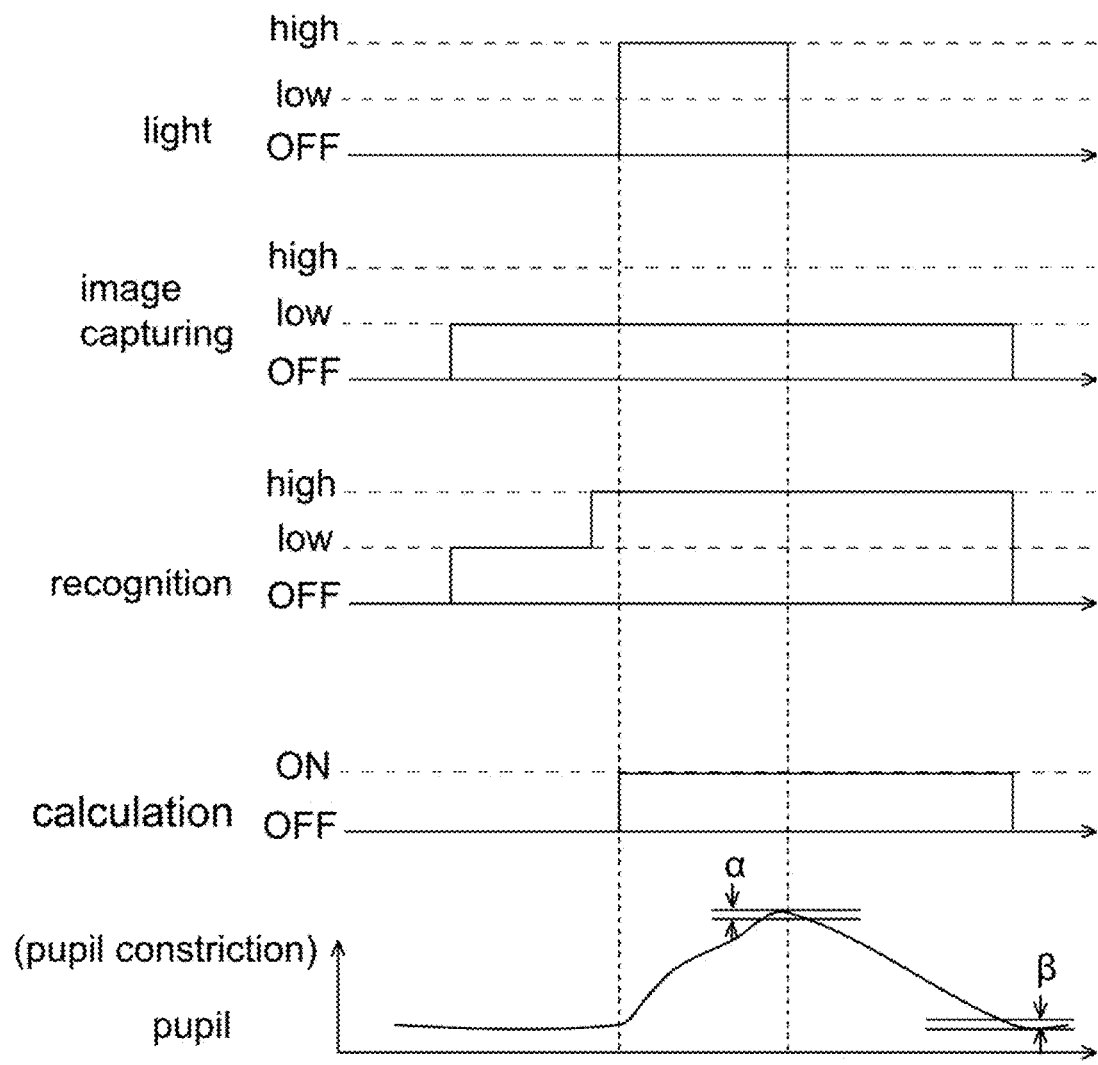
FIG. 40 is an experimental diagram of the processing procedure represented by timing chart according to the first embodiment.

FIG. 40 is a diagram showing an example of a case showing the above steps which are set as in a time chart. When the user turns on the switch (SW), the moving image capturing and the pupil recognition start. Then, at the same time or slightly behind when the recognition is completed and the pupil recognition function turns on (high), the pupil calculation is started. Thereafter, the light turns off when the predetermined time has elapsed, or when the pupil constriction stops or when the speed becomes equal to or less than a predetermined speed (the range indicated by a in the drawing). Then, when the predetermined time has elapsed, or when the pupil constriction is stopped or when the speed becomes equal to or less than a certain speed (the range indicated by β in the drawing), or when the pupil size returns to the size at the time of recognition, the whole process is completed.

Considering the time change of the pupil constriction by using FIG. 40, it is found that the pupil starts constriction while the light is turned on, the pupil starts dilation after the light is turned off, and the pupil dilation stops when a certain degree of the pupil dilation occurs.

In this time chart, for example, there may be a step (High) of automatically tracking only the iris portion and the pupil portion which are important parts in the pupil calculation with respect to moving image capturing. Thus, the pupil calculation can be performed with high accuracy.

Figure 44:
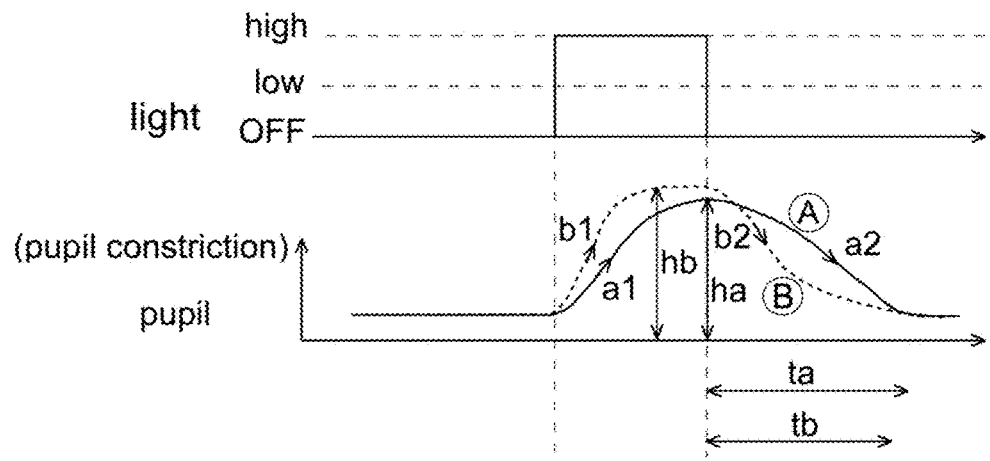
FIG. 44 is a schematic diagram for illustrating the pupil calculation.

FIG. 44 is a diagram for explaining a mode of pupil calculation. Assuming that there are data of A and B as model data, the pupil constriction speed ($a_1$) at the time of lighting the line A, the pupil constriction rate ($h_a$) at the time of minimum pupil, the pupil dilation speed ($a_2$) after the light is turned off, the time ($t_a$) from turning off the light to stopping the pupil dilation, and the likes are measured. Similarly, with respect to the line B, the pupil constriction speed ($b_1$) at the time of lighting, the pupil constriction rate ($h_b$) at the time of minimum pupil, the pupil dilation speed ($b_2$) after the light is turned off, the time ($t_b$) from turning off the light to stopping the pupil dilation, and the likes are measured. In this way, the pupil constriction starts after turning on the light, and the pupil dilation starts after turning off the light. For these two model data, if analysis is carried out on the premise that the faster one of the pupil constriction and pupil dilation is a weaker stress, it is realized that the stress of the model data B is lower than the stress of the model data B.

With the above steps, it is possible to measure the state of stress by objective symptoms having a correlation with stress using the mobile terminal device.

Second Embodiment

<Overview>

In this embodiment, in addition to the configuration of the first embodiment, as a more preferable embodiment, the mobile terminal device further having a function of changing illuminance of a light over time is provided.

Hereinafter, the function of the device, the contents of the hardware in this embodiment, and the processing flow will be described in detail.

<Functional Configuration>

Figure 4:
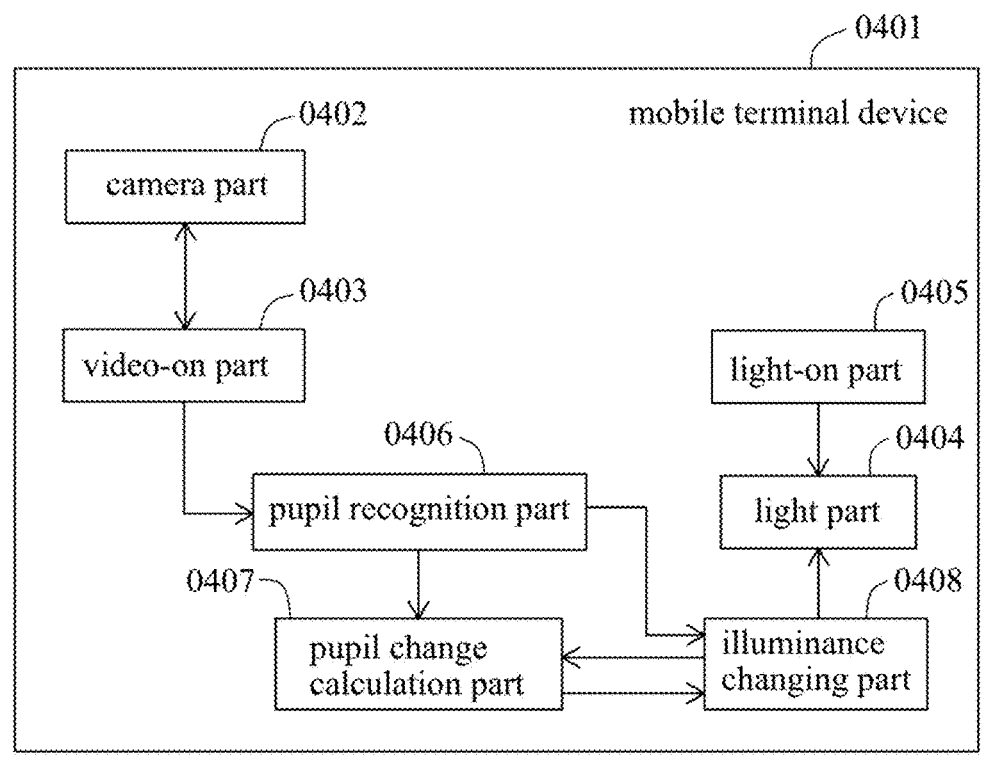
FIG. 4 is a is a functional block diagram of a mobile terminal device according to a second embodiment.

FIG. 4 is a diagram showing an example of functional blocks of the mobile terminal device of this embodiment. As shown in the figure, the mobile terminal device (0401) of the present embodiment includes a camera part (0402), a video-on part (0403), a light part (0404), a light-on part (0405), a pupil recognition part (0406), a pupil change calculation part (0407), and an illuminance changing part (0408). The feature of this embodiment lies in the content of the illuminance changing part. Therefore, the functional configuration of the illuminance changing part will be mainly described. Since the other functions are the same as those described above, the description thereof will be omitted.

The "illuminance changing part" (0406) functions to change the illuminance of the light turned on by the light-on part with the lapse of time. For example, in order to recognize the pupil, it is necessary to apply light to the pupil, but on the other hand, when the illuminance of the light is too strong, a pupil response to light occurs. Then, the change starts before the pupil recognition part recognizes the pupil, and the accuracy of the calculation is impaired. Therefore, by the action of the illuminance changing part, for example, the light with a weaker illuminance is applied until the pupil recognition. Then, from the point of recognizing the pupil, utilizing the light of illuminance that causes a pupil response to light is applied. Thus, a high accuracy calculation result can be obtained.

Furthermore, it is desirable to perform the pupil change in a dark room. The operation of the illuminance changing part enables the operation using the minimum amount of light, and it becomes possible to operate it with a mobile terminal in a darkroom.

<Hardware Configuration>

Figure 5:
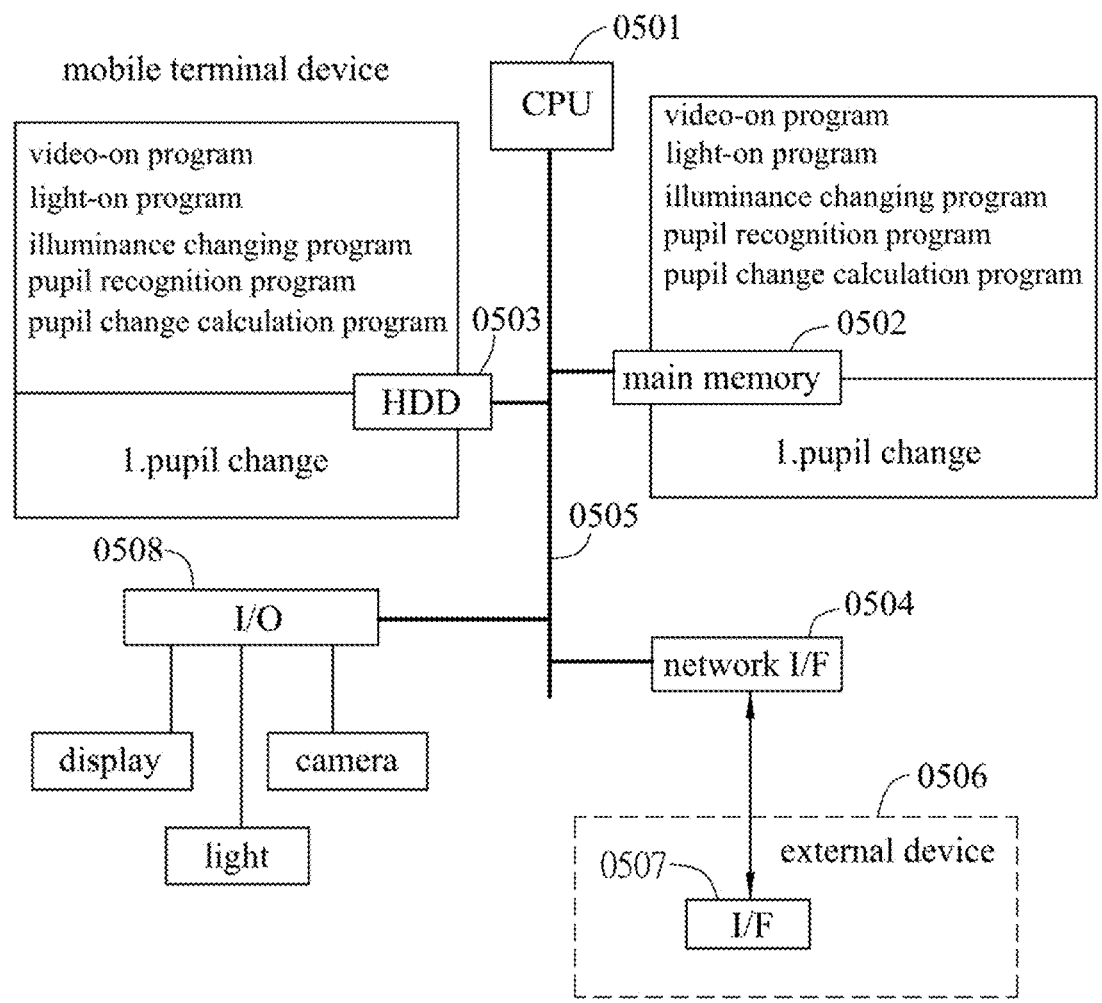
FIG. 5 is a schematic diagram showing the hardware structure of the mobile terminal device according to the second embodiment.

FIG. 5 is a diagram showing an example of the configuration of the mobile terminal device, and the functional components are implemented by hardware. The mobile terminal device includes a CPU (Central Processing Unit) (0501), a "main memory" (0502), an "HDD" (0503), a "network I/F" (0504), an "I/O" (0508), and a "system bus" (0505), and connects to an external device (0506), which has an "I/F" (0507).

Using these figures, the characteristic parts of this embodiment among the hardware components for each processing in the present device will be described, and the other parts are similar to the description of the above-mentioned embodiment.

In the mobile terminal device of this embodiment, an illuminance change program is further added as the content of the program stored in the "main memory".

Therefore, the illuminance of the light turned on by using the light-on program in the operation of "CPU" will change with the lapse of time.

<Processing Flow>

Figure 6:
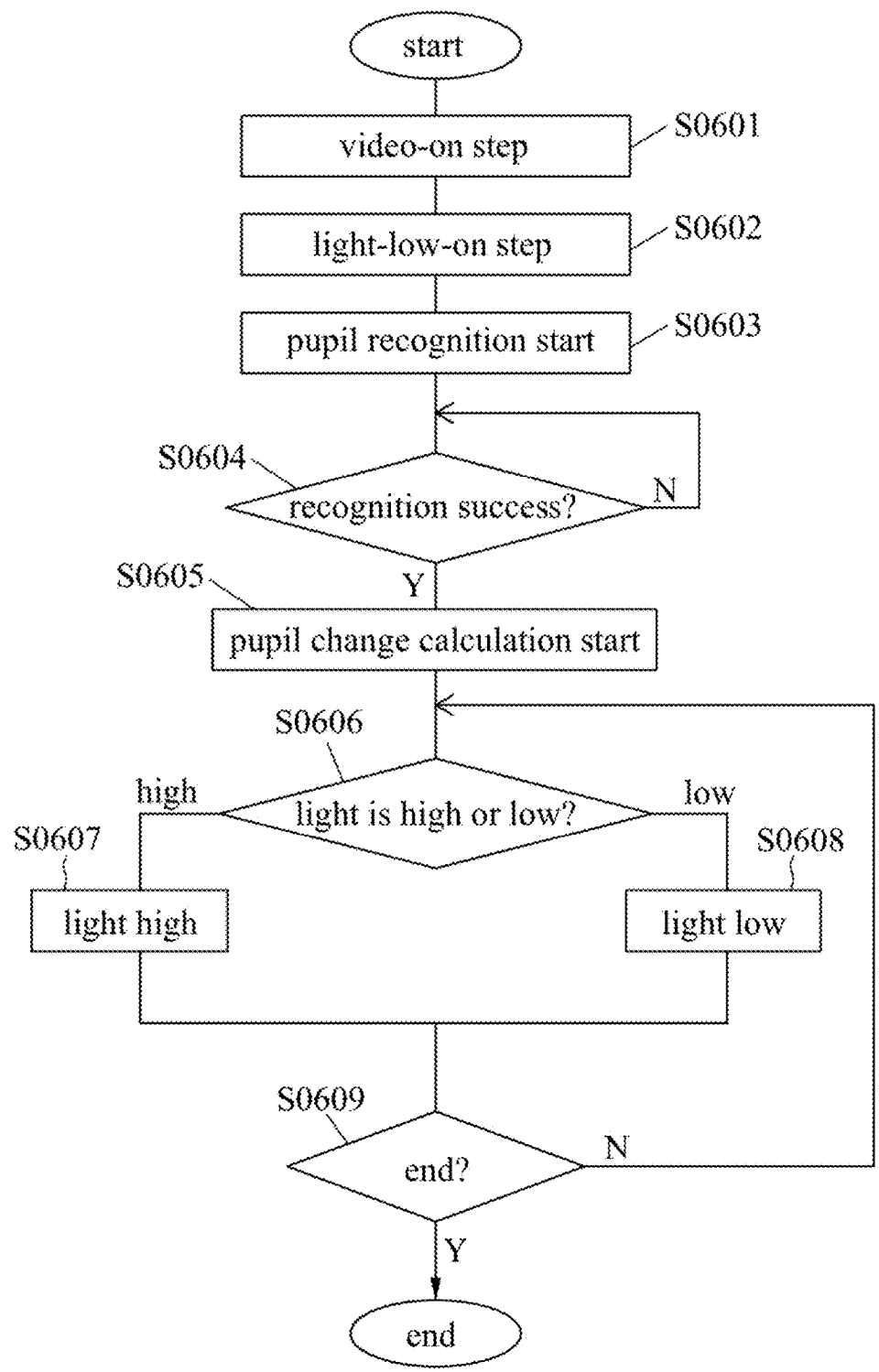
FIG. 6 is a flow chart showing a processing procedure according to the second embodiment.

FIG. 6 is a flow chart showing an example of the processing flow in the mobile terminal device of this embodiment. The following steps may be processing steps of a program recorded on a medium for controlling a computer (mobile terminal).

First, a video-on step (S0601) and a light-low-on step (S0602) are provided. Next, a recognition starts as the pupil recognition step (S0603), and it is confirmed whether the pupil recognition is successful (S0604). The recognition step is repeated until the pupil recognition is successful. This pupil recognition continues until the whole process is completed.

Next, a pupil change calculation step (S0605) is provided. The pupil change calculation is continued until the whole process is completed. Next, in a content of the illuminance changing step, there is a confirmation as to whether the light is set to "high" or "low" (S0606). If it is "high", the process for making the light high (S0607) is performed. If it is "low", the process for making the light low (S0608) is performed. The confirmation as to whether the light is to be set to "high" or "low" is, for example, to make the light high at the first time, and then to make the light low after the light is turned on for a predetermined time or when the pupil constriction stops or the pupil constriction speed is lower than a certain speed. Considering individual differences in biological reaction such as the pupil constriction speed, the timing of turning the light low is not uniform, and it is preferable to set it at the time when the pupil constriction stops or the pupil constriction speed is lower than a certain speed.

Finally, a confirmation step is to determine whether the whole process is finished or not. If the whole process is not finished, the process returns to the confirmation step (S0606) to determine whether the light is set to "high" or "low", and if the whole process is finished, the whole process is ended. The confirmation step to determine whether the whole process is finished or not is made YES when a predetermined time elapses, when the pupil dilation stops or the pupil dilation speed is equal to or lower than a certain value, or when the pupil size returns to the size of pupil at the time of recognition.

The processing in this embodiment has an illuminance changing step. The "illuminance changing step" is a step of changing the illuminance of the light turned on by the light-on part with the lapse of time.

Figure 43:
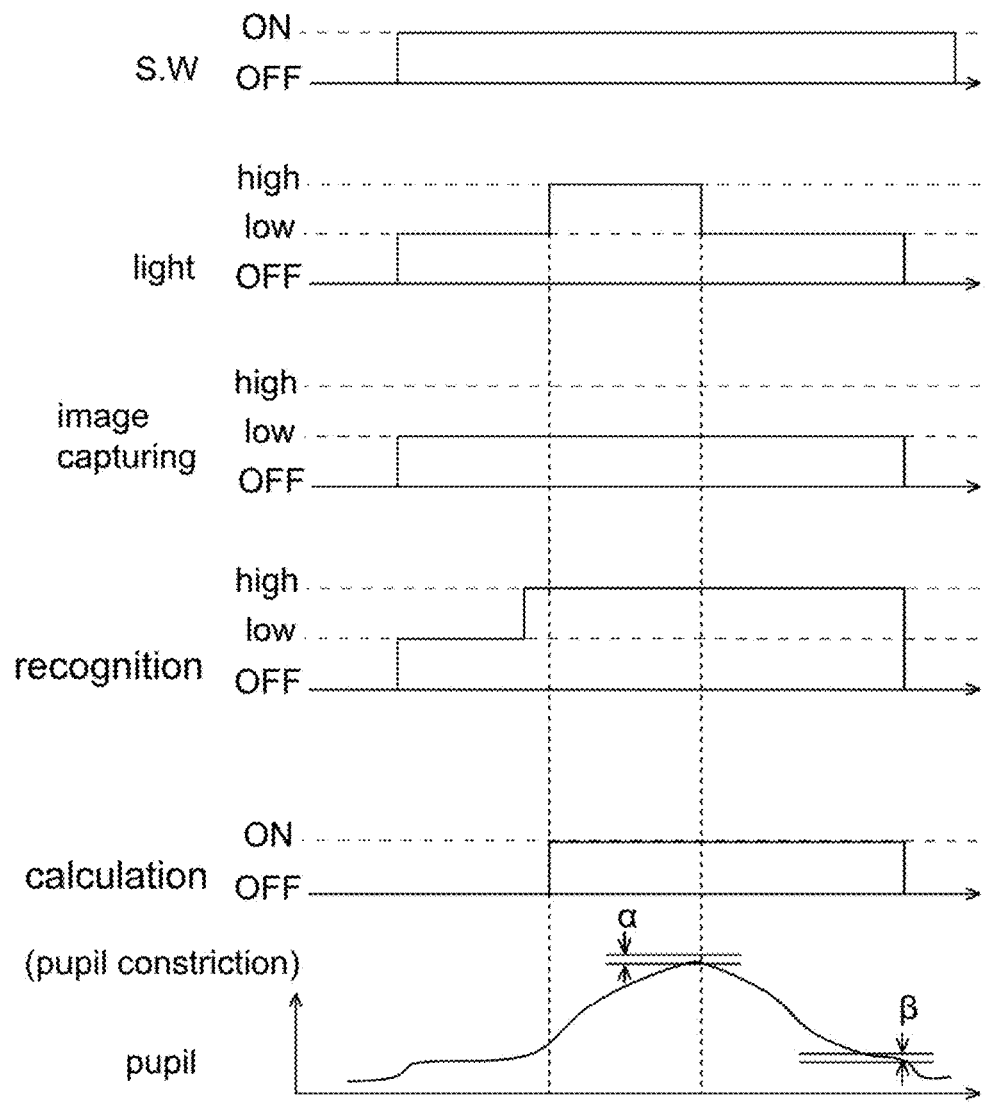
FIG. 43 is an experimental diagram of the processing procedure represented by timing chart according to the second embodiment.

FIG. 43 is a diagram showing an example of a case where the above steps are set as time charts. When the user turns on the switch (SW), the moving image capturing, the light and the pupil recognition are enabled. Then, at the same time or slightly behind when the recognition is completed and the pupil recognition function turns on (high), the pupil calculation is started and the illuminance increases. Thereafter, the light is set low when the predetermined time elapses, when the pupil constriction stops, or when the pupil constriction speed is equal to or less than a certain speed (the range indicated by α in the drawing). Then, when the predetermined time elapses, when the pupil dilation stops, or when the pupil dilation speed is equal to or less than a certain speed (the range indicated by β in the drawing), the whole process is completed.

Figure 54:
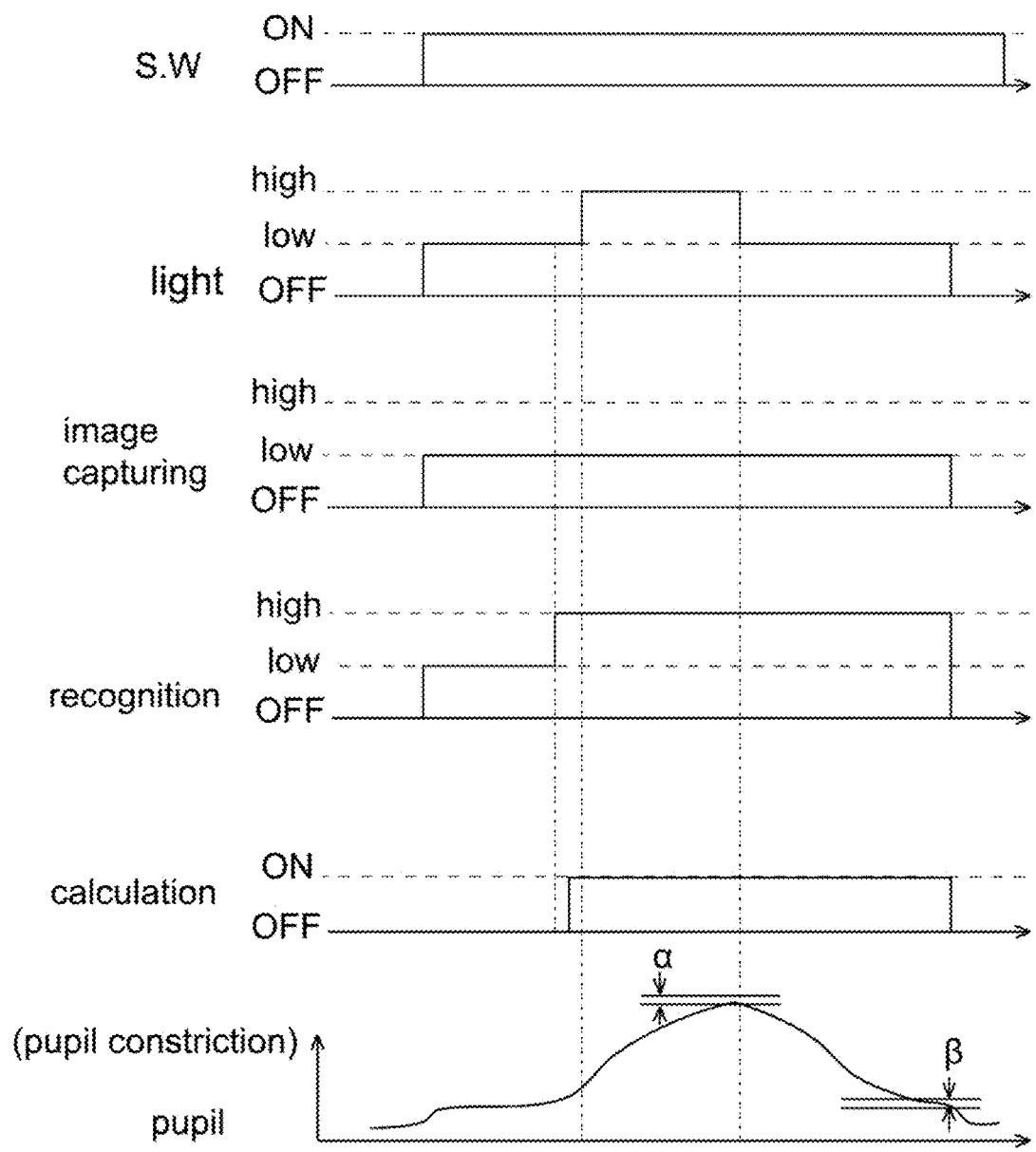
FIG. 54 is a timing chart of the ending processing that the pupil size returns to recognition.

Next, FIG. 54 is a diagram showing a time chart for enabling the configuration to end the process when the pupil size returns to the size at the time of recognition. When the user turns on the switch (SW), the moving image capturing, the light and the pupil recognition are enabled. Then, at the same time or slightly behind when the recognition is completed and the pupil recognition function becomes high, the illuminance of the light increases after computing the pupil in the original state. Thereafter, the light is set low when the predetermined time elapses, when the pupil constriction stops, or when the pupil constriction speed is equal to or less than a certain speed (the range indicated by a in the drawing). Then, when the predetermined time has elapsed, when the pupil dilation stops, when the pupil dilation speed is equal to or less than a certain speed (the range indicated by β in the drawing), or when the pupil size returns to the size at the time of recognition, the whole process is completed. As described above, it is possible to calculate the pupil in the original state by performing the calculation before the light illuminance becomes high, and to terminate the whole process when it is coincidence with the calculation result.

Considering the transition of the pupil constriction using FIG. 43, the pupil constriction begins slowly while the light is turned on and set to low. When the light goes high, the pupil constriction speed accelerates, and when the light goes low again, the pupil dilation starts. The pupil dilation stops when the pupil dilation reaches a certain level.

As described in the functional configuration, with such a processing flow, it is possible to obtain a calculation result with high accuracy and a mobile terminal that can be used in a darkroom.

Third Embodiment

<Overview>

This embodiment is a more preferable embodiment providing a mobile terminal device having a function of evaluating the stress level in addition to any one of the configurations of the first and second embodiments.

Hereinafter, the function of the device, the contents of the hardware, and the processing flow of this embodiment will be described in detail.

<Functional Configuration>

Figure 7:
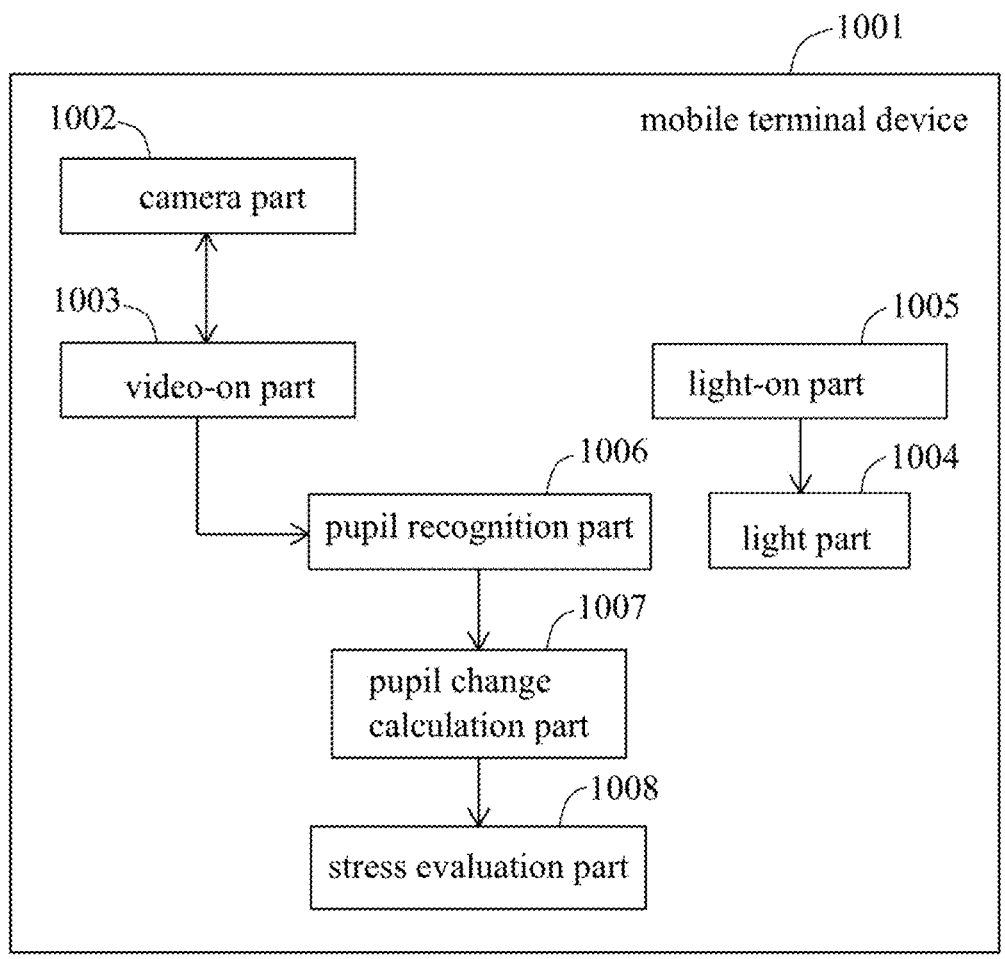
FIG. 7 is a is a functional block diagram of a mobile terminal device according to a third embodiment.

FIG. 7 is a diagram showing an example of functional blocks of the mobile terminal device of this embodiment. As shown in the figure, the mobile terminal device (1001) of this embodiment includes a camera part (1002), a video-on part (1003), a light part (1004), a light-on part (1005), a pupil recognition part (1006), a pupil change calculation part (1007), and a stress evaluation part (1008). The feature of the present embodiment lies in the content of the stress evaluation part. Therefore, the functional configuration of the stress evaluation part will be mainly described. Since the other functions are the same as those described above, the description thereof will be omitted.

The "stress evaluation part" functions to evaluate the stress level based on the pupil change calculated by the pupil change calculation part and obtain the stress evaluation result. For example, based on data such as the diameter value and area value calculated by the pupil change calculation part, the time required until the pupil becomes minimum, the pupil constriction rate, the pupil constriction speed, and the pupil constriction acceleration, the stress level can be calculated.

The stress level may be represented by a numerical value with % or the likes, or a stepwise method such as large, medium and small. In addition, it is also possible to be represented by a ratio comparing with the stress level of the previous day, the comparison value of the maximum value/ the minimum value, or the likes. Furthermore, when the correlation with sleeping time or work intensity can be seen, the reason causing the stress can be derived based on the correlation.

Figure 49:
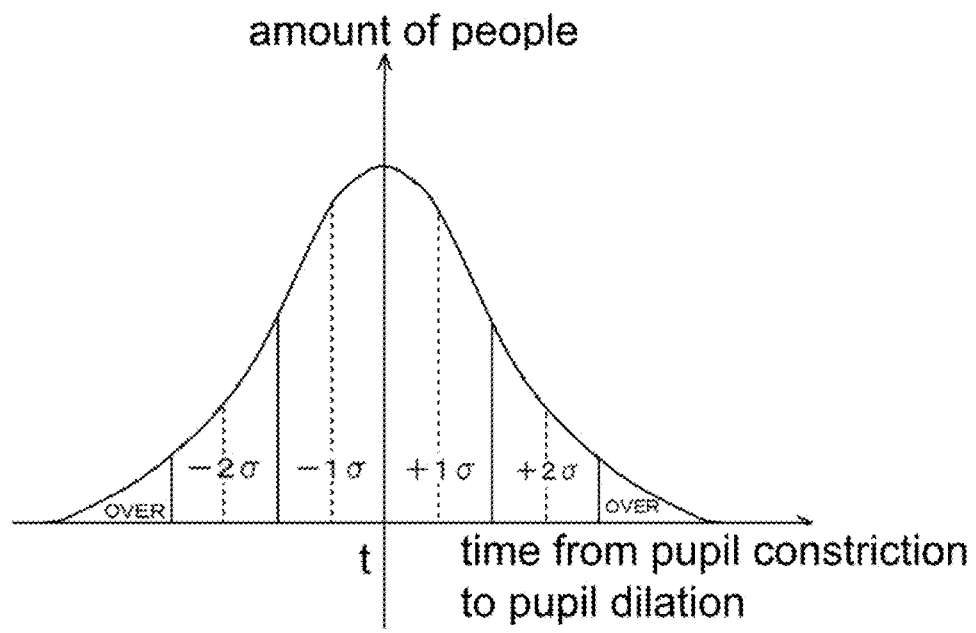
FIG. 49 is a schematic diagram showing the stress evaluation method.

FIG. 49 is a diagram showing a stress evaluation method. When the statistical data of 2000 people becomes a curve as shown in the figure, it can be considered that the stress evaluation is indicated by measuring the distance from the median value t with respect to the time from pupil constriction to pupil dilation. For example, in FIG. 49, in the zone "+1σ", the point close to the median value t represents "normal", and the point away from the median value t represents a "weak stress". In the zone "+2σ", the point close to the median value t represents a "medium stress", and the point away from the median value t represents a "strong stress". Furthermore, the zone "over", which is farther then the zone "+2σ", represents a "very strong stress".

Furthermore, when the stress level exceeds a certain level, it may be provided with a function of informing with an alarm sound or the like. In addition, information sharing between parents and children or working users/workers is promoted. For example, when a child or an employee has a certain stress level, it is desirable to provide a system for sending a notification about the stress level to parents or users (companies, etc.).

Furthermore, it is preferable that there is a stress evaluation list output part for outputting the stress evaluation result as a list. As a method of list display, the graphs, tables, calendars, and the likes can be considered.

FIG. 37 is a diagram showing the contents of the statistical information output by the stress evaluation result output part. The stress evaluation results for each date are listed in a calendar format. In this way, it is possible to list the user's stress level and to know the characteristics of the stress level for each day of the week. In addition to this, for example, information such as pupil change information and measurement conditions may be written in the date column. For example, if it is indicated together with information such as the brightness of the measured place, the measurement time, the time before and after meals, the sleeping time of the previous day, and the presence or absence and intensity of work on the measurement day, the user can realize the reason causing his/her stress and this can help the user to relax the stress in life.

With this function, the user can understand the stress level at a glance by numerical values, marks, and the likes. Also, if the reason can be found, we can make use of it for usual life. In addition, by providing an alarm function and having a notification function to others, it leads to preventing traffic accidents and the likes that are caused by stress.

Furthermore, in the configuration added to the third embodiment, it is desirable that there is a list output part that outputs the obtained body composition data and stress evaluation results as a list. By displaying in a list as described above, it is possible to know at a glance the element which is affecting stress in the body composition data at a glance with respective to the pupil change.

<Hardware Configuration>

Figure 8:
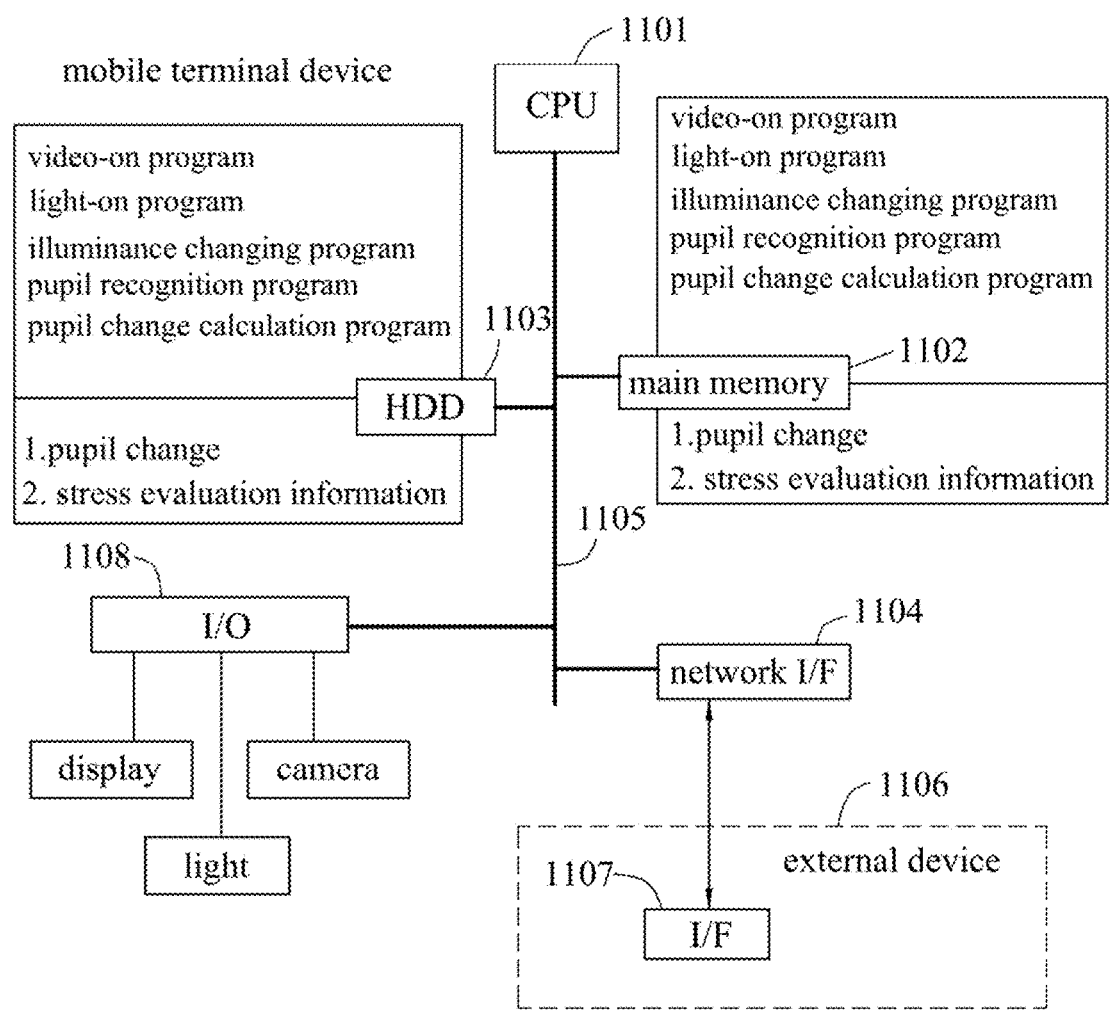
FIG. 8 is a schematic diagram showing the hardware structure of the mobile terminal device according to the third embodiment.

FIG. 8 is a diagram showing an example of the configuration of the mobile terminal device when the above functional components are implemented as hardware. The mobile terminal device includes a CPU (central processing unit) (1101), a main memory (1102), an HDD (1103), a network I/F (1104), an I/O (1108), and a "system bus" (1105), and the external device (1106) includes an "I/F" (1107).

Using these figures, the characteristic parts of this embodiment among the respective hardware components of each processing in the present device will be described, and the other parts are similar to the description of the above-mentioned embodiments.

In the mobile terminal device of this embodiment, a stress evaluation program is added as the content of the program stored in the "main memory".

Therefore, in the operation of the "CPU", the stress level is evaluated based on the pupil change obtained by the pupil change calculation program.

<Processing Flow>

Figure 9:
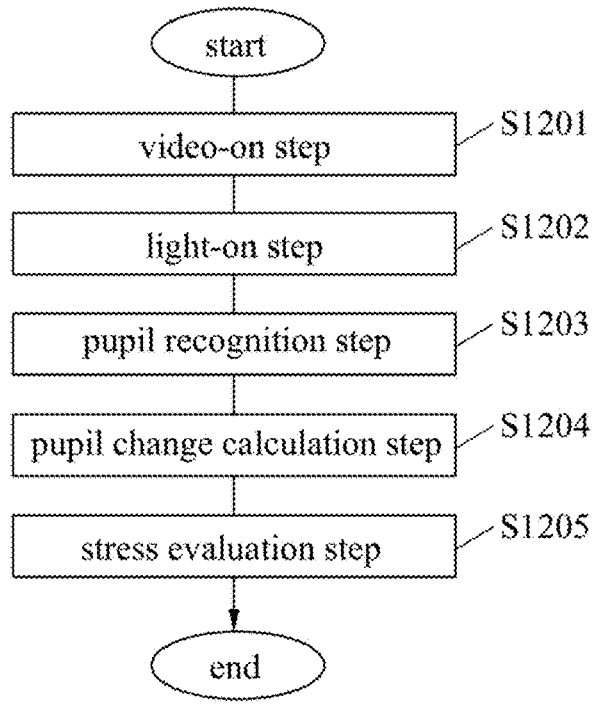
FIG. 9 is a flow chart showing a processing procedure according to the third embodiment.

FIG. 9 is a flow chart showing an example of the processing flow of the mobile terminal device of this embodiment. The following steps may be processing steps of a program recorded on a medium for controlling a computer (mobile terminal).

A video-on step (S1201), a light-on step (S1202), a pupil recognition step (S1203), a pupil change calculation step (S1204), and a stress evaluation step (S1205) are included. Using these diagrams, the characteristic parts of this embodiment among the flow of each processing in the present device will be described, and the other parts are the same as the description of the above-mentioned embodiments.

In the processing in this embodiment, a stress evaluation step is included. The "stress evaluation step" is a step of obtaining a stress evaluation result by evaluating the stress level based on the pupil change calculated by the pupil change calculation step.

As described in the functional configuration, the stress level may be represented by a numerical value with % and the likes, or a stepwise method such as large, medium and small. In addition, it is also possible to be represented by a ratio comparing with the stress level of the previous day, the comparison value of the maximum value/the minimum value, or the likes. Furthermore, when the correlation with sleeping time or work intensity can be seen, the reason causing the stress can be derived based on the correlation.

Furthermore, when the stress level exceeds a certain level, it may be provided with a step of informing with an alarm sound or the like. In addition, information sharing between parents and children or working users/workers is promoted. For example, when a child or an employee has a certain stress level, it is desirable to provide a system for sending a notification about the stress level to parents or users (companies, etc.).

Furthermore, it is preferable that there is a stress evaluation list output step for outputting the stress evaluation result as a list. As a method of list display, the graphs, tables, calendars, and the likes can be considered.

With this processing flow, the user can understand the stress level at a glance by numerical values, marks, and the likes. Also, if the reason can be found, we can make use of it for usual life. In addition, by providing an alarm function and having a notification function to others, it leads to preventing traffic accidents and the likes that are caused by stress.

Furthermore, in the configuration added to the third embodiment, it is desirable that there is a list output step that outputs the obtained body composition data and stress evaluation results as a list. By displaying in a list as described above, it is possible to know at a glance the element which is affecting stress in the body composition data at a glance with respective to the pupil change.

Fourth Embodiment

<Overview>

In this embodiment, in addition to any one of the configurations of the first, second and third embodiments, as a more preferable embodiment, a mobile terminal device having a function of transmitting a pupil change to a predetermined address is provided.

Hereinafter, the function of the device, the contents of the hardware, and the processing flow of this embodiment will be described in detail.

<Functional Configuration>

Figure 10:
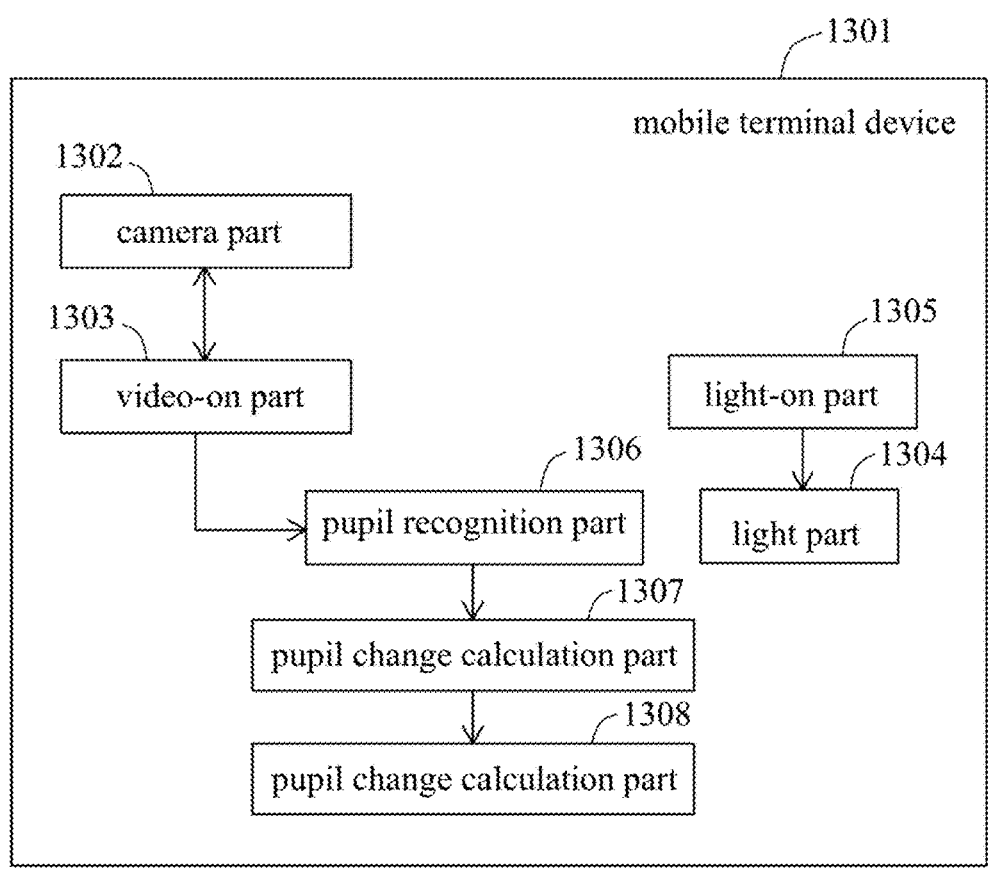
FIG. 10 is a is a functional block diagram of a mobile terminal device according to a fourth embodiment.

FIG. 10 is a diagram showing an example of functional blocks of the mobile terminal device of this embodiment. As shown in the figure, the mobile terminal device (1301) of this embodiment includes a camera part (1302), a video-on part (1303), a light part (1304), a light-on part (1305), a pupil recognition part (1306), a pupil change calculation part (1307), and a pupil change transmission part (1308). The feature of the present embodiment lies in the content of the pupil change transmission part. Therefore, the functional configuration of the pupil change transmission part will be mainly described. Since the other functions are the same as those described above, the description thereof will be omitted.

The "pupil change transmission part" functions to transmit the pupil change calculated by the pupil change calculation part to a predetermined address. For example, pupil change information is transmitted to the HDD or the main memory which is a storage area of the statistical processing device for performing statistical processing, for example, of the external device.

Further, in addition to these, when a stress evaluation is made in an external device, it is desirable to have a configuration in which a stress evaluation result is transmitted from the external device. Then, in the mobile terminal device, it is desirable to have a stress evaluation result receiving part.

In addition, countermeasure introduction information is held in association with a stress evaluation value in an external device. In the case where the stress evaluation value is high, for example, proposals to eliminate factors causing stress or introduction of hospitals/stores and the likes may be received.

<Hardware Configuration>

Figure 11:
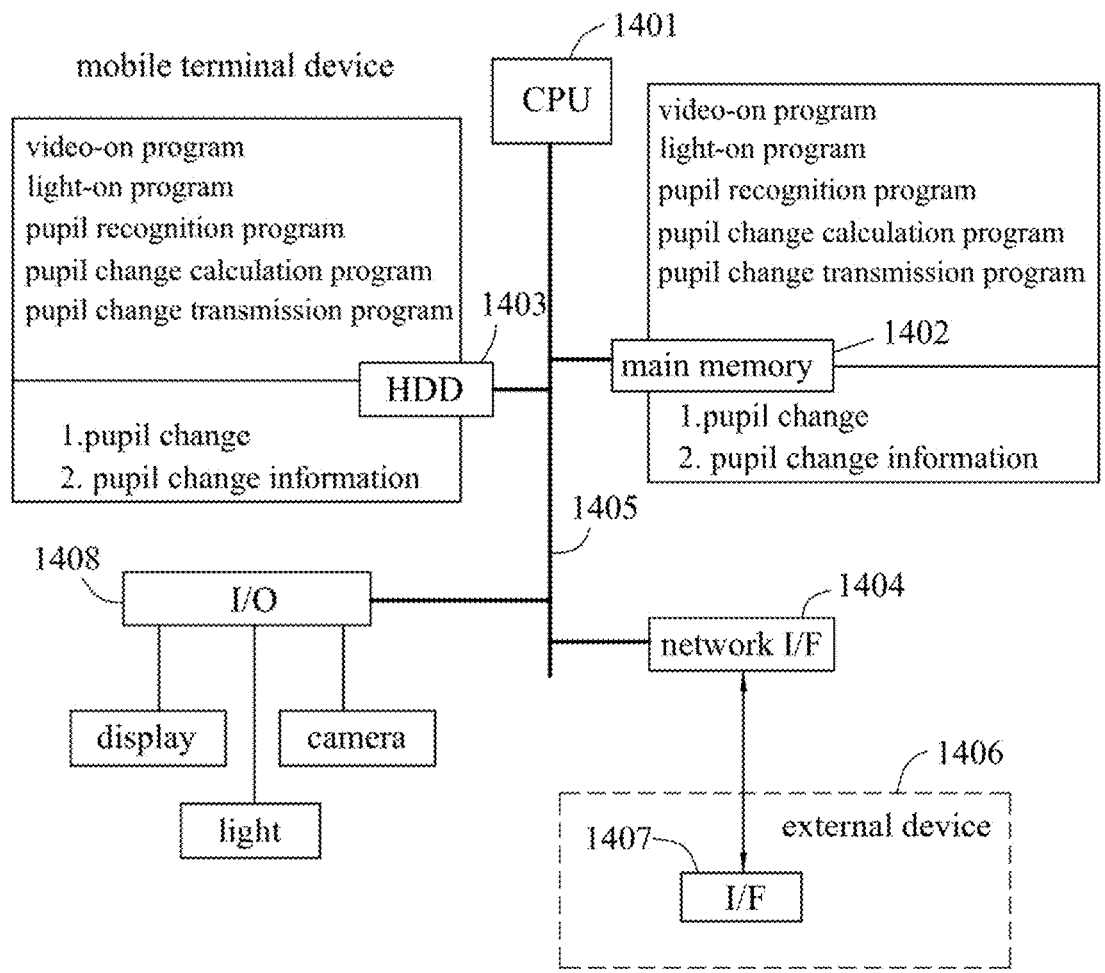
FIG. 11 is a schematic diagram showing the hardware structure of the mobile terminal device according to the fourth embodiment.

FIG. 11 is a diagram showing an example of the configuration of the mobile terminal device when the above functional components are implemented as hardware. The mobile terminal device includes a CPU (central processing unit) (1401), a main memory (1402), an HDD (1403), a network I/F (1404), an I/O (1408), and a "system bus" (1405), and the external device (1106) includes an "I/F" (1107).

Using these figures, the characteristic parts of this embodiment among the respective hardware components of each processing in the present device will be described, and the other parts are similar to the description of the above-mentioned embodiments.

In the mobile terminal device of this embodiment, a pupil change transmission program is added as the content of the program stored in the "main memory".

Therefore, in the operation of the "CPU", the pupil change information obtained by the pupil change calculation program is stored in, for example, the "HDD" or "main memory" of the mobile terminal device, or the main memory or HDD of the external device or a statistical processing device (not shown).

<Processing Flow>

Figure 12:
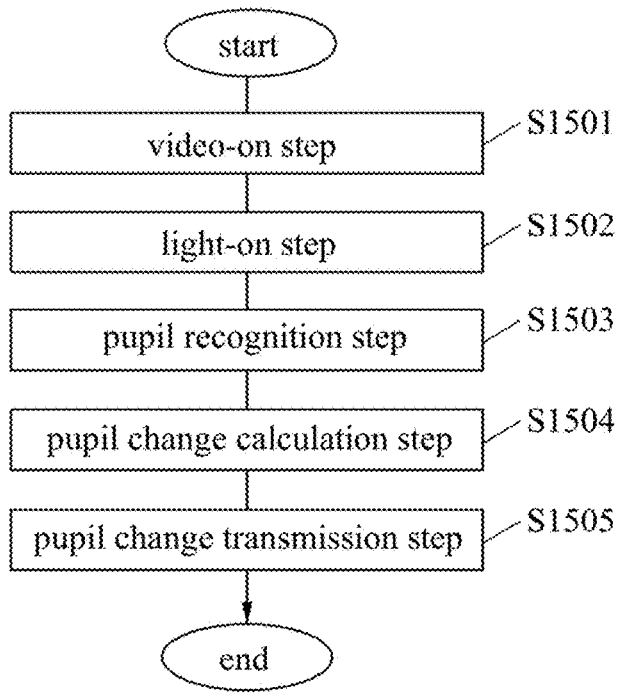
FIG. 12 is a flow chart showing a processing procedure according to the fourth embodiment.

FIG. 12 is a flow chart showing an example of the processing flow of the mobile terminal device of this embodiment. The following steps may be processing steps of a program recorded on a medium for controlling a computer (mobile terminal).

A video-on step (S1501), a light-on step (S1502), a pupil recognition step (S1503), a pupil change calculation step (S1504), and a pupil change transmission step (S1505) are included. Using these diagrams, the characteristic parts of this embodiment among the flow of each processing in the present apparatus will be described, and the other parts are the same as the description of the above-mentioned embodiments.

In the processing of this embodiment, a pupil change transmission step is included. The "pupil change transmission step" is a step of transmitting the pupil change calculated by the pupil change calculation step to a predetermined address. As described in the functional configuration, the transmission destination may be the mobile terminal device or a statistical processing device.

Thus, it is possible to save the required storage area of the mobile terminal device for accumulating the pupil change information. Also, by implementing the statistical processing on a device other than the mobile terminal, the load on the mobile terminal device can be reduced.

Fifth Embodiment

<Overview>

In this embodiment, in addition to any one of the configurations of the third and fourth embodiments, as a more preferable embodiment, a mobile terminal device having a function of transmitting a stress evaluation result to a predetermined address is provided.

Hereinafter, the function of the device, the contents of the hardware, and the processing flow of this embodiment will be described in detail.

<Functional Configuration>

Figure 13:
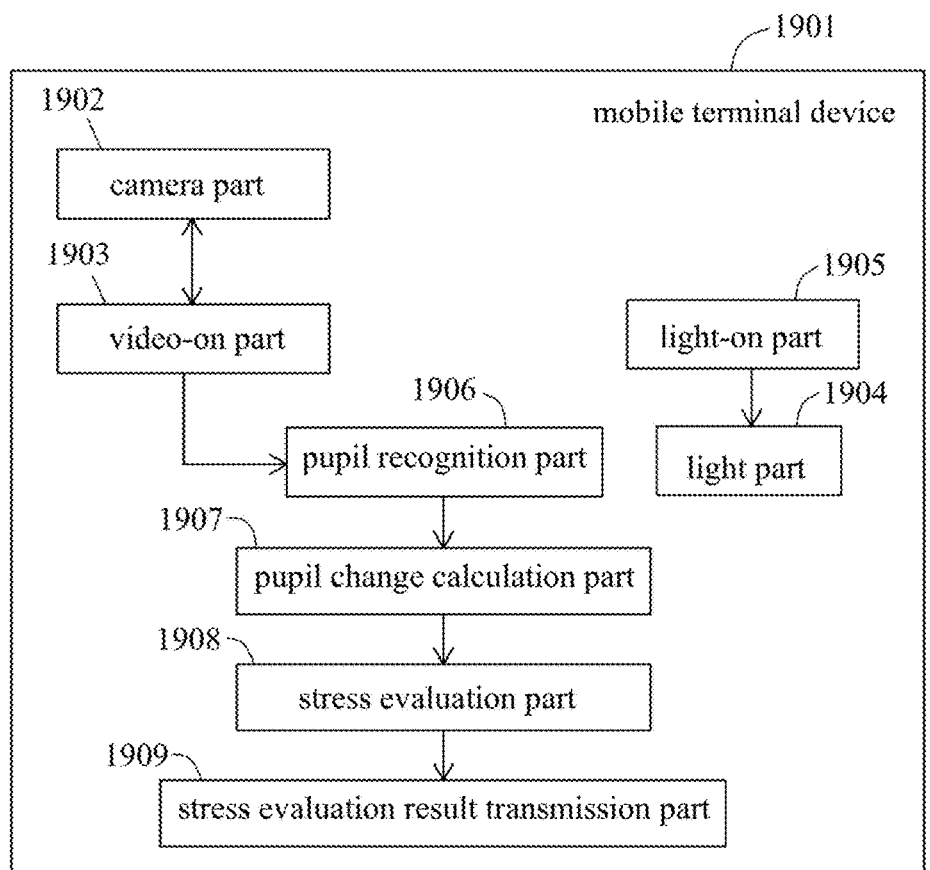
FIG. 13 is a is a functional block diagram of a mobile terminal device according to a fifth embodiment.

FIG. 13 is a diagram showing an example of functional blocks of the mobile terminal device of this embodiment. As shown in the figure, the mobile terminal device (1901) of this embodiment includes a camera part (1902), a video-on part (1903), a light part (1904), a light-on part (1905), a pupil recognition part (1906), a pupil change calculation part (1907), a stress evaluation part (1908), and a stress evaluation result transmission part (1909). The feature of the present embodiment lies in the content of the stress evaluation result transmission part. Therefore, the functional configuration of the stress evaluation result transmission part will be mainly described. Since the other functions are the same as those described above, the description thereof will be omitted.

The "stress evaluation result transmission part" functions to transmit the stress evaluation result obtained by the stress evaluation part to a predetermined address. For example, a stress evaluation is transmitted to a predetermined address of the HDD or the main memory of the mobile terminal device. Alternatively, the stress evaluation information is transmitted to the HDD or main memory, which is a storage area of the statistical processing device for statistical processing. As a result, the stress evaluation information can be accumulated.

<Hardware Configuration>

Figure 14:
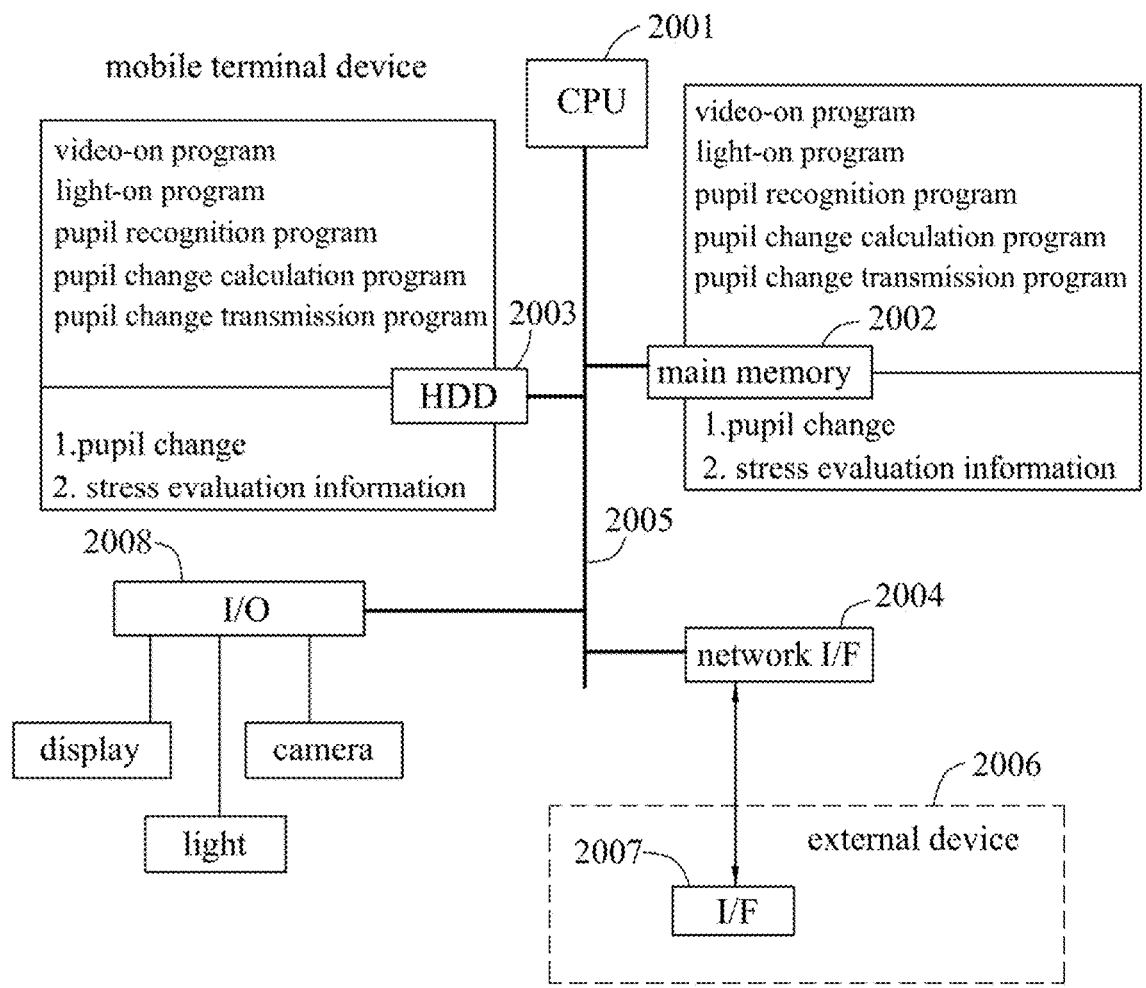
FIG. 14 is a schematic diagram showing the hardware structure of the mobile terminal device according to the fifth embodiment.

FIG. 14 is a diagram showing an example of the configuration of the mobile terminal device when the above functional components are implemented by hardware. The mobile terminal device includes a CPU (central processing unit) (2001), a main memory (1402), an HDD (1403), a network I/F (1404), an I/O (1408), and a "system bus" (1405), and the external device (1406) includes an "I/F" (1407).

Using these figures, the characteristic parts of this embodiment among the respective hardware components of each processing in the present device will be described, and the other parts are similar to the description of the above-mentioned embodiments.

In the mobile terminal device of this embodiment, a stress evaluation result transmission program is added as the content of the program stored in the "main memory".

Therefore, in the operation of the "CPU", the stress evaluation information obtained by the stress evaluation program is stored in, for example, the "HDD" or "main memory" of the mobile terminal device, or the main memory or HDD of the external device or a statistical processing device (not shown).

<Processing Flow>

Figure 15:
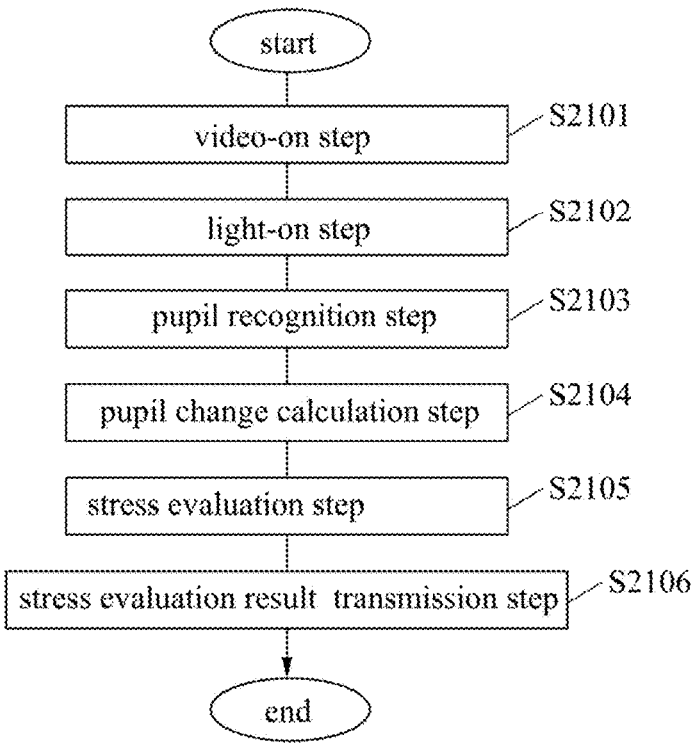
FIG. 15 is a flow chart showing a processing procedure according to the fifth embodiment.

FIG. 15 is a flow chart showing an example of the processing flow of the mobile terminal device of this embodiment. The following steps may be processing steps of a program recorded on a medium for controlling a computer (mobile terminal).

A video-on step (S2101), a light-on step (S2102), a pupil recognition step (S2103), a pupil change calculation step (S2104), a stress evaluation step (S2105) and a stress evaluation result transmission step (S2106) are included. Using these diagrams, the characteristic parts of this embodiment among the flow of each processing in the present apparatus will be described, and the other parts are the same as the description of the above-mentioned embodiments.

In the processing of this embodiment, a stress evaluation result transmission step is included. The "stress evaluation result transmission step" is a step of transmitting the stress evaluation result obtained by the stress evaluation step to a predetermined address.

Thus, it is possible to save the required storage area of the mobile terminal device for accumulating the stress evaluation result. Also, by implementing the statistical processing on a device other than the mobile terminal, the load on the mobile terminal device can be reduced.

Sixth Embodiment

<Overview>

A program according to the embodiment of the disclosure is recorded and readable by a mobile terminal device, and the mobile terminal device executes the program to perform a function for computing a pupil change of a captured image in units of time by executing continuous still image capturing of the pupil change when light is irradiated. Further, the mobile terminal device records the program so that it can be read and executed. In addition, the configuration of this embodiment of the disclosure is further added with any one of the configurations of second to fifth embodiments.

Normally, the still images have higher resolution than the moving images. Therefore, by using continuous still images instead of moving images, the resolution increases and the recognition of the boundary portion of the pupil becomes accurate.

Hereinafter, functions and hardware contents of the mobile terminal device of this embodiment, and a processing flow will be described in detail.

<Functional Configuration>

Figure 16:
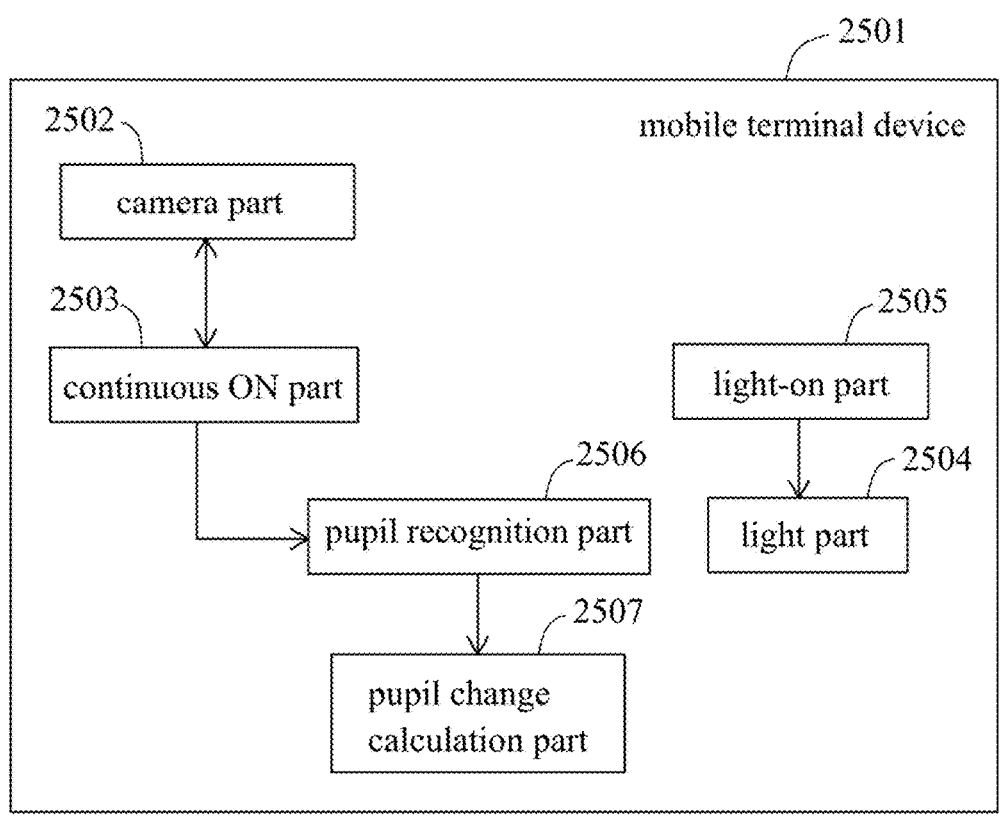
FIG. 16 is a is a functional block diagram of a mobile terminal device according to a sixth embodiment.

FIG. 16 is an example of functional blocks of the mobile terminal device of this embodiment. As shown in the figure, the mobile terminal device (2501) of this embodiment includes a camera part (2502), a continuous ON part (2503), a light part (2504), a light-on part (2505), a pupil recognition part (2506), and a pupil change calculation part (2507). The characteristic function of the present embodiment lies in the continuous ON part. Therefore, in the present embodiment, the function of the continuous ON part will be mainly described.

The "continuous ON part" functions to turn on the continuous still image capturing function of the mobile terminal. Even in this case, in order to investigate the pupil response to light, it is necessary to fill the pupil with the light even when the continuous still image is not being captured, so the "light-on part" is the same as in the previous embodiment, and the "light part" is continuously turned on.

"Capturing" in this continuous ON part includes a case of saving a captured still image at the same time, but the saving step is not indispensable. For example, in the continuous ON part, only continuous still images are taken, and a mode in which the continuous still images being captured are calculated in real time by the "pupil recognition part" and the "pupil change calculation part".

It is premised that pupils are included in the continuous still image being captured here, but it is preferable that not only the pupil but also the body part around the pupil other than the pupil is included. In the human eyeball, the health condition of the person appears in various forms. For example, in allergic conjunctivitis, infectious conjunctivitis, uveitis or dry eye, eye irritation is caused. Therefore, there is an effect that it is possible to know the above-mentioned symptoms due to the fact of eye congestion occurring in the conjunctiva.

For the capturing interval of the continuous still images, it is desirable to have short intervals. If the interval is short, it is possible to obtain information close to the moving image, and it is possible to obtain the accurate time required for the pupil to become the minimum, the pupil constriction rate, the pupil constriction speed and the pupil constriction acceleration. The short interval means that, for example, one still image is captured in 2 seconds, and one still image is taken in one second.

Furthermore, since this imaging interval affects the calculation in the pupil change calculation part, it is desirable that it exists as information associated with the pupil change information. For example, if one still image is captured per second, the pupil change per second is revealed by the still image.

<Hardware Configuration>

Figure 17:
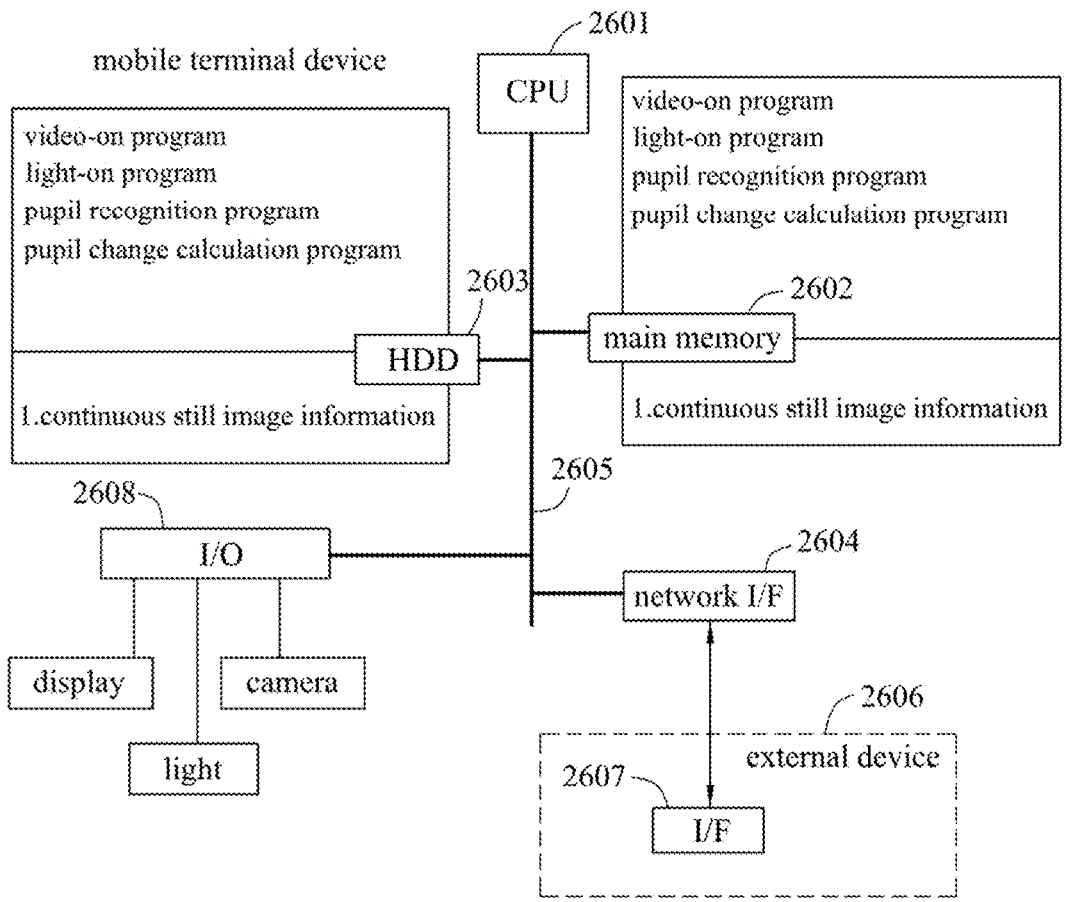
FIG. 17 is a schematic diagram showing the hardware structure of the mobile terminal device according to the sixth embodiment.

FIG. 17 is a diagram showing an example of the configuration of the mobile terminal device when the above functional components are implemented by hardware. The operation of each hardware component in each process in the present device will be described with reference to this figure.

As shown in the figure, the mobile terminal device of this embodiment is provided with a "CPU" (2601) for performing various arithmetic processing and a "main memory" (2602). In addition, the mobile terminal device further includes an "HDD" (2603), a "network I/F" (2604) for transmitting/receiving information to/from the "I/F" (2607) of the external device (2606), or an "I/O" (2608) for transmitting and receiving information between a camera, a light or a display. Then, they are mutually connected by a data communication route such as a "system bus" (2605) for transmitting/receiving or processing the information.

The stored program of the present embodiment includes a continuous ON program for turning on the moving image capturing function of the mobile terminal, a light-on program for turning on the light disposed at the image capturing side of the mobile terminal, a pupil recognition program for recognizing the pupil of the eye of an animal including a person from an image that is being captured, and a pupil change calculation program for calculating the pupil change which is a change in a dilation level of the recognized pupil over time. The characteristic program in this embodiment is a continuous ON program. The other programs are the same as described above.

The pupil image of the user acquired by the continuous ON program of the mobile terminal device is stored in the addresses of the "main memory" and "HDD". Then, in the "CPU" of the mobile terminal device, the pupil change over time recognized by the logical operation processing is calculated using the continuous still image information stored in the "main memory". When consecutively captured still images are stored, the continuous still image information is stored in the "HDD" as described above. On the other hand, in the case of recognizing and computing pupils in real time on a captured continuous still image, the continuous still image information is not stored in the "HDD".

<Processing Flow>

Figure 18:
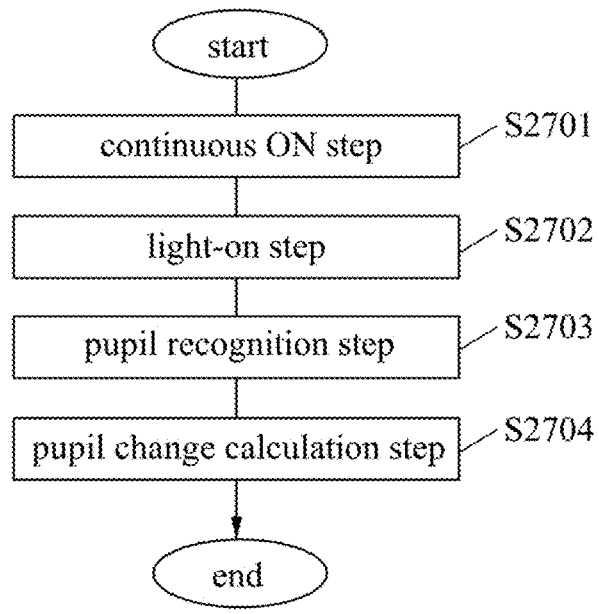
FIG. 18 is a flow chart showing a processing procedure according to the sixth embodiment.

FIG. 18 is a flow chart showing an example of the processing flow of the mobile terminal device of this embodiment. In addition, the following steps may be processing steps of a program recorded on a medium for controlling a computer (mobile terminal).

As shown in this figure, first, the continuous still image capturing function of the mobile terminal is turned on (S2701). Next, the light provided on the image capturing side of the mobile terminal is turned on (S2702). Then, a pupil of an eye of an animal including a person is recognized from the image being captured (S2703). Finally, a pupil change which is a change in a dilation level of the recognized pupil over time is calculated (S2704).

The order of the continuous ON step (S2701) for turning on the continuous still image capturing function of the mobile terminal and the light-on step (S2702) for turning on the light disposed at the image capturing side of the mobile terminal can be reversed. That is, first, the light disposed at the image capturing side of the mobile terminal is turned on. Next, the continuous still image capturing function of the mobile terminal is turned on. Then, the pupil of the eye of an animal including a person is recognized from the image being captured. Finally, a pupil change which is a change in a dilation level of the recognized pupil over time is calculated.

With the above steps, it is possible to measure the state of stress by objective symptoms having a correlation with stress by using the mobile terminal device.

Seventh Embodiment

<Overview>

In this embodiment, as a more preferable embodiment, a statistical processing device connected to a mobile terminal device having the configuration of the fourth or sixth embodiment, which includes the pupil change transmission part, is provided. As a general outline of the configuration of the statistical processing device, it receives the pupil change information from the mobile terminal device, accumulates the pupil change information, and performs the statistical processing.

By performing such statistical processing, for example, from the user, there are merits in that appropriate diagnosis can be obtained and appropriate future prediction can be made. In addition, from the provider, it is also possible to use medicine to provide goods or services such as supplements, medicines and healing music, to provide a fee-based information providing service, acquiring a huge amount of user information to improve diagnosis accuracy, or having the merit of making it useful for research. This is not limited to the present embodiment, and the statistical processing in other embodiments is also valid.

Hereinafter, the function of the device, the contents of the hardware in this embodiment, and the processing flow will be described in detail.

<Functional Configuration>

Figure 19:
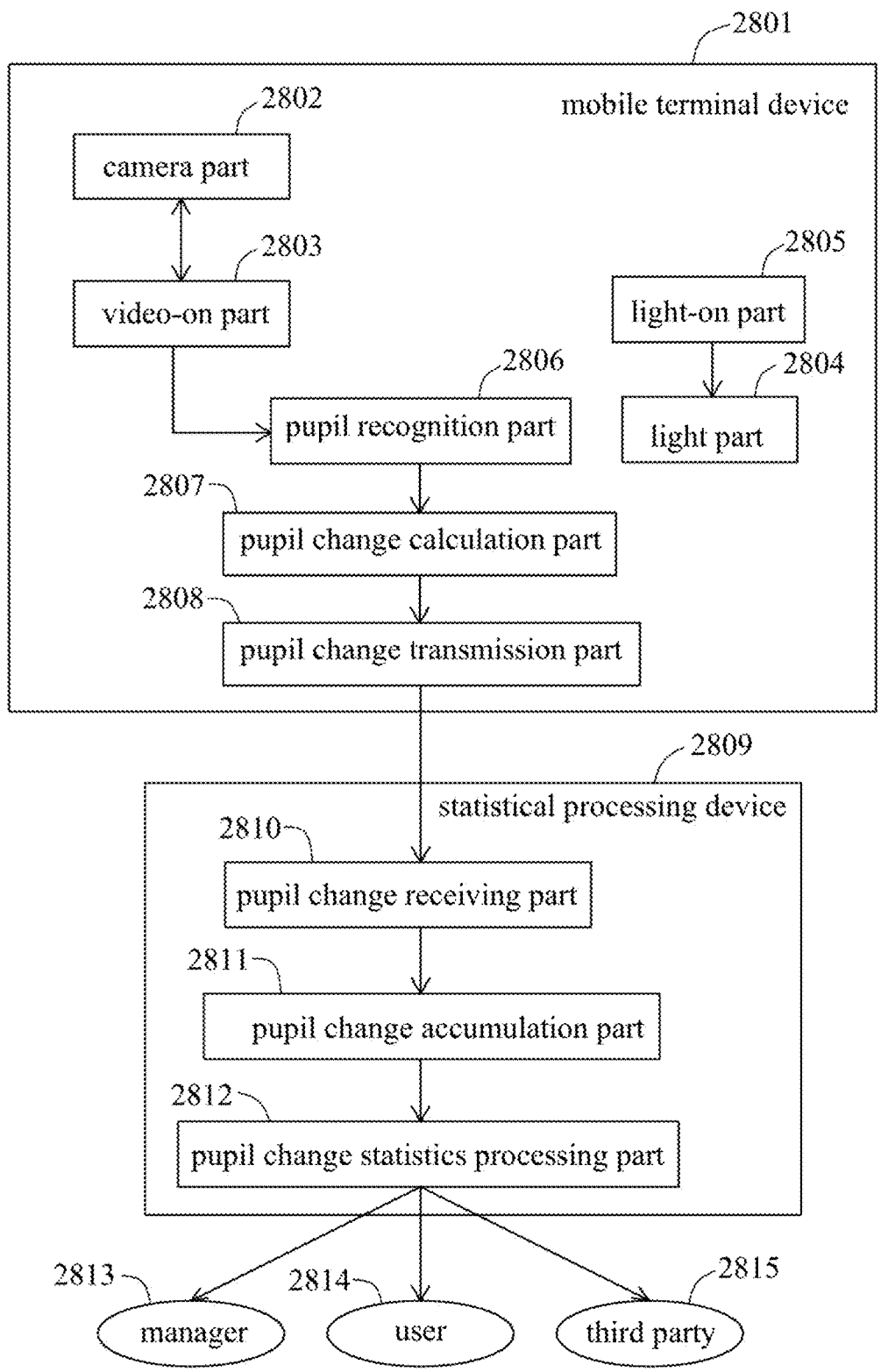
FIG. 19 is a is a functional block diagram of a mobile terminal device according to a seventh embodiment.

FIG. 19 is a diagram showing an example of functional blocks of the mobile terminal device and the statistical processing device of this embodiment. As shown in the figure, the mobile terminal device (2801) of the present embodiment includes a camera part (2801), a video-on part (2803), a light part (2804), a light-on part (2805), a pupil recognition part (2806), a pupil change calculation part (2807), and a pupil change transmission part (2808). The statistical processing apparatus (2809) of the present embodiment includes a pupil change receiving part (2810), a pupil change accumulation part (2811), and a pupil change statistics processing part (2812). The pupil change statistical processing part is connected to a user (2813), a manager (2814), or a third party (2815) such as a medical institution. The user (2813) includes the mobile terminal device for transmitting the pupil change from the pupil change transmission part to the statistical processing device. The feature of this embodiment lies in the contents of each part of the statistical processing device. Therefore, the functional configuration of each part of the statistical processing device will be mainly described. Since the other functions are the same as those described above, the description thereof will be omitted.

The "pupil change receiving part" functions to receive the pupil change transmitted from the mobile terminal device. Therefore, for example, in addition to the diameter value and the area value, the statistical processing device receives information such as the time required until the pupil becomes minimum, the pupil constriction rate, the pupil constriction speed and the pupil constriction acceleration. Also, in accordance with this, the additional information such as the name, sex, date of birth, hometown, measurement time, measurement place (for example, a residence, a university, a workplace, a pub, a train, a park, etc.), a case before and after meals, presence or absence and intensity of work on the occupation, measurement day, biological data such as body temperature, heart rate, blood pressure, skin electrical resistance, body movement, respiration and its variation, body composition data and treatment history. As shown in the figure, it is preferable that this additional information is held in association with pupil change information so that it can be easily used for later statistical processing.

The "pupil change accumulation part" functions to accumulate the received pupil change. Regarding the mode of accumulation, first, a mode of accumulating for each user can be considered. Then, it is possible to monitor the change of the stress state of the user in the form of comparison of accumulated pupil change information. Next, there is a method of dividing by date instead of dividing by users. According to this method, it is possible to accumulate, for example, the effect of weather on stress.

The "pupil change statistical processing part" functions to statistically process the accumulated pupil changes. As statistical processing, as described above, there are conceivable methods such as statistical processing for each user, statistical processing for each date, statistical processing for each additional information, and the likes.

As described above, from the user, the merit of performing the statistical processing is that the user can obtain an appropriate diagnosis and make an appropriate future prediction, and from the provider, it is also possible to receive a huge user information to increase the accuracy of diagnosis, providing service with payable information, provide goods or services such as supplements, medicines and healing music, and having the merit of making it useful for research. Therefore, the statistical processing device may have a function for disclosing the results of the statistical processing to the user or the like. As a function for disclosing, for example, a statistical processing device has a statistical information transmission part for transmitting statistical information to a terminal of a user or the like, and in a terminal of a user or the like, it includes a statistical information receiving part for receiving the statistical information transmitted from the statistical processing device. In addition, if the user terminal or the like has a statistical information output part for outputting the statistical information, for example, the user can recognize the statistical information through the display of the mobile terminal device or the like.

Figure 41:
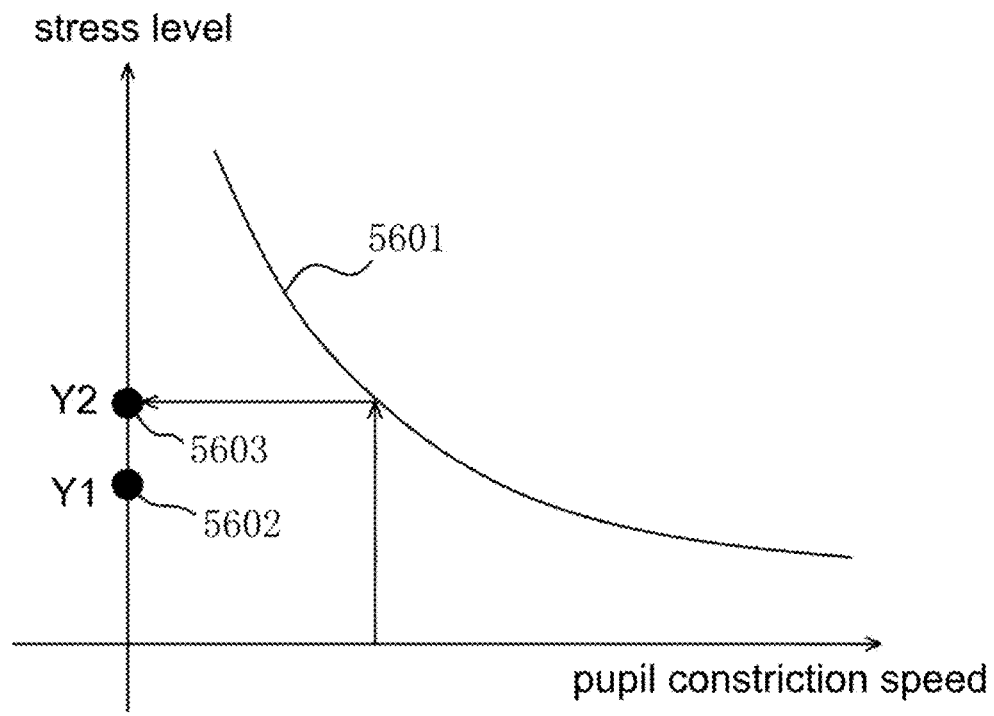
FIG. 41 is a schematic chart, wherein the horizontal axis indicates the pupil constriction speed, and the vertical axis indicates the stress level.

For example, it is conceivable to ask the user to input the stress level aware of the user, and compare the inputted stress level with the stress level induced by the pupil change. FIG. 41 is a view showing a case where the pupil constriction speed is plotted on the horizontal axis and the stress level is taken on the vertical axis. When the data of the statistical value are shown as the curve (5601), and the stress level as the subjective symptom of the user is $Y_1$ (5602), from the pupil constriction speed, if the part with the stress level is $Y_2$ (5603), it is diagnosed that it is the stress level corresponding to the part of $Y_2$ based on the statistical processing and the actual pupil constriction speed, and it is possible to output that effect. By doing this, the user can obtain an appropriate diagnosis.

Figure 42:
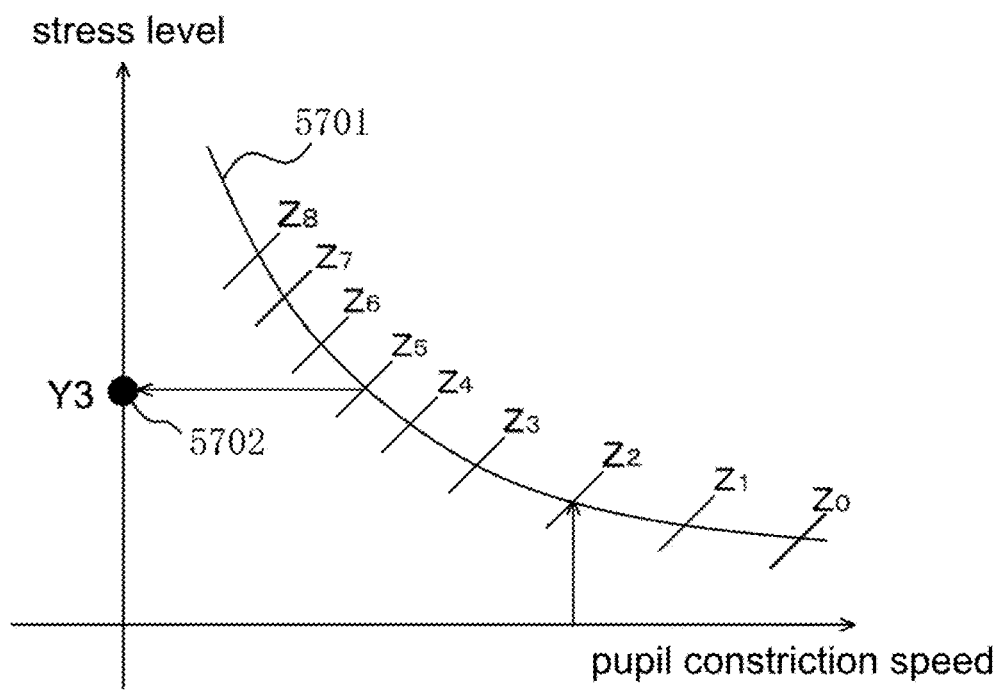
FIG. 42 is a schematic chart showing the stress change during a specific working period, wherein the horizontal axis indicates the pupil constriction speed, and the vertical axis indicates the stress level.

Next, FIG. 42 is a view showing a stress change for each time during a specific operation when the pupil constriction speed is plotted in the horizontal axis and the stress level is taken in the vertical axis. The curve (5701) derived as a result of the statistical processing expresses a stress change at each time, for example, in the portion of $Z_1$ after one hour from the portion of $Z_0$, in the portion of $Z_2$ after one hour later. In this figure, for example, if the stress state at the present time of the specific work is the part of $Z_2$, the part corresponding to $Z_3$ after that is the part of $Z_5$, it can be predicted that the stress intensity is $Y_3$ (5702). In this way, by appropriately statistically processing the stress change per hour, appropriate future prediction can be made.

These statistical processes can be statistically processed for each weather, meal, work environment, hobby, etc., as well as changes over time as long as additional information as described above is received at the same time. Then, by comprehensively combining these, stress diagnosis with high accuracy can be performed, and information for specifying stress causes can be obtained. In addition, the cause of the stress may be a cause of stress for each individual, or it may be considered to be a reasonable stress generally in the case of matters common to all users. In the case of stress reasons generally accepted in this way, the value of information that tells the fact is for high society, which leads to providing information with a fee. Furthermore, in addition to identifying the cause of stress, if it is possible to find an element that reduces stress, it may have a function of presenting the element or suggesting a solution to resolve the cause of stress. The meaning and use of these statistical processes is not limited to this example but is appropriate for the overall statistical process in the present disclosure.

<Hardware Configuration>

Figure 20:
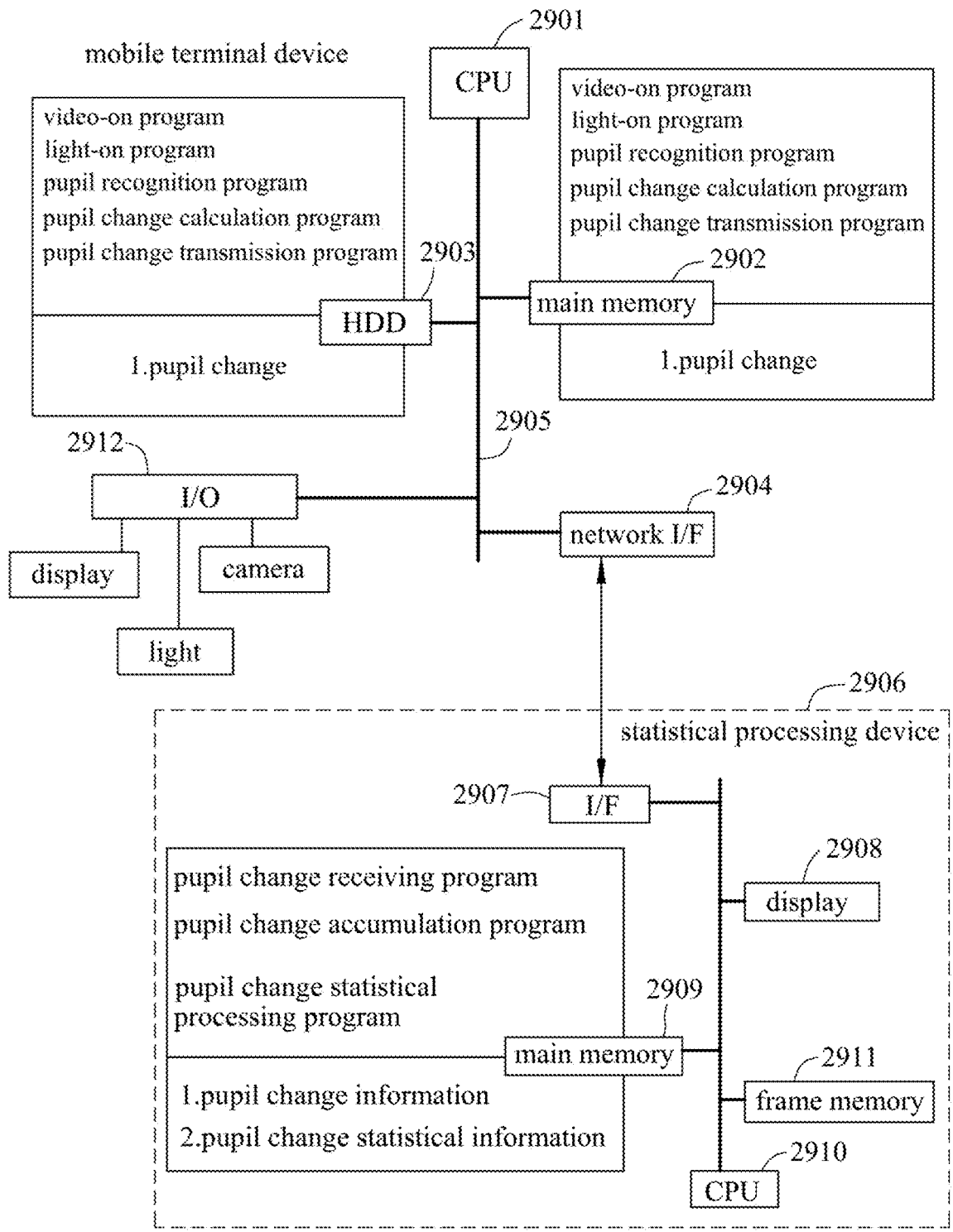
FIG. 20 is a schematic diagram showing the hardware structure of the mobile terminal device according to the seventh embodiment.

FIG. 20 is a diagram showing an example of a configuration of the mobile terminal device and the statistical processing device when the above functional components are implemented as hardware. The mobile terminal device includes a CPU (central processing unit) 2901, a main memory 2902, an HDD 2903, a network I/F 2904, an I/O 2912, and a "system bus" (2905), and the statistical processing device (2906) includes an "I/F" (2907), a "display" (2908), a "main memory" (2909), a "CPU" (2910), and a "frame memory" (2911).

Using these figures, the characteristic parts of this embodiment among the respective hardware components of each processing in the present device will be described, and the other parts are similar to the description of the above-mentioned embodiments.

The feature in this embodiment lies in the statistical processing device. In the mobile terminal device, the moving image information and the pupil change information stored in the "main memory" of the mobile terminal device are transmitted to the statistical processing device through the "network I/F" and the "pupil change transmission program". In the statistical processing device, these information are received via the "I/F" and the "pupil change receiving program", which is stored in "main memory" or "HDD" (not shown) of the statistical processing device, and the "pupil change accumulation program" can accumulate the pupil change information stored in the "main memory" or "HDD" (not shown). And the accumulated pupil change information is subjected to statistical processing using the "pupil change statistical processing program" by the operation of the "CPU" of the statistical processing device.

Furthermore, as described in the functional configuration, the statistical information transmission program for transmitting the statistical processing result to the mobile terminal may be stored in the "main memory" of the statistical processing device. The "main memory" may store a statistical information receiving program for receiving the transmitted statistical processing result from the statistical processing device and a statistical information output program for outputting the statistical information.

<Processing Flow>

Figure 21:
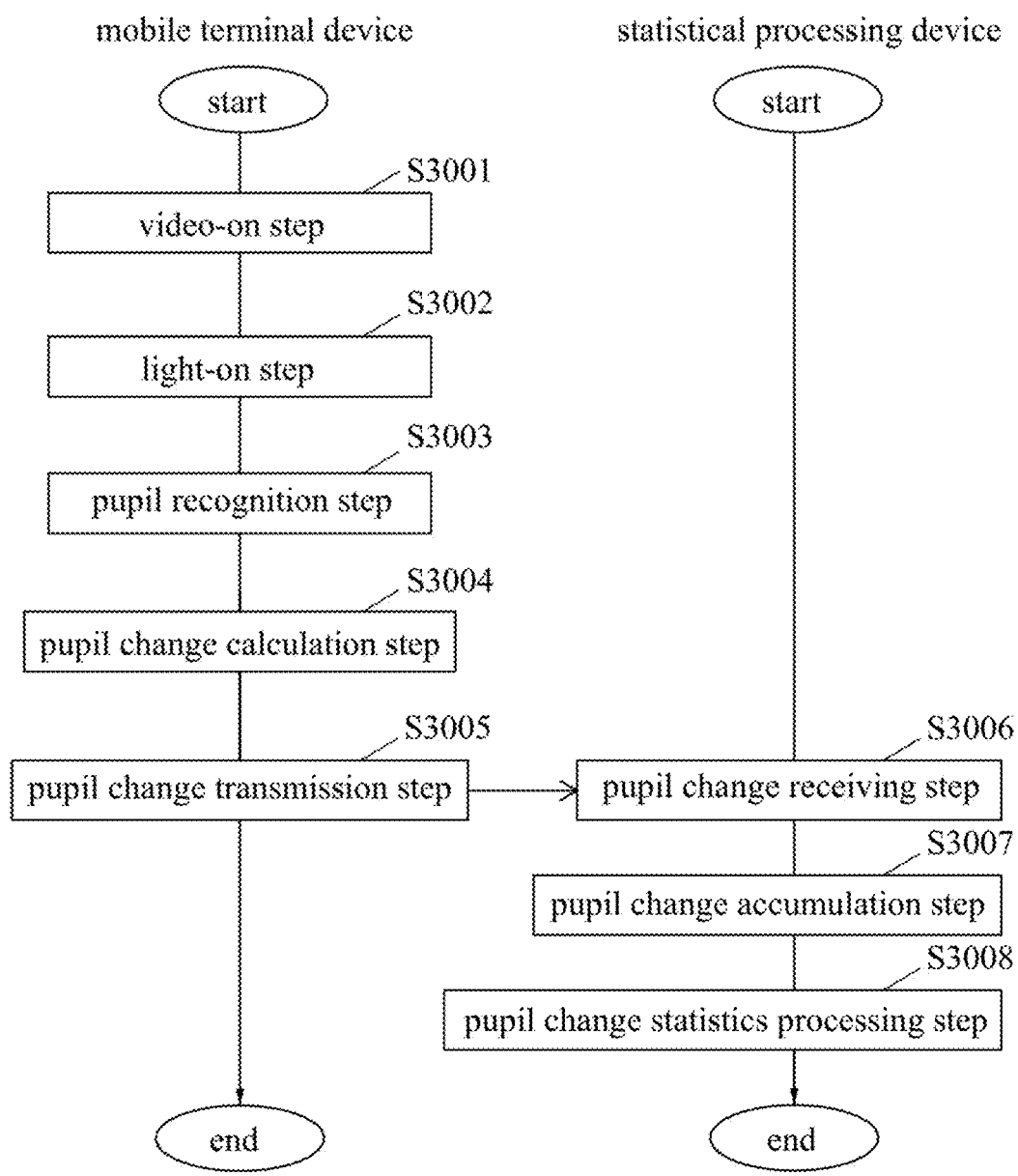
FIG. 21 is a flow chart showing a processing procedure according to the seventh embodiment.

FIG. 21 is a flow chart showing an example of the processing flow in the mobile terminal device and the statistical processing device of this embodiment. The following steps may be processing steps of a program recorded on a medium for controlling a computer (mobile terminal or statistical processing terminal).

The mobile terminal device includes a video-on step (S3001), a light-on step (S3002), a pupil recognition step (S3003), a pupil change calculation step (S3004), and a pupil change transmission step (S3005). The statistical processing device includes a pupil change receiving step (S3006), a pupil change accumulation step (S3007), and a pupil change statistical processing step (S3008). Using the figure, the characteristic parts of this embodiment among the flow of each processing in the present device will be described, and the other parts are the same as the description of the above-mentioned embodiments.

In the processing of this embodiment, a processing step in the statistical processing device is added. The "pupil change receiving step" in the statistical processing device is the step of receiving the pupil change transmitted as a result of executing the pupil change transmission step in the mobile terminal device. Further, the "pupil change accumulation step" in the statistical processing device is a step of accumulating the received pupil change. The "pupil change statistical processing step" in the statistical processing device is a step of statistically processing the stored pupil changes.

As described in the functional configuration, the mode of statistical processing is not limited to each user. Also, for example, by associating with the information such as the brightness of the measured place, the measurement time, before and after meals, sleeping time of the previous day, presence or absence and intensity of work at the measurement date, when disclosed to the user, it contributes to analysis of the user's stress cause.

As a device for disclosing statistical information to a user, the statistical processing device further includes a statistical information transmission step for transmitting the statistical information to the mobile terminal. In the mobile terminal device, it is considered to provide the processing flow including a statistical information receiving step for receiving the transmitted statistical information from the statistical processing device, and a statistical information output step for outputting the received statistical information.

With such a processing flow, it is possible to perform statistical processing of the pupil response to light, thereby making it possible for the user to generate information for realizing the characteristics and the like of the stress caused by the user.

Eighth Embodiment

<Overview>

In this embodiment, as a more preferable embodiment, there is provided a statistical processing device connected to a mobile terminal device added with the configuration of the fifth embodiment in the fourth embodiment. As an outline of the configuration of the statistical processing device, it receives a stress evaluation result and a pupil change from the mobile terminal device, accumulates the received information, and performs statistical processing to the information.

Hereinafter, the function of the device, the contents of the hardware in this embodiment, and the processing flow will be described in detail.

<Functional Configuration>

Figure 22:
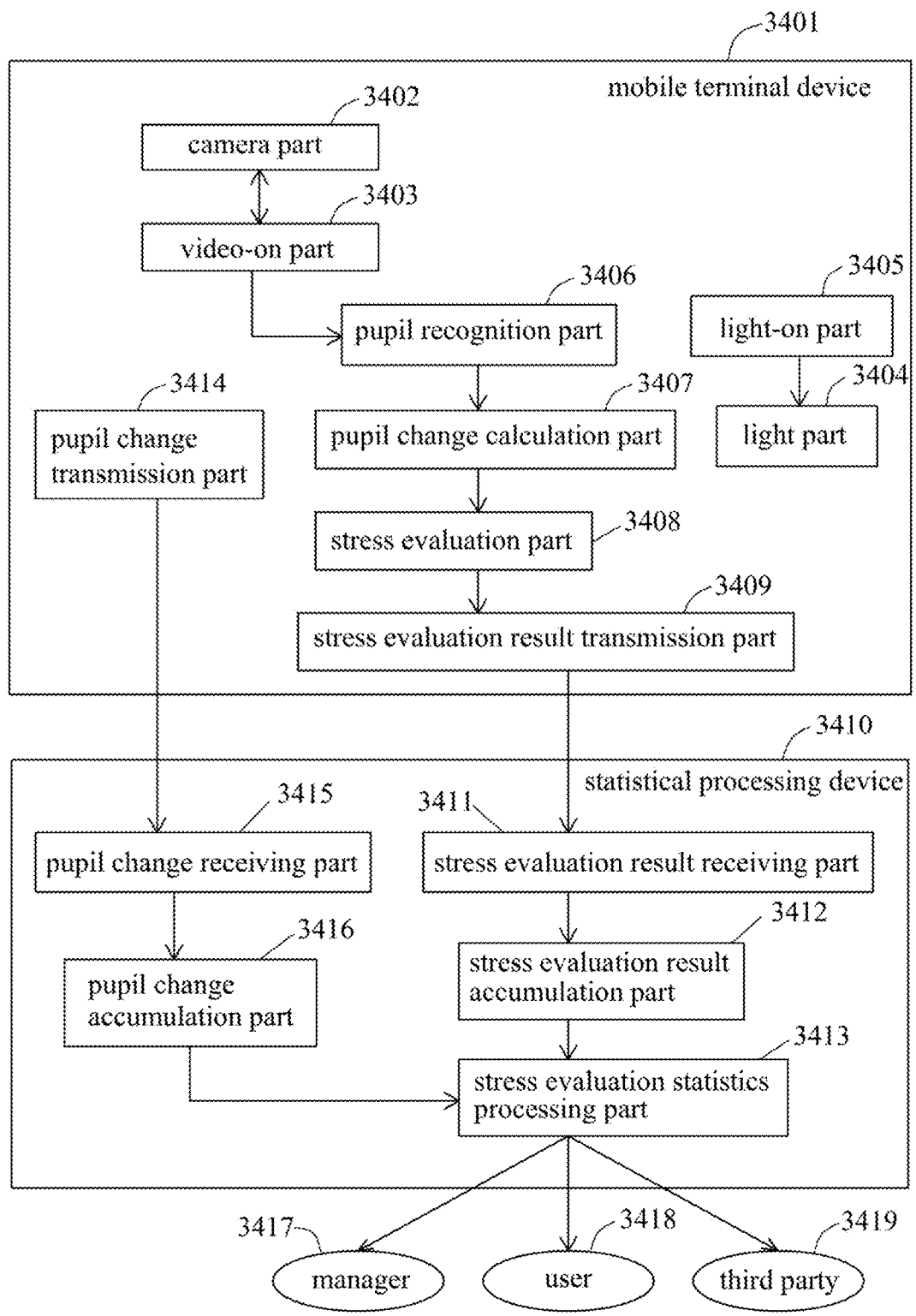
FIG. 22 is a is a functional block diagram of a mobile terminal device according to an eighth embodiment.

FIG. 22 is a diagram showing an example of functional blocks of the mobile terminal device and the statistical processing device of this embodiment. As shown in the figure, the mobile terminal device (3401) of this embodiment includes a camera part (3402), a video-on part (3403), a light part (3404), a light-on part (3405), a pupil recognition part (3406), a pupil change calculation part (3407), a stress evaluation part (3408), a stress evaluation result transmission part (3409), and a pupil change transmission part (3414). Then, the statistical processing device (3410) of this embodiment includes a stress evaluation result receiving part (3411), a stress evaluation result accumulation part (3412), a stress evaluation statistical processing part (3413), a pupil change receiving part (3415), and a pupil change accumulation part (3416). The stress evaluation statistical processing part is connected to a user (3417), a manager (3418), or a third party (3419) such as a medical institution. The feature of this embodiment lies in the contents of each part of the statistical processing device. Therefore, the functional configuration of each part of the statistical processing device will be mainly described. Since the other functions are the same as those described above, the description thereof will be omitted.

The "stress evaluation result receiving part" functions to receive the stress evaluation result transmitted from the mobile terminal device. Therefore, for example, the statistical processing device receives a stress evaluation indicated by a numerical value such as % of stress, a stepwise expression such as large, medium and small, a comparison value with the previous day and a maximum value/minimum value, and the likes.

The "stress evaluation result accumulation part" functions to accumulate the received stress evaluation result. Regarding the mode of accumulation, a mode of accumulating for each user is conceivable. Then, changes in stress evaluation results of the user can be grasped in the form of changes in accumulated stress evaluation results. Next, there is a method of dividing by date instead of dividing by users. According to this method, it is possible to accumulate, for example, the influence of weather on the stress evaluation result and the likes.

The "stress evaluation statistical processing part" functions to statistically process accumulated stress evaluation results and pupil changes. As the statistical processing, as described above, there are conceivable methods such as statistical processing for each user, statistical processing for each date, and the likes.

Furthermore, as described in the above embodiments, the statistical processing device may have a function for disclosing the result of the statistical processing to the user or the likes. As a function for disclosing, for example, the statistical processing device includes a statistical information transmission part for transmitting statistical information to a terminal of a user or the likes, and the terminal of a user or the likes includes a statistical information receiving part for receiving the statistical information transmitted from the statistical processing device.

Figure 47:
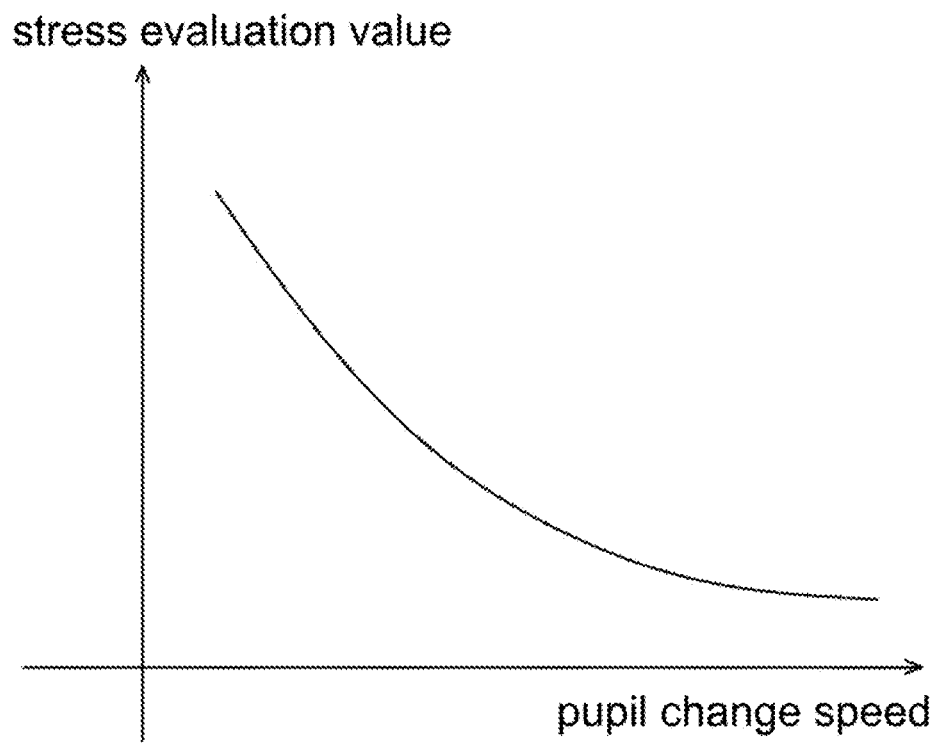
FIG. 47 is a schematic diagram showing curves, wherein the vertical axis indicates the stress evaluation value, and the horizontal axis indicates the pupil change speed.

FIG. 47 is a diagram showing an output form of the user side, wherein the vertical axis represents the stress evaluation value and the horizontal axis represents the pupil change speed. It can be seen that the stress evaluation value decreases as the pupil change speed increases.

Figure 48:
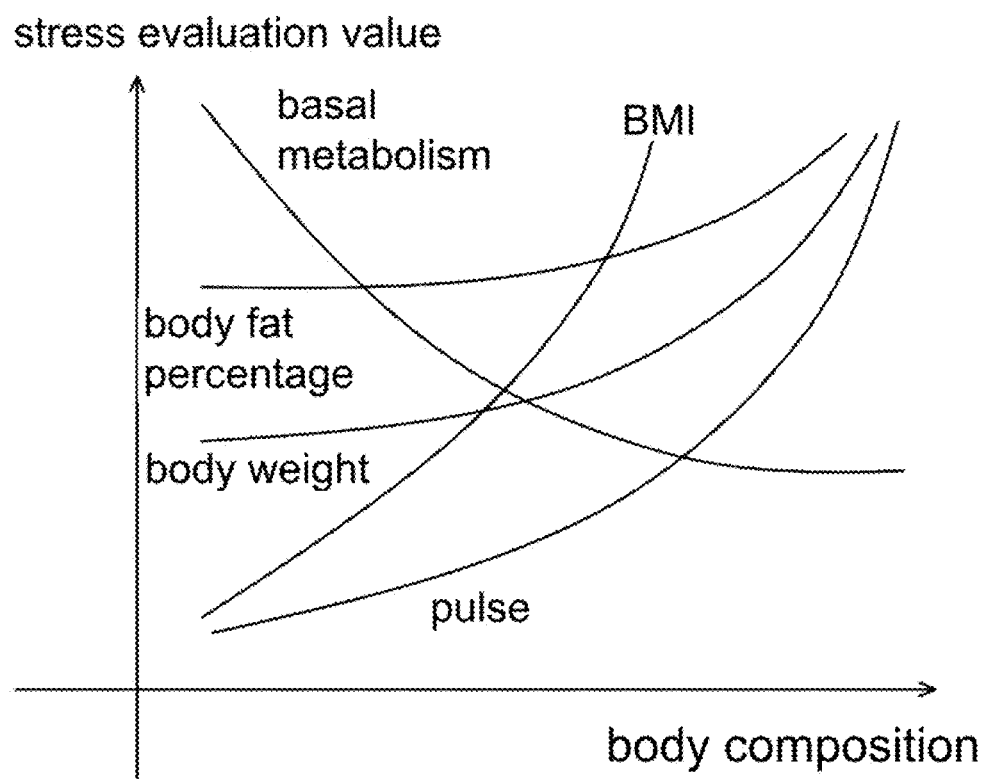
FIG. 48 is a schematic diagram showing curves, wherein the vertical axis indicates the stress evaluation value, and the horizontal axis indicates the body composition.

Further, FIG. 48 is a diagram showing an output form of the user side, wherein the vertical axis represents the stress evaluation value and the horizontal axis represents the body composition amount. As shown in the curve of the figure, for body fat percentage, body weight, BMI and pulse, the higher the body composition amount, the higher the stress evaluation value is. On the other hand, as for the basal metabolism, it is understood that the higher the body composition amount, the lower the stress evaluation value is. If such statistical information is obtained, the user or the likes can objectively analyze the cause of the stress. In addition, as compared with the pupil change, since the stress evaluation value clearly correlates with the stress, it is easy to understand at first glance.

As described above, it is possible to receive the data after performing the stress evaluation process on the mobile terminal device of the user who is not required to perform the stress evaluation process, thereby reducing the loading of the server.

<Hardware Configuration>

Figure 23:
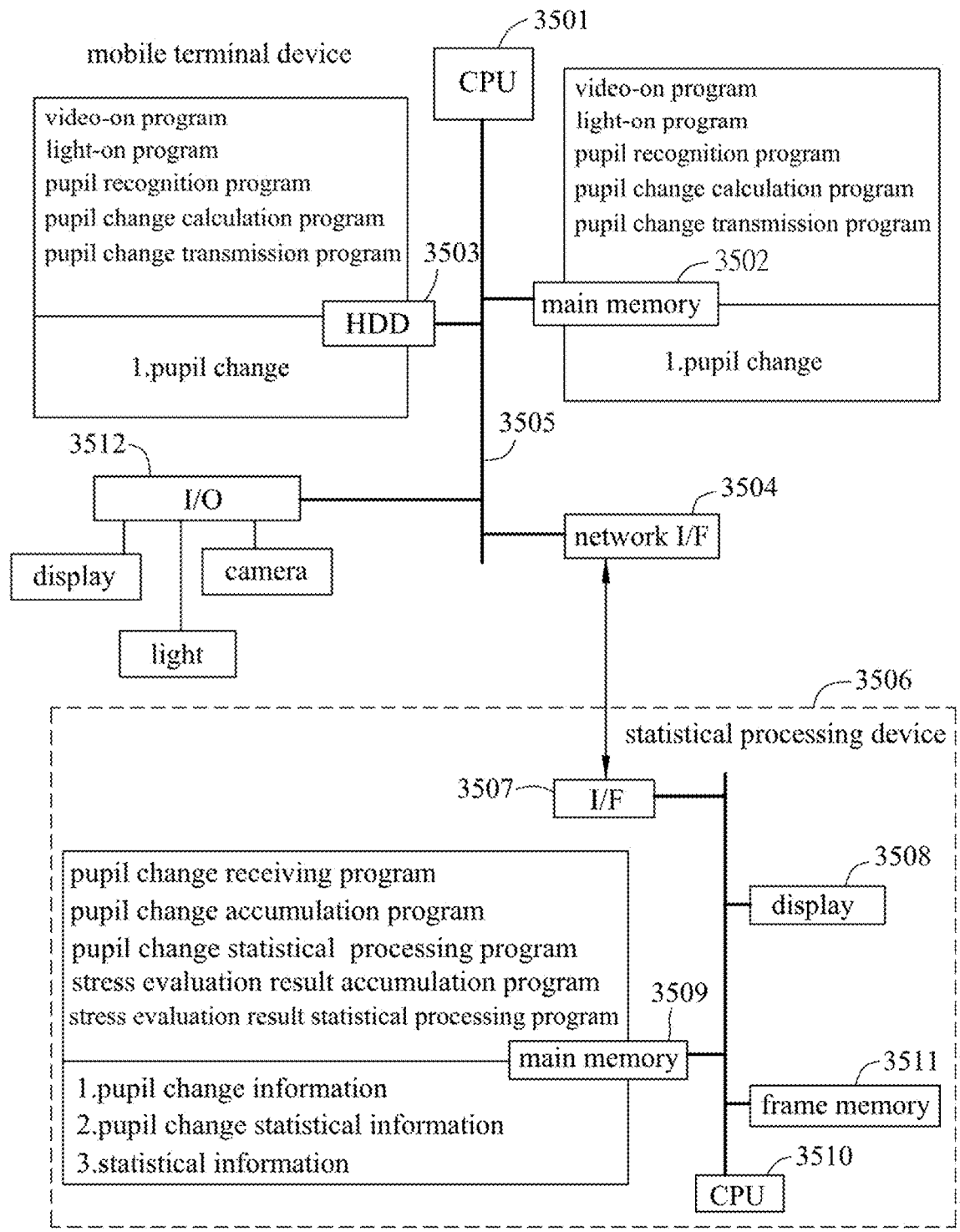
FIG. 23 is a schematic diagram showing the hardware structure of the mobile terminal device according to the eighth embodiment.

FIG. 23 is a diagram showing an example of the configuration of the mobile terminal device and the statistical processing device when the above functional components are implemented as hardware. The mobile terminal device includes a CPU (central processing unit) (3501), a main memory (3502), an HDD (3503), a network I/F (3504), an I/O (3512), and a "system bus" (3505), and the statistical processing device (3506) includes an "I/F" (3507), a "display" (3508), a "main memory" (3509), a "CPU" (3510), and a "frame memory" (3511).

Using these figures, the characteristic parts of this embodiment among the respective hardware components of each processing in the present device will be described, and the other parts are similar to the description of the above-mentioned embodiments.

The feature in this embodiment lies in the statistical processing device. In the mobile terminal device, the stress evaluation information stored in the "main memory" of the mobile terminal device is transmitted to the statistical processing device through the "network I/F" by the "stress evaluation result transmission program". In the statistical processing device, the transmitted information are received via the "I/F" by the "stress evaluation result receiving program" and stored in "main memory" or "HDD" (not shown) of the statistical processing device. Then, the "stress evaluation result accumulation program" accumulates the stress evaluation information in the "main memory" or "HDD" (not shown). And the stored stress evaluation information is subjected to statistical processing using the "stress evaluation statistical processing program" by the function of "CPU" of the statistical processing device.

Furthermore, a statistical information transmission program for transmitting the statistical processing result to the mobile terminal may be stored in the "main memory" of the statistical processing device. Or, the "main memory" of the mobile terminal device may store a statistical information receiving program for receiving the statistical processing result from the statistical processing device, and store a statistical information output program for outputting the statistical information.

<Processing Flow>

Figure 24:
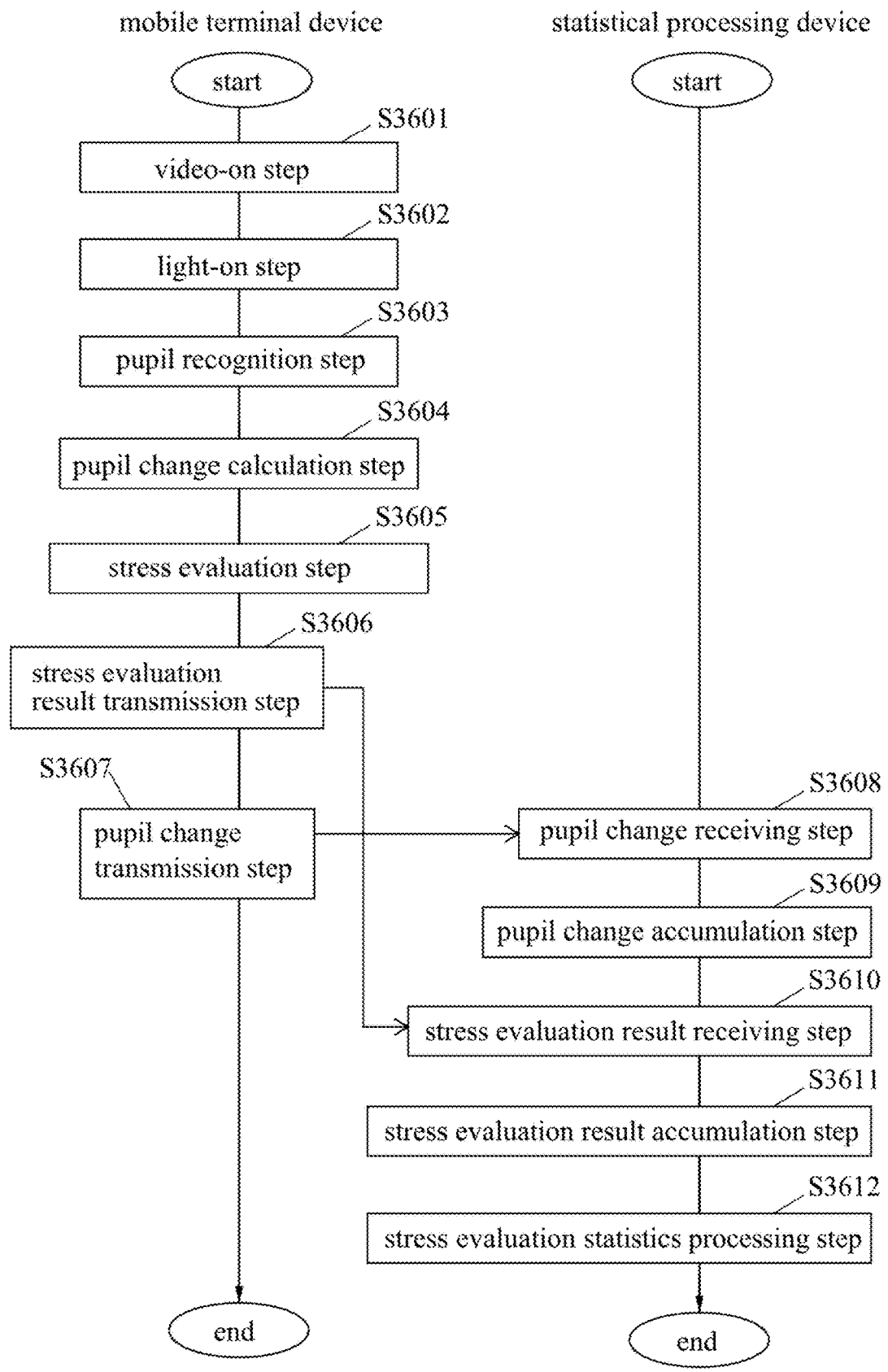
FIG. 24 is a flow chart showing a processing procedure according to the eighth embodiment.

FIG. 24 is a flow chart showing an example of a processing flow of the mobile terminal device and the statistical processing device of this embodiment. The following steps may be processing steps of a program recorded on a medium for controlling a computer (mobile terminal, statistical processing terminal).

The mobile terminal device includes a video-on step (S3601), a light-on step (S3602), a pupil recognition step (S3603), a pupil change calculation step (S3603), a stress evaluation step (S3604), a stress evaluation result transmission step (S3605), and a pupil change transmission step (S3606). Then, the statistical processing device performs a pupil change receiving step (S3607), a pupil change accumulation step (S3608), a stress evaluation result receiving step (S3609), a stress evaluation result accumulating step (S3610), and a stress evaluation statistical processing step (S3611). Using these figures, the characteristic parts of this embodiment among the flow of each processing in the present device will be described, and the other parts are the same as the description of the above-mentioned embodiments.

In the processing of this embodiment, a processing step in the statistical processing device is added. The "stress evaluation result receiving step" in the statistical processing device is the step of receiving the stress evaluation result transmitted as a result of executing the stress evaluation result transmission step by the mobile terminal device. This stress evaluation result is sent in association with pupil change. Thereby, the loading of stress evaluation within the statistical processing device can be reduced. The "stress evaluation result accumulation step" in the statistical processing device is a step of accumulating the received stress evaluation result. The "stress evaluation statistical processing step" in the statistical processing device is a step of statistically processing the accumulated stress evaluation result.

The "stress evaluation result receiving step" is not limited to the relationship in the statistical processing device as long as it is after the stress evaluation result transmission step in the mobile terminal device. For example, it may be prior to the pupil change receiving step. Next, the "stress evaluation result accumulation part" is not limited as long as it is after the body composition data receiving step in the statistical processing device. Similarly, regarding the "pupil change receiving step" and the "pupil change accumulation step", the relationship between the stress evaluation result receiving step and the stress evaluation result accumulating step does not matter. However, the "stress evaluation statistical processing step" is based on the stored pupil changes and the stress evaluation results, so it is done after both the stress evaluation result accumulation step and the pupil change accumulation step are completed.

The mode of statistical processing is not limited to each user. Also, for example, by associating with the information such as the brightness of the measured place, the measurement time, before or after meals, sleeping time on the previous day, presence or absence and intensity of work at the measurement date, when disclosed to the user, it contributes to analysis of user's body composition data.

As a device for disclosing statistical information to a user, the statistical processing device further includes a statistical information transmission step for transmitting the statistical information to the mobile terminal. In the mobile terminal device, it is considered to provide the processing flow including a statistical information receiving step for receiving the transmitted statistical information from the statistical processing device, and a statistical information output step for outputting the received statistical information.

Ninth Embodiment

<Overview>

A program according to the embodiment of the disclosure is recorded and readable by a mobile terminal device, and the mobile terminal device executes the program to perform a function for computing a pupil change of a captured image in units of time by executing moving image capturing of the pupil change when light is irradiated, and transmitting it to the external device. Further, the mobile terminal device records the program so that it can be read and executed.

Hereinafter, functions and hardware contents of the mobile terminal device of this embodiment, and a processing flow will be described in detail.

<Functional Configuration>

Figure 25:
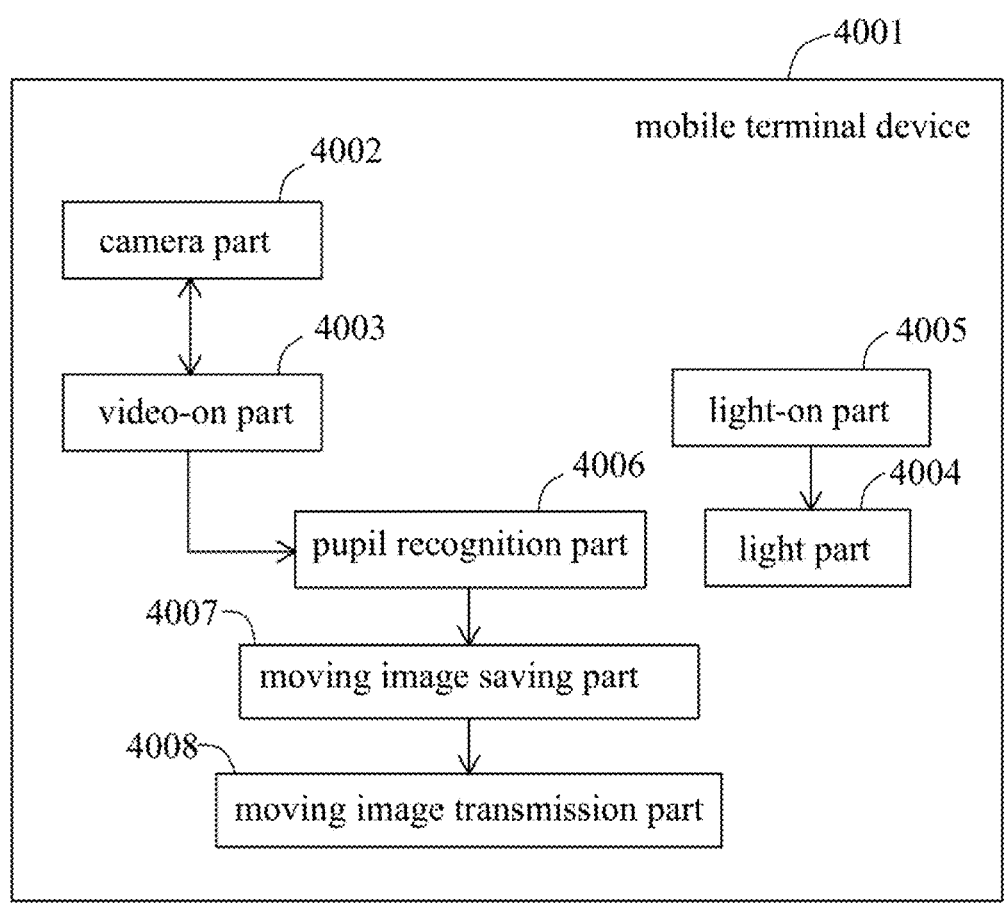
FIG. 25 is a is a functional block diagram of a mobile terminal device according to a ninth embodiment.

FIG. 25 is an example of functional blocks of the mobile terminal device of this embodiment. As shown in the figure, the mobile terminal device (4001) of this embodiment includes a camera part (4002), a video-on part (4003), a light part (4004), a light-on part (4005), a pupil recognition part (4006), a moving image saving part (4007), and a moving image transmission part (4008). The characteristic function of the present embodiment lies in the moving image saving part and the moving image transmission part. Therefore, in the present embodiment, the functions of the moving image saving part and the moving image transmission part will be mainly described.

In any of the above embodiments, the content of calculating the pupil change is executed by the mobile terminal device. Although this method can finish the calculation by the mobile terminal device, in order to achieve the subjective of this disclosure, it is unnecessary to finish the calculation of the pupil change by the mobile terminal device. In this embodiment, the pupil change calculation is performed by the external device, and the mobile terminal device transmits the moving image for recognizing the pupil change saved in the pupil recognition part to the external device, thereby achieving the subjective of this disclosure. In other words, the external device includes a function of the pupil change calculation part of the first embodiment, and preferably further includes a function of the stress evaluation part of the third embodiment.

The "moving image saving part" has a function for saving a moving image captured by the video-on part. The saved moving image may include the pupil part and the non-pupil part, which are separated.

The "moving image transmission part" includes a function for transmitting the saved moving image to a preset address. Accordingly, the moving image information of the captured pupil of the user can be transmitted to the external device.

According to this embodiment, the pupil change calculation is performed by the external device instead of the mobile terminal device for measuring the stress state according to the objective symptoms having a correlation with stress. In addition, the moving image information is accumulated in the frame memory of the external device, and each of the preset frames can be outputted by the display of the external device. Furthermore, the stress evaluation information and the likes, the same as other embodiments, are preferably listed by displaying on the user terminal including the mobile terminal device and the likes.

As described above, it is possible to reduce the processing of the mobile terminal device and reduce the loading of the mobile terminal device.

<Hardware Configuration>

Figure 26:
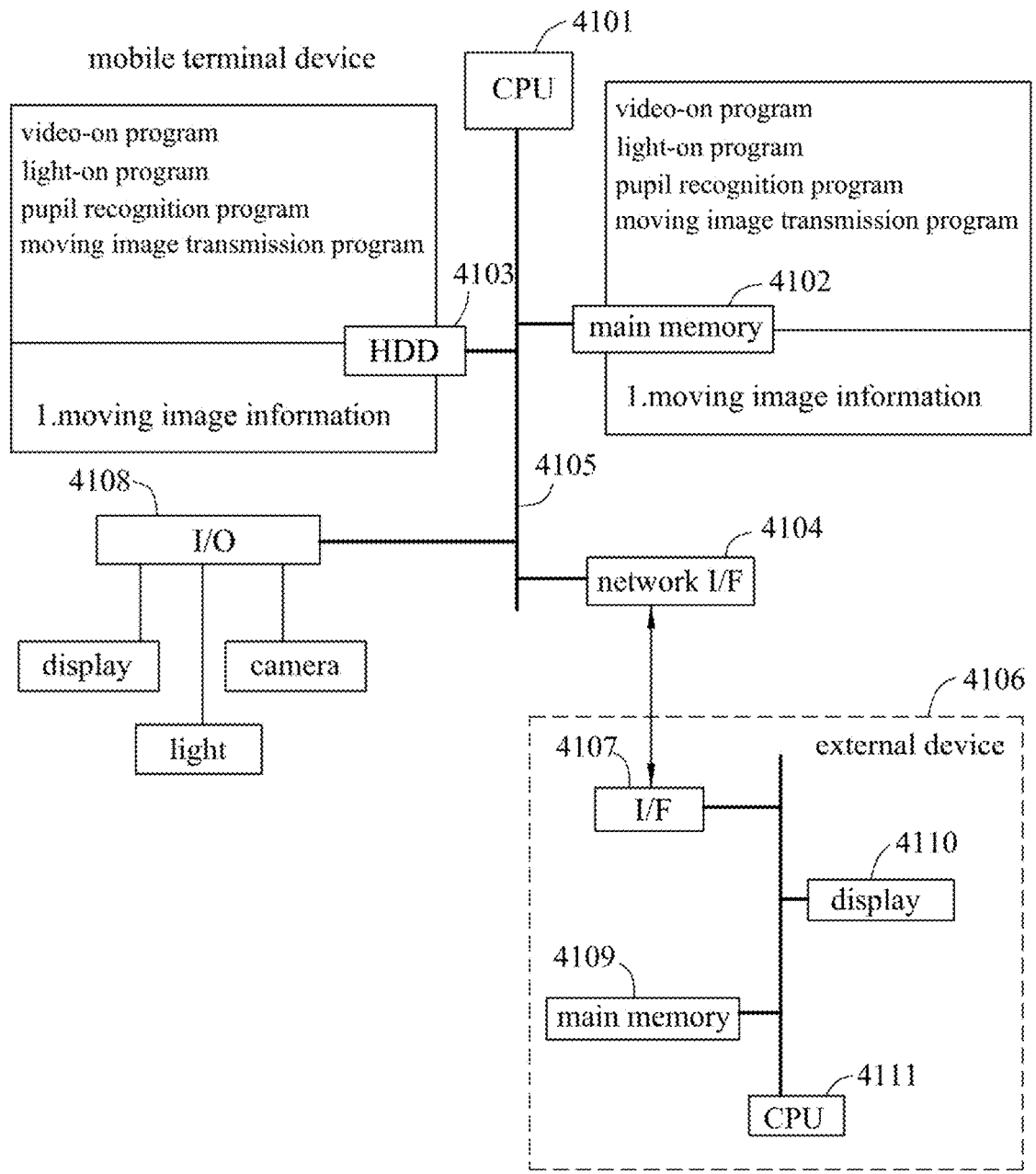
FIG. 26 is a schematic diagram showing the hardware structure of the mobile terminal device according to the ninth embodiment.

FIG. 26 is a diagram showing an example of the configuration of the mobile terminal device and the statistical processing device when the above functional components are implemented as hardware. Each of the hardware configuration parts for each processing of the device will be described with reference the figure.

As shown in the figure, the mobile terminal device of this embodiment is provided with a "CPU" (4101) for performing various arithmetic processing and a "main memory" (4102). In addition, the mobile terminal device further includes an "HDD" (4103), a "network I/F" (4104) for transmitting/receiving information to/from the "I/F" (4107) of the external device (4106), or an "I/O" (4108) for transmitting and receiving information between a camera, a light or a display. Then, they are mutually connected by a data communication route such as a "system bus" (4105) for transmitting/receiving or processing the information. The external device includes a "frame memory" (4109), a "display" (4110) and a "CPU" (4111).

In this embodiment, the program stored in the "main memory" includes a video-on program for enabling a moving image capturing function of the mobile terminal, a light-on program for enabling a light disposed at an image capturing side of the mobile terminal, a pupil recognition program for recognizing pupils of animal eyes including human eyes from an image that is being captured, and a moving image transmission program for transmitting the saved moving image to a preset address.

The pupil image of the user acquired by the video-on program of the mobile terminal device is stored in the addresses of the "main memory" and "HDD". Then, in the "CPU" of the mobile terminal device, the moving image information stored in the "main memory" is transmitted to the "I/F" of the external device via the "network I/F".

<Processing Flow>

Figure 27:
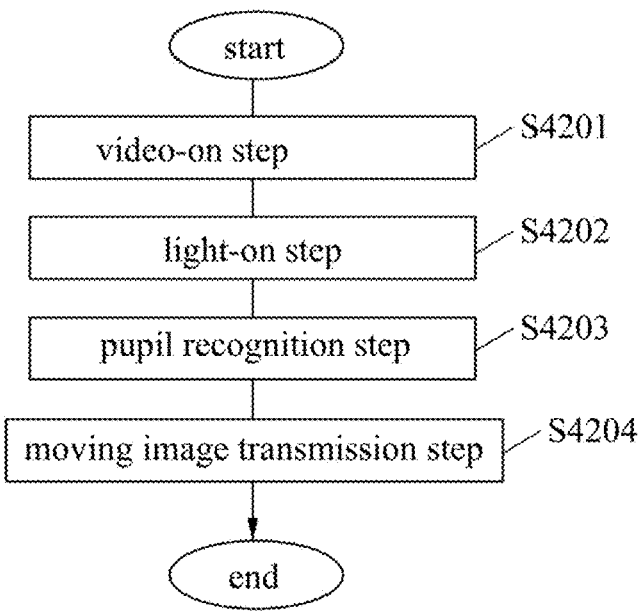
FIG. 27 is a flow chart showing a processing procedure according to the ninth embodiment.

FIG. 27 is a flow chart showing an example of the processing flow of the mobile terminal device of this embodiment. In addition, the following steps may be processing steps of a program recorded on a medium for controlling a computer (mobile terminal).

As shown in this figure, first, the moving image capturing function of the mobile terminal is turned on (S4201). Next, the light provided on the image capturing side of the mobile terminal is turned on (S4202). Then, a pupil of an eye of an animal including a person is recognized from the image being captured (S4203). Afterwards, a moving image captured by the video-on step is saved. Finally, the saved moving image is transmitted to a preset address. (S4204).

The order of the video-on step (S4201) for turning on the moving image capturing function of the mobile terminal and the light-on step (S4202) for turning on the light disposed at the image capturing side of the mobile terminal can be reversed. That is, first, the light disposed at the image capturing side of the mobile terminal is turned on. Next, the moving image capturing function of the mobile terminal is turned on. Then, a pupil of an eye of an animal including a person is recognized from the image being captured, and a moving image captured by the video-on step is saved. Finally, the saved moving image is transmitted to a preset address.

According to the above steps, it is unnecessary to perform the pupil change calculation by the mobile terminal device, and the stress state can be measured according to the objective symptoms having a correlation with stress.

Tenth Embodiment

<Overview>

A program according to the embodiment of the disclosure is recorded and readable by a mobile terminal device, and the mobile terminal device executes the program to perform a function for computing a pupil change of a captured image in units of time by executing continuous still image capturing of the pupil change when light is irradiated, and transmitting it to the external device. Further, the mobile terminal device records the program so that it can be read and executed.

Hereinafter, functions and hardware contents of the mobile terminal device of this embodiment, and a processing flow will be described in detail.

<Functional Configuration>

Figure 28:
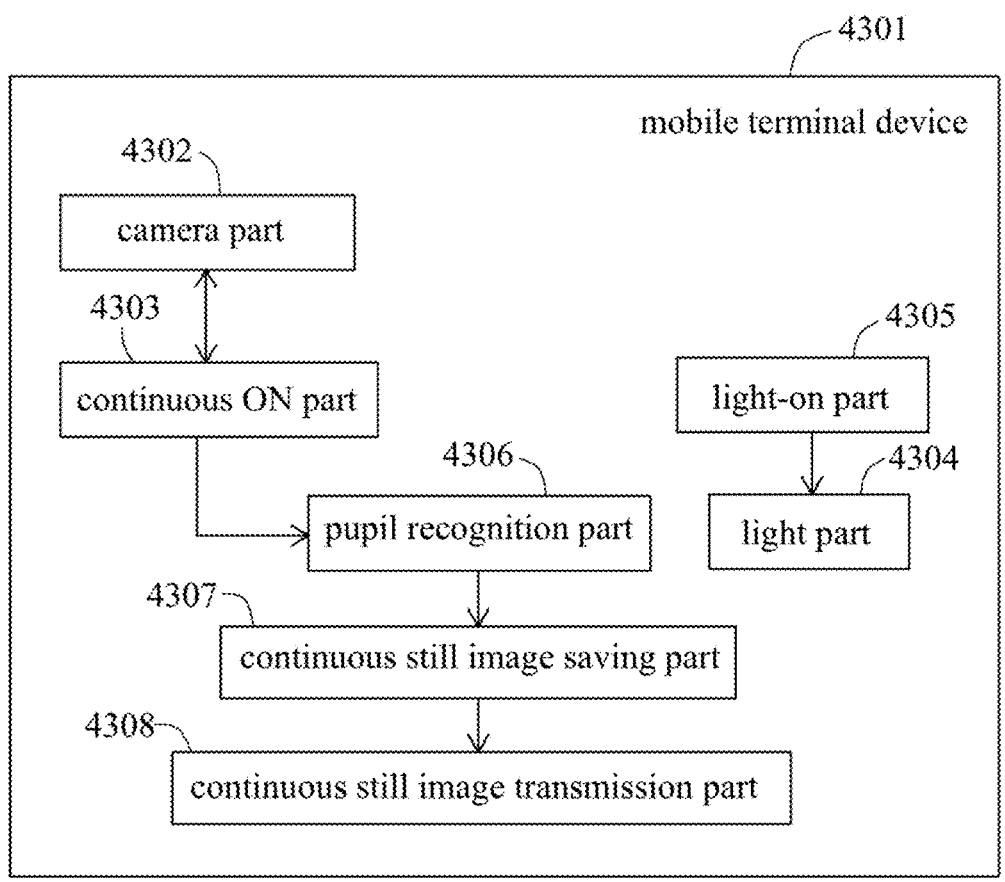
FIG. 28 is a is a functional block diagram of a mobile terminal device according to a tenth embodiment.

FIG. 28 is an example of functional blocks of the mobile terminal device of this embodiment. As shown in the figure, the mobile terminal device (4301) of this embodiment includes a camera part (4302), a continuous ON part (4303), a light part (4304), a light-on part (4305), a pupil recognition part (4306), a continuous still image saving part (4307), and a continuous still image transmission part (4308). The characteristic function of the present embodiment lies in the continuous still image saving part and the continuous still image transmission part. Therefore, in the present embodiment, the function of the moving image saving part and the moving image transmission part will be mainly described.

In this embodiment, similar to the ninth embodiment, the external device executes the pupil change calculation, and the mobile terminal device transmits the continuous still image for recognizing the pupil change saved in the pupil recognition part to the external device, thereby achieving the subjective of this disclosure. Different from the ninth embodiment, this embodiment captures the continuous still image, so the continuous still image is saved and transmitted. The above embodiment has described the details of capturing the continuous still image, and the continuous still image saving part and the continuous still image transmission part will be described hereinafter.

The "continuous still image saving part" has a function for saving a continuous still image captured by the mobile terminal. The saved moving image may include the pupil part and the non-pupil part, which are separated.

The "continuous still image transmission part" has a function for transmitting the saved continuous still image to a preset address. Accordingly, the continuous still image information of the captured pupil of the user can be transmitted to the external device.

According to this embodiment, the mobile terminal device does not need to perform the pupil change calculation and measure the stress state according to the objective symptoms having a correlation with stress.

<Hardware Configuration>

Figure 29:
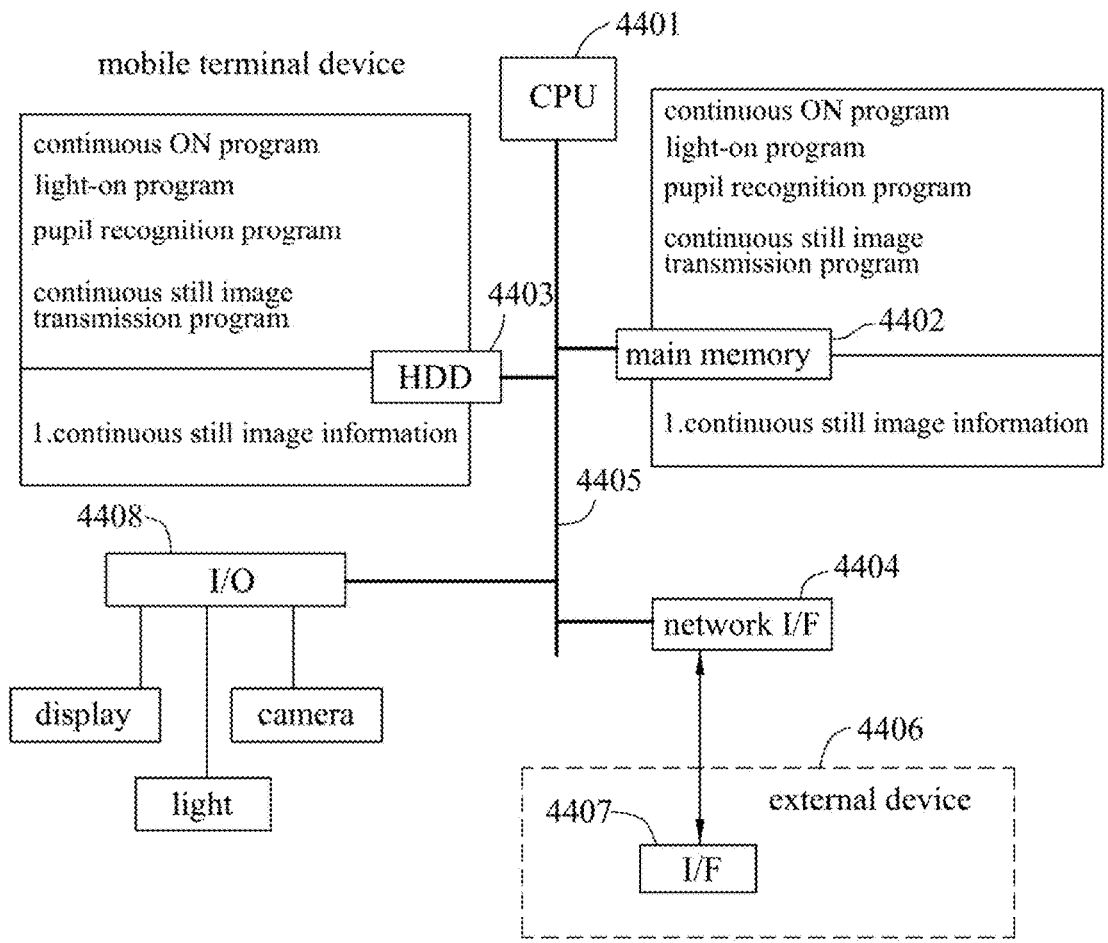
FIG. 29 is a schematic diagram showing the hardware structure of the mobile terminal device according to the tenth embodiment.

FIG. 29 is a diagram showing an example of the configuration of the mobile terminal device and the statistical processing device when the above functional components are implemented as hardware. Each of the hardware configuration parts for each processing of the device will be described with reference the figure.

As shown in the figure, the mobile terminal device of this embodiment is provided with a "CPU" (4401) for performing various arithmetic processing and a "main memory" (4402). In addition, the mobile terminal device further includes an "HDD" (4403), a "network I/F" (4404) for transmitting/receiving information to/from the "I/F" (4407) of the external device (4406), or an "I/O" (4408) for transmitting and receiving information between a camera, a light or a display. Then, they are mutually connected by a data communication route such as a "system bus" (4405) for transmitting/receiving or processing the information.

In addition, when the "CPU" reads and executes a program for performing various kinds of processing, the "main memory" provides a work area which is also a work area of the program. Also, a plurality of addresses are allocated to the "main memory", "HDD" or "flash memory" (not shown), respectively, and the program to be executed by the "CPU" are accessed by specifying their addresses so as to exchange data and to perform the processing. The stored program of the present embodiment includes a program for turning on the continuous still image capturing function of the mobile terminal; a light-on program for turning on the light provided on the image capturing side of the mobile terminal; a pupil recognition program for recognizing pupils of eyes of an animal including a person from an image that is being captured; and a continuous still image transmission program for transmitting the saved continuous still image to a preset address.

The pupil image of the user acquired by the video-on program of the mobile terminal device is stored in the addresses of the "main memory" and "HDD". Then, in the "CPU" of the mobile terminal device, the continuous still image information stored in the "main memory" is transmitted to the "I/F" of the external device via the "network I/F".

<Processing Flow>

Figure 30:
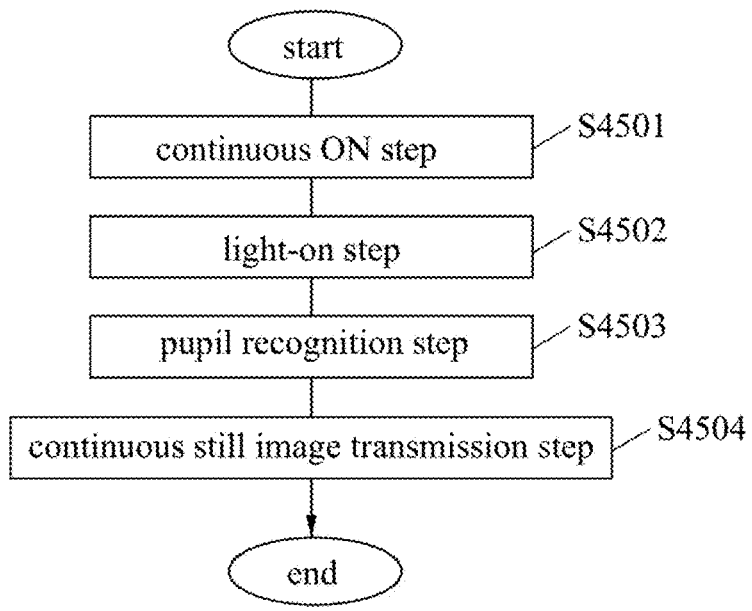
FIG. 30 is a flow chart showing a processing procedure according to the tenth embodiment.

FIG. 30 is a flow chart showing an example of the processing flow of the mobile terminal device of this embodiment. In addition, the following steps may be processing steps of a program recorded on a medium for controlling a computer (mobile terminal).

As shown in this figure, first, the continuous still image capturing function of the mobile terminal is turned on (S4501). Next, the light provided on the image capturing side of the mobile terminal is turned on (S4502). Then, a pupil of an eye of an animal including a person is recognized from the image being captured (S4503). Afterwards, a continuous still image captured by the continuous ON step is saved. Finally, the saved continuous still image is transmitted to a preset address. (S4504).

The order of the continuous ON step (S4501) for turning on the continuous still image capturing function of the mobile terminal and the light-on step (S4502) for turning on the light disposed at the image capturing side of the mobile terminal can be reversed. In other words, the processing flow can be as the following. First, the light disposed at the image capturing side of the mobile terminal is turned on. Next, the continuous still image capturing function of the mobile terminal is turned on. Then, a pupil of an eye of an animal including a person is recognized from the image being captured, and a continuous still image captured by the continuous ON step is saved. Finally, the saved continuous still image is transmitted to a preset address.

According to the above steps, it is unnecessary to perform the pupil change calculation by the mobile terminal device, and the stress state can be measured according to the objective symptoms having a correlation with stress.

Eleventh Embodiment

<Overview>

This embodiment provides a calculating device, which has a function for calculating the pupil response to light based on the moving image received from the mobile terminal device.

Hereinafter, functions and hardware contents of the device of this embodiment, and a processing flow will be described in detail.

<Functional Configuration>

Figure 55:
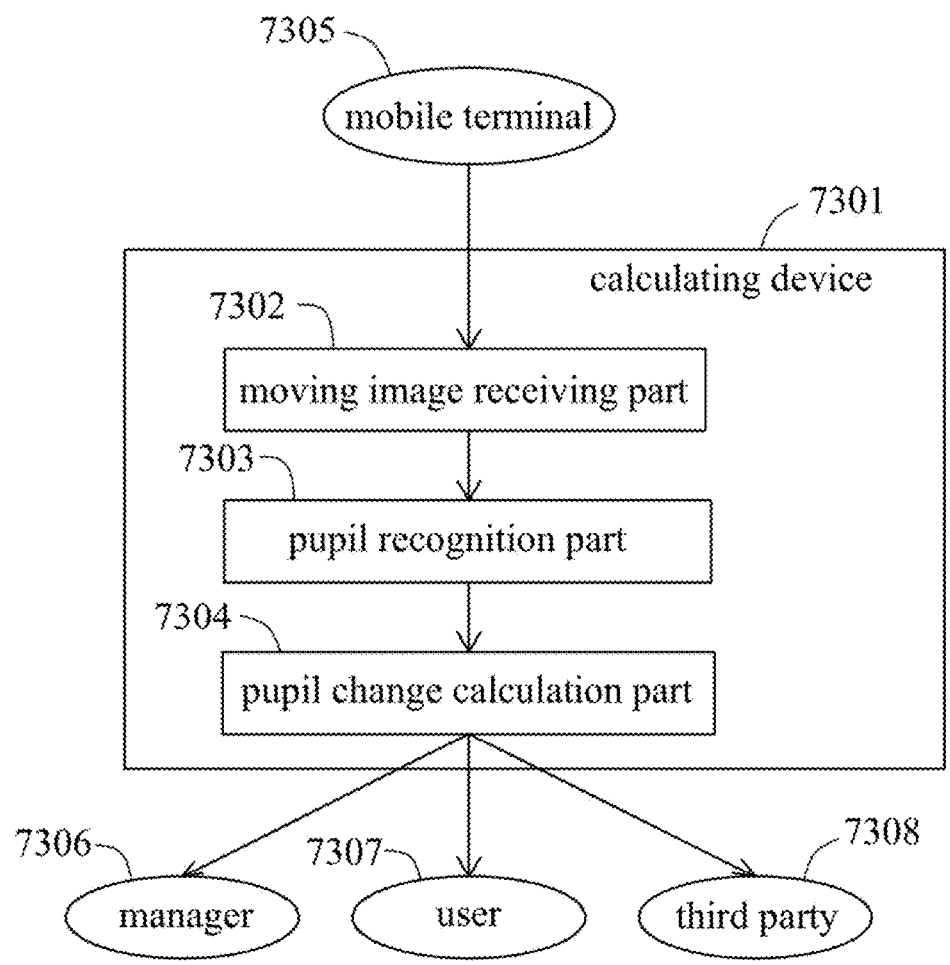
FIG. 55 is an experimental diagram showing the functional blocks of a mobile terminal device according to an eleventh embodiment.

FIG. 55 is an example of functional blocks of the calculating device of this embodiment. As shown in the figure, the calculating device (7301) of this embodiment includes a moving image receiving part (7302), a pupil recognition part (7303), and a pupil change calculation part (7304). Besides, in this embodiment, the mobile terminal usually includes a camera part, a light part, a video-on part, and a light-on part as shown in the first embodiment. The features of the camera part, light part, video-on part, and light-on part are the same as those of the first embodiment. In addition, the mobile terminal usually further includes a moving image transmission part for transmitting the moving image to the calculating device of this embodiment.

The "moving image receiving part" has a function for receiving a moving image including animal eyes, which include human eyes, from a mobile terminal (7305). Accordingly, the calculating device can receive the moving image including animal eyes, which include human eyes.

Moreover, the "pupil recognition part" has a function for recognizing pupils of the animal eyes, which include human eyes, from the received moving image. In addition, the "pupil change calculation part" has a function for calculating a pupil change, wherein the pupil change is a change in a dilation level of the recognized pupil over time. The detailed functions of the pupil recognition part and the pupil change calculation part of the calculating device are the same as the details of the pupil recognition part and the pupil change calculation part of the mobile terminal device of the first embodiment.

In addition, the calculating device further includes a notification transmission part for transmitting a notification to the user when the pupil of the received moving image cannot be recognized. Accordingly, the user can capture the moving image again and transmit it out upon receiving the notification, thereby improving the situation that the calculating device cannot execute the calculation of the pupil change. In order to further improve this effect, it may further includes a reason attaching device for attaching the reason of fail to recognition to the notification.

Furthermore, by transmitting the pupil change information, which is the operation result, to the user, the user can know the stress state of the user. Also, if it is provided to a third party other than the user, the third party can objectively grasp the stress. If the third party is a medical institution, for example, it becomes meaningful information at the time of examination. If the user is the employer, it also leads to prevention of illness and accidents caused by stress. In this way, it is preferable to have a function for transmitting the pupil change information to, for example, the administrator (7306), the user (7307), and the third party (7308). Therefore, the calculating device may have a pupil change transmission part for transmitting the pupil change to a predetermined address.

As a result, the camera part, the light part, the video-on part, the light-on part, and the moving image transmission part are required as functions necessary for the mobile terminal device, so that a mobile terminal such as a smartphone, which does not have any special function, may be capable of implementing the calculation. Therefore, since the user does not necessarily need to prepare a dedicated terminal or a dedicated application, the present invention can be easily used.

<Hardware Configuration>

Figure 56:
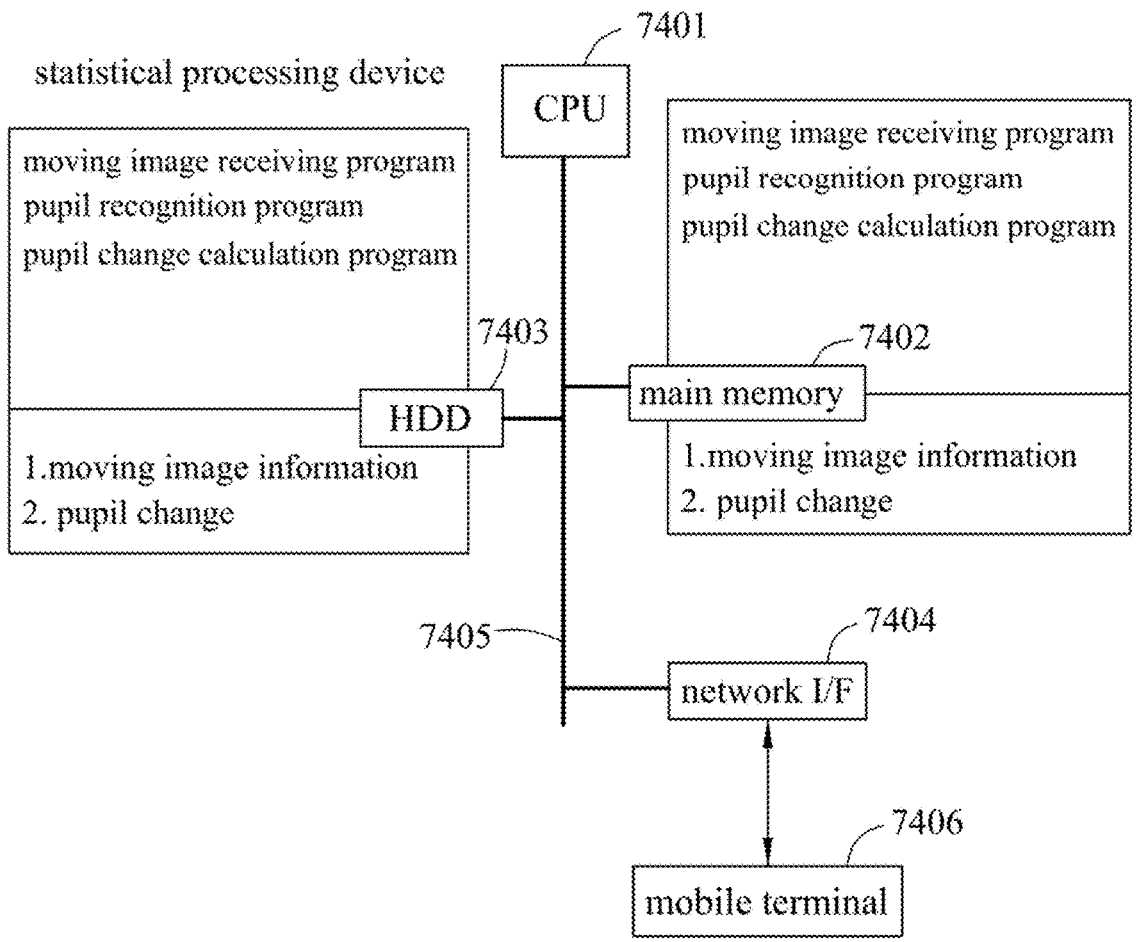
FIG. 56 is an experimental diagram showing the hardware structure of the mobile terminal device according to the eleventh embodiment.

FIG. 56 is a diagram showing an example of the configuration of the calculating device when the above functional components are implemented as hardware. The calculating device includes a "CPU" (7401), a "main memory" (7402), an "HDD" (7403), a "network I/F" (7404), an "I/O" (7408), and a "system bus" (7405), and are connected to the mobile terminal device (7406) through a "network I/F".

Respective hardware components in each processing in the present device will be described with reference to these figures.

In the calculating device of this embodiment, the contents of the program stored in the "main memory" are a moving image receiving program, a pupil recognition program, and a pupil change calculation program.

In the operation of "CPU", a moving image receiving program is executed to receive a moving image including an eye of an animal including a person transmitted from the mobile terminal device via the "network I/F", and the received moving image is stored in the "HDD" and "main memory". Then, the pupil recognition program is executed to recognize the pupils of the eyes of the animals including a person from the received moving images, and the pupil change calculation program is executed to calculate the pupil change. The pupil change is obtained by judging the dilation level of the pupil over time. The calculation result is stored as the "pupil change information" in the "HDD" and "main memory".

<Processing Flow>

Figure 57:
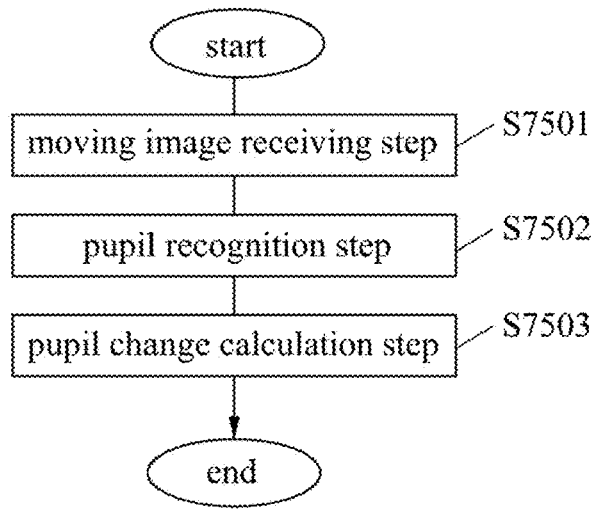
FIG. 57 is a flow chart showing the processing procedure according to the eleventh embodiment.

FIG. 57 is a flow chart showing an example of the processing flow of the calculating device of this embodiment. In addition, the following steps may be processing steps of a program recorded on a medium for controlling a computer (mobile terminal, calculating terminal).

As shown in this figure, first, a moving image including an eye of an animal including a person is received from the mobile terminal (S7501). Next, a pupil of an eye of an animal including a person is recognized from the received moving image (S7502). Next, a pupil change, which is the dilation level of the pupil over time, is calculated (S7503).

Details of the functions of the pupil recognition step (S7502) and the pupil change calculation step (S7503) are the same as those of the pupil recognition step and the pupil change calculation step of the mobile terminal device of the first embodiment.

Furthermore, the calculating device may have a notification transmission step for transmitting a notification to the user when the pupil of the moving image cannot be recognized. In addition, the notification may include a reason attaching step for attaching the reason of fail to recognition to the notification.

Furthermore, it may include a pupil change transmission step for transmitting the pupil change to a predetermined address.

Accordingly, a mobile terminal such as a smartphone, which does not have any special function, may be capable of implementing the calculation. Therefore, since the user does not necessarily need to prepare a dedicated terminal or a dedicated application, the present invention can be easily used.

Twelfth Embodiment

<Overview>

This embodiment provides a calculating device, which has a function for calculating the pupil response to light based on the continuous still image received from the mobile terminal device.

Hereinafter, functions and hardware contents of the device of this embodiment, and a processing flow will be described in detail.

<Functional Configuration>

Figure 58:
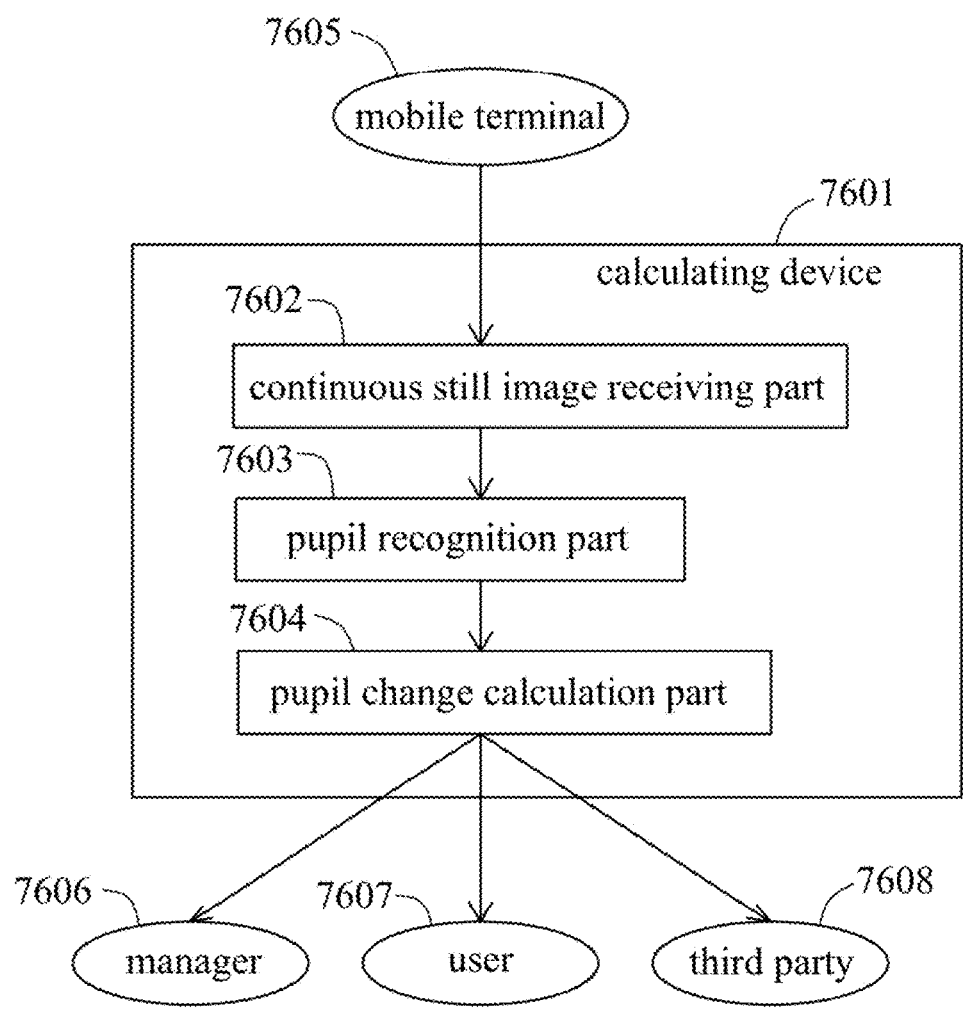
FIG. 58 is an experimental diagram showing the functional blocks of a mobile terminal device according to a twelfth embodiment.

FIG. 58 is an example of functional blocks of the calculating device of this embodiment. As shown in the figure, the calculating device (7601) of this embodiment includes a continuous still image receiving part (7602), a pupil recognition part (7603), and a pupil change calculation part (7604). Besides, in this embodiment, the mobile terminal usually includes a camera part, a light part, a continuous ON part, and a light-on part as shown in the sixth embodiment. The features of the camera part, light part, continuous ON part, and light-on part are the same as those of the sixth embodiment. In addition, the mobile terminal usually further includes a continuous still image transmission part for transmitting the continuous still image to the calculating device of this embodiment.

The "continuous still image receiving part" has a function for receiving a continuous still image including animal eyes, which include human eyes, from a mobile terminal (7605). Accordingly, the calculating device can receive the continuous still image including animal eyes, which include human eyes.

Moreover, the "pupil recognition part" has a function for recognizing pupils of the animal eyes, which include human eyes, from the received continuous still image. In addition, the "pupil change calculation part" has a function for calculating a pupil change, wherein the pupil change is a change in a dilation level of the recognized pupil over time. The detailed functions of the pupil recognition part and the pupil change calculation part of the calculating device are the same as the details of the pupil recognition part and the pupil change calculation part of the mobile terminal device of the first embodiment.

In addition, similar to the eleventh embodiment, the calculating device further includes a notification transmission part for transmitting a notification to the user when the pupil of the received continuous still image cannot be recognized. Moreover, it may further includes a reason attaching device for attaching the reason of fail to recognition to the notification.

In addition, it is preferable to have a function for transmitting the pupil change information to, for example, the administrator (7606), the user (7607), and the third party (7608). Therefore, the calculating device may have a pupil change transmission part for transmitting the pupil change to a predetermined address.

As a result, the camera part, the light part, the continuous ON part, the light-on part, and the continuous still image transmission part are required as functions necessary for the mobile terminal device, so that a mobile terminal such as a smartphone, which does not have any special function, may be capable of implementing the calculation. Therefore, since the user does not necessarily need to prepare a dedicated terminal or a dedicated application, the present invention can be easily used.

<Hardware Configuration>

Figure 59:
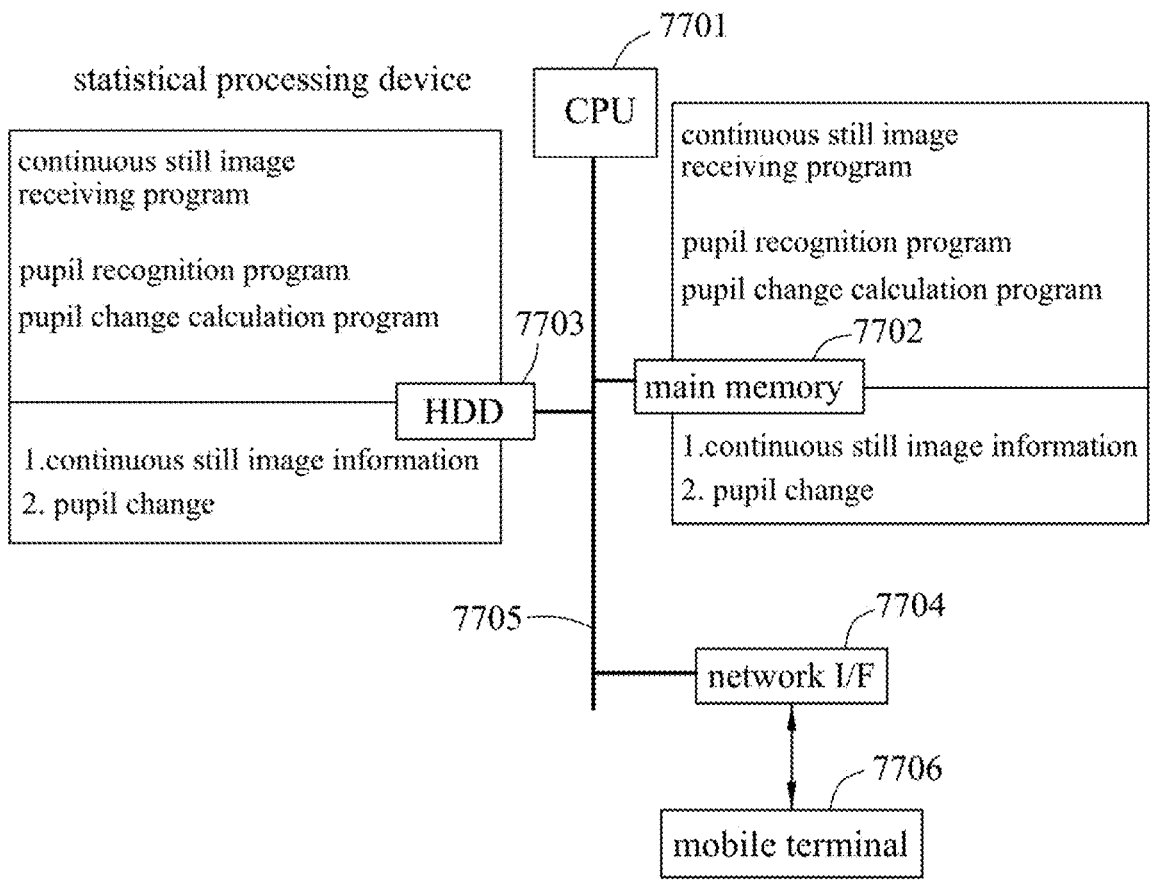
FIG. 59 is an experimental diagram showing the hardware structure of the mobile terminal device according to the twelfth embodiment.
Figure 60:
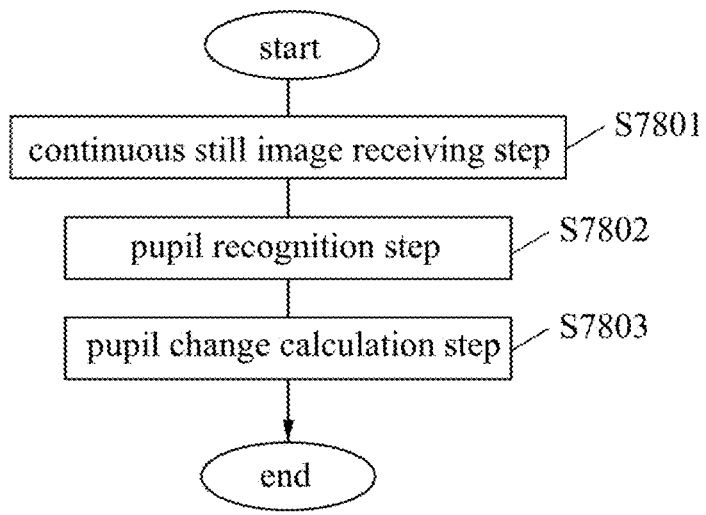
FIG. 60 is a flow chart showing the processing procedure according to the twelfth embodiment.

FIG. 59 is a diagram showing an example of the configuration of the calculating device when the above functional components are implemented as hardware. The calculating device includes a "CPU" (7701), a "main memory" (7702), an "HDD" (7703), a "network I/F" (7704), an "I/O" (7708), and a "system bus" (7705), and are connected to the mobile terminal device (7706) through a "network I/F".

Respective hardware components in each processing in the present device will be described with reference to these figures.

In the calculating device of this embodiment, the contents of the program stored in the "main memory" are a continuous still image receiving program, a pupil recognition program, and a pupil change calculation program.

In the operation of "CPU", a continuous still image receiving program is executed to receive a continuous still image including an eye of an animal including a person transmitted from the mobile terminal device via the "network I/F", and the received continuous still image is stored in the "HDD" and "main memory". Then, the pupil recognition program is executed to recognize the pupils of the eyes of the animals including a person from the received continuous still images, and the pupil change calculation program is executed to calculate the pupil change. The pupil change is obtained by judging the dilation level of the pupil over time. The calculation result is stored as the "pupil change information" in the "HDD" and "main memory".

<Processing Flow>

FIG. 57 is a flow chart showing an example of the processing flow of the calculating device of this embodiment. In addition, the following steps may be processing steps of a program recorded on a medium for controlling a computer (mobile terminal, calculating terminal).

As shown in this figure, first, a continuous still image including an eye of an animal including a person is received from the mobile terminal (S7501). Next, a pupil of an eye of an animal including a person is recognized from the received continuous still image (S7502). Next, a pupil change, which is the dilation level of the pupil over time, is calculated (S7503).

Details of the functions of the pupil recognition step (S7502) and the pupil change calculation step (S7503) are the same as those of the pupil recognition step and the pupil change calculation step of the mobile terminal device of the first embodiment.

Furthermore, the calculating device may have a notification transmission step for transmitting a notification to the user when the pupil of the continuous still image cannot be recognized. In addition, the notification may include a reason attaching step for attaching the reason of fail to recognition to the notification.

Furthermore, it may include a pupil change transmission step for transmitting the pupil change to a predetermined address.

Accordingly, a mobile terminal such as a smartphone, which does not have any special function, may be capable of implementing the calculation. Therefore, since the user does not necessarily need to prepare a dedicated terminal or a dedicated application, the present invention can be easily used.

DESCRIPTION OF REFERENCE NUMBERS

4601, 4701, 4801, 4901: mobile terminal device
4602, 4702, 4802: operation key
4603, 4703, 4803: receiving part
4604, 4704, 4804: camera
4605, 4705, 4805: light
4606, 4706, 4806: screen
4902: pupil part

What is claimed is:

1. A non-transitory computer-readable medium comprising a program which is recordable and readable by a mobile terminal device, wherein the mobile terminal device reads and executes the program to perform:
   a video-on step for enabling a moving image capturing function of the mobile terminal;
   a light-on step for enabling a light disposed at an image capturing side of the mobile terminal;
   a pupil recognition step for recognizing pupils of animal eyes from an image that is being captured, wherein the animal eyes include human eyes;
   an illuminance change step comprising:
      changing down an illuminance of the light until the pupil is recognized, and
      after the pupil recognition is completed, changing up the illuminance of the light greater than the illuminance of the light at the time that the pupil is recognized; and
   a pupil change calculation step for calculating a pupil change, wherein the pupil change is a change in a dilation level of the recognized pupil over time.

2. The non-transitory computer-readable medium according to claim 1, further comprising:
   a stress evaluation step for evaluating a stress level according to the pupil change obtained by the pupil change calculation step to obtain a stress evaluation result.

3. The non-transitory computer-readable medium according to claim 2, further comprising:
   a stress evaluation result transmission step for transmitting the stress evaluation result obtained by the stress evaluation step to a preset address.

4. The non-transitory computer-readable medium according to claim 1, further comprising:
   a pupil change transmission step for transmitting the pupil change obtained by the pupil change calculation step to a preset address.

5. A non-transitory computer-readable medium comprising a program which is recordable and readable by a computer, wherein the computer reads and executes the program to perform:
   a pupil change receiving step for receiving a pupil change from a mobile terminal device, wherein the mobile terminal device performs: a video-on step for enabling a moving image capturing function of the mobile terminal; a light-on step for enabling a light disposed at an image capturing side of the mobile terminal; a pupil recognition step for recognizing pupils of animal eyes from an image that is being captured, wherein the animal eyes include human eyes; an illuminance change step comprising changing down an illuminance of the light until the pupil is recognized, and after the pupil recognition is completed, changing up the illuminance of the light greater than the illuminance of the light at the time that the pupil is recognized; a pupil change calculation step for calculating a pupil change, wherein the pupil change is a change in a dilation level of the recognized pupil over time; and a pupil change transmission step for transmitting the pupil change obtained by the pupil change calculation step to a preset address;
   a pupil change accumulation step for accumulating the received pupil change; and
   a pupil change statistical processing step for performing a statistical processing of the accumulated pupil changes.

6. A non-transitory computer-readable medium comprising a program which is recordable and readable by a computer, wherein the computer reads and executes the program to perform:
   a stress evaluation result receiving step for further receiving a stress evaluation result from a mobile terminal device, wherein the mobile terminal device performs: a video-on step for enabling a moving image capturing function of the mobile terminal; a light-on step for enabling a light disposed at an image capturing side of the mobile terminal; a pupil recognition step for recognizing pupils of animal eyes from an image that is being captured, wherein the animal eyes include human eyes; an illuminance change step comprising changing down an illuminance of the light until the pupil is recognized, and after the pupil recognition is completed, changing up the illuminance of the light greater than the illuminance of the light at the time that the pupil is recognized; a pupil change calculation step for calculating a pupil change, wherein the pupil change is a change in a dilation level of the recognized pupil over time; a stress evaluation step for evaluating a stress level according to the pupil change obtained by the pupil change calculation step to obtain a stress evaluation result and a stress evaluation result transmission step for transmitting the stress evaluation result obtained by the stress evaluation step to a preset address;

a stress evaluation result accumulation step for accumulating the received stress evaluation result;

a pupil change receiving step for further receiving the pupil change transmitted out by the program wherein the pupil change transmitted is obtained by the pupil change calculation step to a present address;

a pupil change accumulation step for accumulating the received pupil change; and a pupil change statistical processing step for performing a statistical processing of the accumulated pupil changes and the accumulated stress evaluation results.

7. The non-transitory computer-readable medium according to claim 6, wherein the video-on step for enabling the moving image capturing function of the mobile terminal is replaced by a continuous ON step for enabling a continuous still image capturing function of the mobile terminal.

8. A mobile terminal device, comprising:

a camera part for capturing a moving image and/or a still image;

a light part comprising a light disposed at an image capturing side of the mobile terminal;

a video-on part for enabling a moving image capturing function of the mobile terminal;

a light-on part for enabling the light;

a pupil recognition part for recognizing pupils of animal eyes from an image that is being captured, wherein the animal eyes include human eyes;

an illuminance change part for:
changing down an illuminance of the light until the pupil is recognized, and
after the pupil recognition is completed, changing up the illuminance of the light greater than the illuminance of the light at the time that the pupil is recognized; and a pupil change calculation part for calculating a pupil change, wherein the pupil change is a change in a dilation level of the recognized pupil over time.

9. The mobile terminal device according to claim 8, further comprising:

a stress evaluation part for evaluating a stress level according to the pupil change calculated by the pupil change calculation part to obtain a stress evaluation result.

10. The mobile terminal device according to claim 9, further comprising:

a stress evaluation result transmission part for transmitting the stress evaluation result obtained by the stress evaluation part to a preset address.

11. The mobile terminal device according to claim 8, further comprising:

a pupil change transmission part for transmitting the pupil change calculated by the pupil change calculation part to a preset address.

12. The mobile terminal device according to claim 8, wherein the video-on part for enabling the moving image capturing function of the mobile terminal is replaced by a continuous ON part for enabling a continuous still image capturing function of the mobile terminal.

13. An evaluation system, comprising:

a mobile terminal device, comprising:

a camera part for capturing a moving image and/or a still image;

a light part comprising a light disposed at an image capturing side of the mobile terminal;

a video-on part for enabling a moving image capturing function of the mobile terminal;

a light-on part for enabling the light;

a pupil recognition part for recognizing pupils of animal eyes from an image that is being captured, wherein the animal eyes include human eyes;

an illuminance change part for:
changing down an illuminance of the light until the pupil is recognized, and
after the pupil recognition is completed, changing up the illuminance of the light greater than the illuminance of the light at the time that the pupil is recognized;

a pupil change calculation part for calculating a pupil change, wherein the pupil change is a change in a dilation level of the recognized pupil over time; and a pupil change transmission part for transmitting the pupil change calculated by the pupil change calculation part to a preset address; and a statistical processing device, comprising:

a pupil change receiving part for receiving the pupil change transmitted out by the mobile terminal device;

a pupil change accumulation part for accumulating the received pupil change; and a pupil change statistical processing part for performing a statistical processing of the accumulated pupil changes.

14. An evaluation system, comprising:

a mobile terminal device, comprising:

a camera part for capturing a moving image and/or a still image;

a light part comprising a light disposed at an image capturing side of the mobile terminal;

a video-on part for enabling a moving image capturing function of the mobile terminal;

a light-on part for enabling the light;

a pupil recognition part for recognizing pupils of animal eyes from an image that is being captured, wherein the animal eyes include human eyes;

an illuminance change part for:
changing down an illuminance of the light until the pupil is recognized, and
after the pupil recognition is completed, for changing up the illuminance of the light greater than the illuminance of the light at the time that the pupil is recognized;

a pupil change calculation part for calculating a pupil change, wherein the pupil change is a change in a dilation level of the recognized pupil over time;

a stress evaluation part for evaluating a stress level according to the pupil change calculated by the pupil change calculation part to obtain a stress evaluation result; and a stress evaluation result transmission part for transmitting the stress evaluation result obtained by the stress evaluation part to a preset address; and a statistical processing device, comprising:

a stress evaluation result receiving part for further receiving the stress evaluation result transmitted out by the mobile terminal device;

a stress evaluation result accumulation part for accumulating the received stress evaluation result;

a pupil change receiving part for further receiving the pupil change transmitted out by the program according to wherein the pupil change transmitted is obtained by the pupil change calculation step to a present address;

a pupil change accumulation part for accumulating the received pupil change; and a pupil change statistical processing part for performing a statistical processing of the accumulated pupil changes and the accumulated stress evaluation results.

* * * * *

UNITED STATES PATENT AND TRADEMARK OFFICE
CERTIFICATE OF CORRECTION

PATENT NO. : 10,741,286 B2
APPLICATION NO. : 15/576965
DATED : August 11, 2020
INVENTOR(S) : Ryozo Saito Page 1 of 1

It is certified that error appears in the above-identified patent and that said Letters Patent is hereby corrected as shown below:

(71) Applicants should be changed from:
"Saito; Ryozo (Tokyo, JP)
Takahashi; Hirotsugu (Tokyo, JP)
Kayama; Tetsu (Kanagawa, JP)"

To:
--Saito; Ryozo (Tokyo, JP)
Takahashi; Hirotsugu (Tokyo, JP)
Kayama; Tetsu (Kanagawa, JP)
Hsieh; Su-Li (Taipei City, TW)--

Signed and Sealed this
Eighth Day of September, 2020

Andrei Iancu
*Director of the United States Patent and Trademark Office*